United States Patent
Sensen et al.

(10) Patent No.: US 10,793,906 B2
(45) Date of Patent: Oct. 6, 2020

(54) METHODS FOR TREATING AND DETECTING SEPSIS IN HUMANS

(71) Applicant: CNA Diagnostics Inc., Calgary (CA)

(72) Inventors: Christoph W. Sensen, Vasoldsberg (AT); Jung Soh, Calgary (CA); Petra Heidinger, Graz (AT); Laura Villanova, Hart bei Graz (AT); Stefan Grabuschnig, Graz (AT)

(73) Assignee: CNA DIAGNOSTICS INC., Calgary (CA)

( * ) Notice: Subject to any disclaimer, the term of this patent is extended or adjusted under 35 U.S.C. 154(b) by 0 days.

(21) Appl. No.: 16/526,923

(22) Filed: Jul. 30, 2019

(65) Prior Publication Data

US 2020/0032336 A1    Jan. 30, 2020

Related U.S. Application Data

(60) Provisional application No. 62/711,970, filed on Jul. 30, 2018.

(51) Int. Cl.
*C12Q 1/6876* (2018.01)

(52) U.S. Cl.
CPC ...... *C12Q 1/6876* (2013.01); *C12Q 2600/112* (2013.01); *C12Q 2600/158* (2013.01)

(58) Field of Classification Search
CPC ............ C12Q 1/6876; C12Q 2600/112; C12Q 2600/158
See application file for complete search history.

(56) References Cited

U.S. PATENT DOCUMENTS

| | | |
|---|---|---|
| 2005/0037344 A1 | 2/2005 | Stuhlmuller et al. |
| 2005/0228172 A9 | 10/2005 | Wang |
| 2010/0041564 A1 | 2/2010 | Russwurm et al. |
| 2012/0228312 A1 | 11/2012 | Sirard et al. |
| 2017/0000929 A1 | 1/2017 | Spencer et al. |

FOREIGN PATENT DOCUMENTS

| | | |
|---|---|---|
| WO | 2007144105 A1 | 12/2007 |
| WO | 2011057411 A1 | 5/2011 |
| WO | 2015121605 A1 | 8/2015 |

OTHER PUBLICATIONS

Sensen (Biomarkers of Injury and Infection, Mar. 2015).*
Blast (RID-6Z624Z6F016, https://blast.ncbi.nlm.nih.gov/Blast.cgi downloaded Mar. 16, 2020).*
Blast (RID-6Z6ADAK5014, https://blast.ncbi.nlm.nih.gov/Blast.cgi downloaded Mar. 16, 2020).*
Zinkova (Nature Scientific reports (2017) vol. 7, pp. 1-8).*
Ahmed et al., "Cell Free DNA and Procalcitonin as Early Markers of Complications in ICU Patients with Multiple Trauma and Major Surgery," Clin. Lab., pp. 2395-2404 (2016).
Gogenur et al., "The role of total cell-free DNA in predicting outcomes among trauma patients in the intensive care unit: a systematic review," Critical Care, 21:14, 10 pages (2017).
Palmeri et al., "Differential gene expression profile of human tonsil high endothelial cells: implications for lymphocyte trafficking," Journal of Leukocyte Biology, vol. 75, No. 5, pp. 910-927 (2004).
Thurairajah et al., "The source of cell-free mitochondrial DNA in trauma and potential therapeutic strategies," European Journal of Trauma and Emergency Surgery, pp. 325-334 (2018).
International Search Report to corresponding International Application No. PCT/IB2019/000718, dated Dec. 16, 2019 (6 pages).
Written Opinion of the International Searching Authority to corresponding International Application No. PCT/IB2019/000718, dated Dec. 16, 2019 (7 pages).

* cited by examiner

*Primary Examiner* — Steven Pohnert
(74) *Attorney, Agent, or Firm* — Barry J. Schindler; Natalie Salem; Greenberg Traurig, LLP

(57) ABSTRACT

Biomarkers for identifying sepsis in humans are presented herein, as are related methods, uses, agents, and kits comprising same. Methods for treating, detecting, and diagnosing sepsis in humans are presented herein.

8 Claims, 23 Drawing Sheets

Specification includes a Sequence Listing.

Table 1

| Final motif ID | Interim motif ID | Patent ID | Length (bp) | Sequence | SEQ ID NO: | Locus | Annotation | fwd Primer | SEQ ID NO: | reverse Primer | SEQ ID NO: |
|---|---|---|---|---|---|---|---|---|---|---|---|
| Sepsis JC1 | Set1Ct01 | hu-sep-CNAD-0001 | 166 | AAACGTCCGCTTGCAGATACTACAAAAAGAGCGTTTC AAACCTGCTCTATGAAAGGCAATGTTCAACTCTGTGA CTTGAATGCAGACATCACAGAGCAGTTTCTGAGAATG CTTCTGTCTAGATTTTATAGGAAGATATTCCCGTTTCC AACGAAATCTTCACAGC | 1 | chr13:17,039,041-17,039,206 | Name: ALR/Alpha Family: centr Class: Satellite | AAACGTCCGCTTG CAGATAC | 183 | GCTGTGAAGATTT CGTTGGAAAAC | 240 |
| Sepsis JC2 | Set1Ct02 | hu-sep-CNAD-0002 | 146 | GGAAATATGCCAAAGTATTTTCTGAGTATGCTGCTGT GTACGTTTATATTGCATCCCGTTTCCAACGAAATCCT CAAACGCGATCCAAATATCCCACTTGCAGATTCCAAAAA AAGAGTGTTTCAAACTGCTCTGTCTGTCAGTAGCAAGG | 2 | chr8:44,195,216-44,195,361 | Name: ALR/Alpha Family: centr Class: Satellite | AGTATGCTGCTGT GTACGTTT | 184 | CCTTTGTTACTGAC AGAGCAGTT | 241 |
| Sepsis JC3 | Set1Ct03 | hu-sep-CNAD-0003 | 261 | TCTTTGAGCGCTTTCGTTCGGAAACGGGATTTCTTCACA TAATGCTAGACAGAAGAATTCTCAGTAACTTCTTTTGG GATGTATGTATTCAACTCAGAGAGTTGAACCTTCCTTT AGACAGAGCGGATTGGAAAACACGCTTTTGCCGGAATT TTCAGGTGGAGAGATTCCAAGAGCCTGAGGCCAGTGG TAGAAAAGGCTATCTTCGTATAAAACTAGAGGGAAT CATTCTCAGAAACTGCTTTGTGATGTGTGCATTAAACT | 3 | chr3:93,326,653-93,326,913 |  |  |  |  |  |
| Sepsis JC4 | Set1Ct04 | hu-sep-CNAD-0004 | 199 | TGTGAACTCAGCTAACAGAGAGGTGGATCTTTCTTTGA TAGAGCAGTTCTGAAAAAACACTTTTGTTGAATCTGCA AGTGGACATTTGGATAGATTTGAAGATTTCGTTGGAA ACGGGAATATCTTCATATCAAATCTAGACAGCAGCAT TCCCAGAAATTTCTTTCGGATATTTCCATTCAACTCAT AGAGATGAACAT | 4 | chr22:14,141,093-14,141,290 | Name: ALR/Alpha Family: centr Class: Satellite | TTTGAGGCTTTCG TTGGAAAAC | 185 | GCACACATCACAA AGCAGTT | 242 |
| Sepsis JC5 | Set1Ct05 | hu-sep-CNAD-0005 | 214 | CTTGTGGCCTTCGTTGGGAAACGGGATTTCTTCATATT ATGCTAGACAGAAGAATTCTCAGTAACTTCCTTGTGTT GTGTGTATTCAACTCACAGAGTTGAACGATCCTTTAC ACAGAGCAGACTTGAAACACTCTTTTTGTGGAA TTG CAAGTGGAGAGATTTCAGCGCCCTTTGAGTTCAATGGTAG TATAGGAAATATCTTCCTATAGAAACTA | 5 | chr5:48,533,848-48,534,061 | Name: ALR/Alpha Family: centr Class: Satellite | TCAGCTAACAGA GGTGGATCT | 186 | CTATGAGTTGAAT GGAAATATCCGAA AG | 243 |
| Sepsis JC6 | Set1Ct06 | hu-sep-CNAD-0006 | 171 | ATATTTGGATAGCTGTGAAGATTCGTTGGAAACGGG AATATCTTCCTATAAAATCTAGACAGAAGCATTCTCAG AAACTGCTCTGTGATGTTGCATTCAAGTCACAGAGT TGAACATTGCCTTTCCTAGACAGAGGTTGAAACGCTCT TTTGGTAGTATATGGAAGTGGA | 6 | chr21:11,278,706-11,278,877 |  |  |  | ATTGAACTCAAAG CGGCTGAA | 244 |
| Sepsis JC7 | Set1Ct07 | hu-sep-CNAD-0007 | 160 | CTCACGTAACAGAGGTGGATCTTTCTTTTTGATAGAGC AGTTCTGAAAAAACACTTTTGTTGAATCTGCAAGTGGA CATTTGGATAGATTTGAAAGATTTCGTTGGAAAACGGGA ATATCTCATATCAAATCTAGACAGAAGCATTCTCAGA ATCTTCTTTG | 7 | chr14:16,974,315-16,974,474 | Name: ALR/Alpha Family: centr Class: Satellite | CTTGTGGCCTTCG TTGGAAAA | 187 | ATTGAACTCAAAG CGGCTGAA | 244 |
| Sepsis JC8 | Set1Ct08 | hu-sep-CNAD-0008 | 140 | AGTGGAGAACACACACATCACAATCAAGGTTCTGAGAAT GCTTCTGTCTAAAATTTCTATGAAGACAATTCCCGTTTC CAACGAAATTCTACAGCTATCCAAATATCCACTTGC AGATTCTACAAAAAGTGTGGTTCAAAAC | 8 | chr8:44,144,110-44,144,249 | Name: ALR/Alpha Family: centr Class: Satellite | GATAGCTGTGAA GATTTCGTTGG | 188 | AGCGTTTCAAACC TCTCTAGG | 245 |
|  |  |  |  |  |  |  | Name: ALR/Alpha Family: centr Class: Satellite | TCAGCTAACAGA GGTGGATCT | 189 | TTCTGAGAATGCT TCTGTCTAGATT | 246 |
|  |  |  |  |  |  |  | Name: ALR/Alpha Family: centr Class: Satellite | GTGGAGAACACA CATCACAATC | 190 | GTAGAATCTGCAA GTGGATATTTGG | 247 |
| Sepsis JC9 | Set1Ct10 | hu-sep-CNAD-0009 | 261 | AATATCTTCCCCTACAAGCTAGAAAGAAGCATTCTGT GAAACTTGTTTGTGATGTGTGACTCAACTAACACAGAG AAGACCTTCCTTTTGCAAGTGGATATTGGATAGCTG TTTTGTAGAATCTCGCAAGTGGAAATCGGATAGCTG TGAAGATTTCGTTGGAAACGGGATTATCTCCTATAAA ATCTAGACAGAAACCATTCTCAGAAACTACTCTGTGAT GTCTGCATTCAAGTCACAGAGTTGAACATTGCCTTTC | 9 | chr22:14,188,977-14,189,237 | Name: ALR/Alpha Family: centr Class: Satellite | CCCTACAAGCTAG AAAGAAGCA | 191 | AAAGGGAATGTTC AACTCTGTG | 248 |

FIG. 1A

Table 1 continued

| | | | | | | | | |
|---|---|---|---|---|---|---|---|---|
| Sepsis JC10 | Set1Ctl1 | hu-sep-CNAD-0010 | 137 | CCTTTATGACGTATGCACTCACCTAACAGAAGAAC CTTCCTTTGACAGAGCAGTTTGATACACTCTTTTG TAGAATCTGCAAGTGGATATTTGGATAGCTGTGAAGA TTTCGTTGGAAACGGGAATATCTTC | 10 | chr21:12,252,491-12,252,627 | Name: ALR/Alpha Family: centr Class: Satellite | ATGACGTATGCA CTCACCTAAC | 192 | GATATTCCCGTTTC CAACGAAATC | 249 |
| Sepsis JC11 | Set1Ctl2 | hu-sep-CNAD-0011 | 254 | TTTTTGTGTATCTGGATGTGGACATTTGGAGCGCTTT CAGCCCTATGCTGTGAAAAAGGAAATATCTTCCTGAA AACTAGAACAGAAGCATTCTCAGAATCTTATTTGTGATG TGCCGCCTCCAACTAACACAGTTGAAGCTTCTTCTGA TAGAGCAGTTTTGAAACACTCTTTTCGTAAAATCTGGA AGAGATATTTTGATAGCTTTGAGGATTTCGTTGGAA ACGGGATTGTCTTCATATAAACTCTAGAC | 11 | chr2:92,713,661-92,713,914 | Name: ALR/Alpha Family: centr Class: Satellite | TTGTATCTGGATG TGGACATTTG | 193 | GTCTAGAGTTTAT ATGAAGACAATCC C | 250 |
| Sepsis JC12 | Set1Ctl3 | hu-sep-CNAD-0012 | 288 | CTTTAAGGTCAATGGCAGAAAAGGAAATATCTTCGTTT CAAAACTAGAACAGAATCATTCCCACAAACTGCGTTGT GATGTGTTCGTTCAACTCAACAGAGTTTAGCCTTTCTT TCATAGAGCAGTTAGGAACAACTCTGTTTGTAAACTCT GCAAGTGGATATTCAGACCTCTTTGAGGCCTTCGTTG GAAACGGGATTTCTTCACTATACTGAGACAGAAGAA TTCTCAGTAACTTCCACGTGTGTGTATTCAACTCA CAGAGCTGAACGATCCTTTACACAG | 12 | chr5:49,180,744-49,223,671 | Name: ALR/Alpha Family: centr Class: Satellite | GACAGAATCATTC CCACAAACTG | 194 | GTGTAAAGGATC GTTCAGCTCT | 251 |
| Sepsis JC13 | Set1Ctl4 | hu-sep-CNAD-0013 | 208 | AAGAATTCTCAGTAGCTCTTTTGTGTGTGTATTCAACT CACAGAGTTGAACCTTCCTTTAGACAGAGACAGACTTG AAACACTCTTTTGTGGAATTTGCAAGTGGAATATTTCA GCCGCTTTGAGGTCCAATGGCAGAGACTAGGAATATCTT CCAATAGAAACTAGAACAGAATGATTCTCAGAAACTCC TTTGTGATGTGTGCGTTCAAC | 13 | chr5:49,179,944-49,180,154 | Name: ALR/Alpha Family: centr Class: Satellite | GAATTCTCAGTAG CTTCTTTGTGT | 195 | GTTGAACGCACAC ATCACA | 252 |
| Sepsis JC14 | Set1Ctl5 | hu-sep-CNAD-0014 | 126 | GAAGAATTCCCGTTTCCAACGAAGGCCACAAGATGTC AGAATATCCACTTACACAGACTTTACAACAGAGTGTTTC CTAACTGCTCTATGAACACAGAAAAGGTTAAACTCTGTGA GTTGAACGAACACA | 14 | chr5:49,467,511-49,467,636 | Name: ALR/Alpha Family: centr Class: Satellite | ATTCCCGTTTCCA ACGAAGG | 196 | TGTGTTCGTTCAA CTCACAGAG | 253 |
| Sepsis JC15 | Set1Ctl6 | hu-sep-CNAD-0015 | 254 | GAGTTCAACCTTTCTTTTGTTATGATACACAGCAGTTGGAAAACA CTCTTTATAGAATTTGCAAGCTGATACATGGATAGC CCTAACTATTTCGTTGGAAACGGGAACACTCTCAGAAACTACTTTGTG AAACCTAGAACAGAAGCACTCTCAGAAGAGTTTCCCTTT ATATCTGCATTGATATCAGAGAGGTCTTTTCTGGAATCT CTAAGGACGAGGCTTGGAACGTCTCTTTTCGTGGAATCT GCAGGAACGATATTTGGATAGCTTGGAGG | 15 | chr18:15,584,732-15,584,985 | Name: ALR/Alpha Family: centr Class: Satellite | CCTTTCTTATGAT ACAGCAGTTTGG | 197 | CCTCCAAGCTATC CAAATATCCTC | 254 |
| Sepsis JC16 | Set1Ctl7 | hu-sep-CNAD-0016 | 171 | ATTCTTCTGTCTAGCATATGAAGAGAATCCCGTTTC CAACGAAGGCCTCAAAAGAGGTCTGAATATCCACTTGC AGAGTTTACAAACAGAAGTTGTTTCCTAACTGCTCTATGA AGAGAATTTGTTTAAACTCTGTCAGTTGAACGCACACAT CACAAAGAAGTTCTGAGAAT | 16 | chr1:124,747,548-124,747,718 | Name: ALR/Alpha Family: centr Class: Satellite | TCTGTGCTAGCATA GTATGAAGAAAT CC | 198 | CTCAGAAACTTCT TTGTGATGTGTG | 255 |
| Sepsis JC17 | Set1Ctl8 | hu-sep-CNAD-0017 | 219 | GTAAAGTCTGCAAGTGGATGTTTGACCTCTTTGAGG CCTTCGTTGGAAACGGGATTTCTTCATATAATTCTAGA CAGCAGAATTTTGAACACAGTTGAACCATCCTTTACAGACA TCAACTCACAGAGTTGAACGATCCTTTTGTGGAATTTGCAAGTGGA GACTTGAAACATCTTTTTGAGGTCAATAGTAGAAA GATTTCAGCCGCCTTCAGGGTCAATAGTAGAAA | 17 | chr19:25,955,048-25,955,266 | Name: ALR/Alpha Family: centr Class: Satellite | GTAAAGTCTGCA AGTGGATGTT | 199 | TTTTACTATTGAC CTCAAAGCG | 256 |

FIG. 1B

Table 1 continued

| | | | | | | | | | |
|---|---|---|---|---|---|---|---|---|---|
| Sepsis IC18 | Set1Ctl19 | hu-sep-CNAD-0018 | 211 | CTCCCACCATAGCCCTCAAAGGCGCTCCAAGTGTCCGCTAGCAGATTCCACAGAAGATTCAACTCCGTAGTGTTCAAAACTGCTCTACATCACAAAGCATTTCTGTGAATCCTCTCTGTCAGTTTTATATGAGGATATTTCCTTTTCTACCATGGGCATCAAAGGGTTCCAATTTATCCAATTGT | 18 | chr5:50,131,204-50,131,414 | Name: ALR/Alpha Family: centr Class: Satellite | CTCCACCATAGCCCTCAAAA | 200 | ACAATTGGATAATTGGAACCCT | 257 |
| Sepsis IC19 | Set1Ctl20 | hu-sep-CNAD-0019 | 234 | ATGACGCTTCTGAGAATGCTTCTGTCTAGAGTTTATATGAAGACAATCCCGTTTCCAACGAAATCCTCAAAGCTATCCAAATATCCTCTTGCAGATTTTACAAAAAGAGTGTTTCAAAACTGCTCTATCAAAAGAAAGCTTCAACACTGTTAGTTGAGGGCGCAACTAATAGGATTCTAAGAATTCTTCTGTCTAGTTTTTATTTGAAGATATTTCCTTTCTCACCATAG | 19 | chr2:93,798,641-93,798,874 | Name: ALR/Alpha Family: centr Class: Satellite | TGAGAATGCTTCTGTCTAGAGTT | 201 | TCTTAGAATCCTATTTGTGATGTGC | 258 |
| Sepsis IC20 | Set1Ctl21 | hu-sep-CNAD-0020 | 221 | GGAATGTTCAACTCTGTGACTTGAACTGCAGACATCACAGAGCAGTTTCTGAGAATCTCTGTCTCTAGATTTTATAGGAAGATATTCCCGTTTCCAACGAAATCTTCACAGCTATCCAAATATCCACTTGCAGATTCAAACAAAAGTGTTTTTCAGAACTGCTCTATCAAAAGAAAGATTCCACTCCTGTTAGCTGAGTTCAGCACATCACAAACAAGTTTATG | 20 | chr22:14,291,014-14,291,576 | Name: ALR/Alpha Family: centr Class: Satellite | GGAATGTTCAACTCTGTGACTT | 202 | ACTTGTTTGTGATGTGTGAACT | 259 |
| Sepsis IC25 | Set2Ctl01 | hu-sep-CNAD-0021 | 195 | CAATCCCTGTCTTGTGCCAGTTTTCAAAGGGAATGCTTCCAGTTTTGTCATAGAATAGCTCTTATTATTTTGAAGATATGTCCTTTGTCATAGATAGCTCTTATTATTTTGAAGATATGTCCTCCTCTCCACCACTCCTCTATTCAACATAGTGTTGGAAGTTCTGGCC | 21 | chr8:25,012,948-25,013,069 | Name: L1PA4 Family: L1 Class: LINE | CCCTGTCTCGTGCCAGTTT | 203 | GGCCAGAACTTCCAACACTAT | 260 |
| Sepsis IC26 | Set2Ctl02 | hu-sep-CNAD-0022 | 174 | AAAGAGACTTTAAAACAACAAAGATCAAACAAAGAGACAAAGAAGGCCATTACATATCACTATCCTAAATATATGCACCCAACAAGAGCTAACTATTCATAAAGCAACAAAGATCAAATTCAACAACAAACACACTCAGACGTAAAACAATC | 22 | chr12:38,228,523-38,228,647 | Name: L1PA4 Family: L1 Class: LINE | AAAGAGACAAAGAAGGCCATTAC | 204 | TTTACGTCTGATTGTGTGTTCC | 261 |
| Sepsis IC27 | Set2Ctl03 | hu-sep-CNAD-0023 | 292 | AAATCCTCCAATTAAAAGACACAGACTGGCAAATTGGATAAAGAGTCAAGACCCATCAGAGTGCTGTATTCAGGAAACCCATCTCAATGCAGAGACACACATAGGGCTCAAAATGAAGGGATGGAGGAAGATCTACCAAGCAAATGGAAAAAAAAAAGACACTTTAAACCAACAAAGATCAAAAGAGGATAAAACAGACTTTAAACCAACAAAGAGACAAAGAGACAAAGAAGGCCATTACATAGTGGTAAAGGGATCAATTCAAGAAGAGAGCTAACTATCCTAAATATAT | 23 | chr6:99,973,260-99,973,551 | Name: L1PA4 Family: L1 Class: LINE | AAAGACACAGACTGGCAAAT | 205 | TTAGGATAGTTAGCTCTTCTTGTTG | 262 |
| Sepsis IC28 | Set2Ctl04 | hu-sep-CNAD-0024 | 228 | GCAGTAGAGGATATAACTGCCCATAAAAACTAGACAGTAGCATTCCCAGGAAAACACTTTGTGACGATTGAGTTCAACTCACAGAGCTGAACATTCCTTTGGATGGAGCAGTTTCAAAACACACTTCTGTAGAATCTGCAAGTGGATATTGGAACCTCTCTGAGGATTTCGTTGGATACCGGGAGAAAACTCACCTATCTAAAGAGAAGCATTCTCAGAACCTT | 24 | chr1:122,299,327-122,299,554 | Name: ALR/Alpha Family: centr Class: Satellite | CAGTAGAGGATATAACTGCCCATAAA | 206 | AGGTTCTGAGAATGCTTCTTT | 263 |
| Sepsis IC29 | Set2Ctl05 | hu-sep-CNAD-0025 | 264 | GCTCTGTGTAAAGGATCGTTCAACTCTGTGAGTTGAATACACAACAGTGTTTCAAGGAAGTTACTGAGAATTCTTCTGTCTAGCCTTATATGAAAGAGGTCTGAATATCCACTTGCAGACTTTACAAAAGAGAGTGTTTCCTAACTGTGTTGGGTGTGTTTGGGGTTTCTGAGAATGCTTCTGTCTAGATTTTAACTGAAGACAATCCCGTTTCCACCGAAGCATTCTCAGAACCTTGCAAA | 25 | chr5:47,813,699-47,813,952 | Name: ALR/Alpha Family: centr Class: Satellite | TGTGTAAAGGATCGTTCAACTCT | 207 | CTTTGAGGATTTCGTGGGAAAC | 264 |

FIG. 1C

Table 1 continued

| | | | | | | | | | |
|---|---|---|---|---|---|---|---|---|---|
| Sepsis IC30 | Set2Ctl06 | hu-sep-CNAD-0026 | 224 | GGGGTTTCCACTTTGCATCTTGCTTATTTCTCTTGC CACTGCCAATTAAGAAGTGCCTTTTGGGCAGGGGTTG CAATCCTAGTCTCTGTATAAACAGACTTTAAACCAACA AAGATCAAAAGAGACAAAAGAAGGTCATTACATAATGG TAAAGGGATCAATTCAACAAGAAGAGCTAACTATCCT AAATATATGCACCCAATACAGAGGAGCACCCAGATTC | 26 | chrX:102,050,997-102,051,156 | Name: L1PA3<br>Family: L1<br>Class: LINE | TCTCTTGCCACTG CCAATTA | 208 | AATTGGGTGCTC CTGTATTG | 265 |
| Sepsis IC31 | Set2Ctl07 | hu-sep-CNAD-0027 | 199 | GAATAATGCCGCAATAAACATACGTGTGCATGTGTCT TTATAGCAGCATGATTTATAGTCCTTTGGGTATATACC CAGTAATGGGATGGCTGGGTATTACCCTAAAGGATTA TAAATCATGCTGCTATAAAGACACATGCACACGTATG TTTATTGCGCGGACACTATTCACAATAGCAAAGACTTGGA ACCAACCCAAATG | 27 | chr5:80,785,606-80,785,714 | Name: L1HS<br>Family: L1<br>Class: LINE | GAATAATGCCGC AATAAACATACG | 209 | TGGTTCCAAGTCT TTGCTATTG | 266 |
| Sepsis IC32 | Set2Ctl08 | hu-sep-CNAD-0028 | 151 | GTTTATAAAGTCTGCAAGTGGATATTCAGACCCCTTT GAGGCCTTCGTTGGAAACGGGATTTCTTCATATATG CTAGACAACGAACAATTCTCAGTAACTTCCTGTGTGT GTGTATTCAACTGACAGAGTTGAACGATCCTTTACCT GTC | 28 | chr5:48,558,291-48,558,436 | Name: ALR/Alpha<br>Family: centr<br>Class: Satellite | TCTGCAAGTGGA TATTCAGACC | 210 | GGATCGTTCAACT CTGTCAGTT | 267 |
| Sepsis IC33 | Set2Ctl09 | hu-sep-CNAD-0029 | 251 | GTGTTAAAGTCTCCATTAACGTGTGGGAGTCTA AGTCTCTTTGTAGGTCACTCAGGACTTGCTTTATGAAT CTGGGTGCTCCCTGTATTGGGTGCATATATATTAGGA TAGTTAGCTCTCTTCGTTGAATTGACATTCCCTTACCATT ATGTAAGACCCTCTTTCTCAAGATCTCATCAAATAAAC ACGAATGGTCAACCACAAGAAGAAAAGACTGGAGTCAT CATCATCCCACGACACAGACATTTCATC | 29 | chr18:4,651,025-4,651,191 | Name: L1P1<br>Family: L1<br>Class: LINE | CCCATTATTAACG TGTGGGAGT | 211 | AAATGTCTGTCTG GGCATGAT | 268 |
| Sepsis IC34 | Set2Ctl10 | hu-sep-CNAD-0030 | 221 | GTTTGGAAACACTCTCTGTCTAAAGTCTGCAAGCAGA TATTTGGATCTCTTTGAGCCCTTCGTTGGAAACGGGG TTCTTCATATATTATGCTAGACAAGAAGAATTCTCAGTAA CTTCCTGTGTTGTTGTTGAATTCACCACAGAGTTGAA CGATCCTTTGTGTATTCACACAGAAGCAGAGAATTGAAACACTCTTTT GTGGAATTTGCAAGTGGAGATTTCAACAAAAAAC | 30 | chr1:122,663,803-122,664,015 | | TGGAAACACTCT GTCTGTAAAGT | 212 | CTCCACTTGCAAA TTCCACAAA | 269 |
| Sepsis IC35 | Set2Ctl11 | hu-sep-CNAD-0031 | 171 | GCTCTGCGATGTGTGCGTTCAACTCTCAGAGTTTAAC TTTCTTTTCATTCAGCAGTTTGAAAACACTCTGTTTG TAAAGTCTGCACGTGGATAATTTGACCACTTAGAGGC CTTCGTTGCAGCGGATTCTTCCATATTCTGCTAGA CAGAAGAAGAATTCTCAGAATCTTC | 31 | chr5:49,090,702-49,090,872 | Name: ALR/Alpha<br>Family: centr<br>Class: Satellite | TCTGCGATGTGTG CGTTC | 213 | TCTGTCTAGCAGA ATATGAAGAAATC C | 270 |
| Sepsis IC36 | Set2Ctl12 | hu-sep-CNAD-0032 | 284 | AGTCTAAGCTCTCTTTGTAGGTCACTCAGGACTTGCTTT ATGAAATCTGGGTGCTCCTGTATTGGGTGCATATAT TTAGGATAGTTAGCTCTCTTCGTTGTTGAATTGATCCCTTT ACCATTATGTAAATGGCCTTGTCTCTTTTGCCTTGGTAG GGGTGTGTTTTGGTTTTTGTTTTCCATTTGCTTGGTAG ATCTTCCTCACGTGAGATGGGTTTCCTGAGTACGAGCACACT GATGGGTCTTGACTCTATCC | 32 | chr4:75,274,211-75,274,528 | Name: L1PA2<br>Family: L1<br>Class: LINE | GTCTCTTTGTAGG TCACTCAGG | 214 | GGATAGAGTCAA GACCCATCAG | 271 |

FIG. 1D

Table 1 continued

| | | | | | | | |
|---|---|---|---|---|---|---|---|
| Sepsis JC37 | Set2Ctl13 | hu-sep-CNAD-0033 | 234 | GTGTTAAAGTCTCCCATTATTGTTTGGGCGTCTAA GTCTCTTTGTAGGTTTCTAAGGATCTGCTTTATGAATC TAGGTGCTCCTGTATTGGGTCACATATATTTAGGAT AGTTAGCTCTTCCTTGTTGAATTGATCCCTTTACCATTA TGTAATGGCCTTCTTTGTCTCTTTGATCTTGTTGGT TTAAAGTCTGTTTTATCAGAGACTAGGATTGCAACCC CACACCAA | 33 | chr1:50,908,471-50,908,697 | Intron: FAF1 Description: Fas associated factor 1 Molecule type: mRNA RepeatMasker Information Name: L1PA5 (link requires registration) Family: L1 Class: LINE | CCATTATTATTGT TTGGGCGTCTAA G | 215 | GGTTGCAATCTA GTCTCTGATAAA | 272 |
| Sepsis JC38 | Set2Ctl14 | hu-sep-CNAD-0034 | 233 | GGTGGTGTGTGCGTTCAACTCACAGAGTTTAACCTTT CTTTTCATAGAGACAGTTAGGAAAACACTCTGTTTGTAAA CTCTGCAAGTGGATATTCAGACCTCTTTGAGGCCTTC GTTGGAAACGGGATTTTCTTCATACTGTGCTAGACAGA AGAATTCTCAGTAACTTCCTTGTGTGTGTATTCAA CTCAAAGAGGGTCTGAATATCCACTTGCAGAGTTTACA AACAGAGTG | 34 | chr1:123,429,735-123,429,930 | Name: ALR/Alpha Family: centr Class: Satellite | TGGTGTGTGCGTT CAACT | 216 | TCTGCAAGTGGAT ATTCAGACC | 273 |
| Sepsis JC39 | Set2Ctl15 | hu-sep-CNAD-0035 | 151 | GACTTGCTTTATGAATCTCGGGTGCTCCTGTATTGGGT GCATAAATATTTAGGATAGTTAGCTCCTCTTGTTGAAT TGATCCCTTTACCATTATGTAATGGCCTTCTTTGTCTC TTTTGATCTTTGTTGCTGGCCAGGCAATCAGGCAGG G | 35 | chr3:168,352,951-168,353,101 | Intron: EGFEM1P RefSeq: NR_021485.2 Status: Validated Description: EGF like and EMI domain containing 1, pseudogene Molecule type: misc_RNA RepeatMasker Information Name: L1P1 Family: L1 Class: LINE | | | | |
| Sepsis JC40 | Set2Ctl16 | hu-sep-CNAD-0036 | 225 | TTTGTCTAGCTTTGGAGGATTTCGTTGGAAACGGGATT ACATATAAAAAGCAGAGCGGCATTCCCAGAAACTT CTTTGTGATGTTTGCATTCAAGTCACAGACTTGAACAT TCCCCTTTCATAGAGACAGGTTTGAAACACTCTTTCTGTA GTATCTGGAAGTGAACATTAGGACAGCTTTCAGGTCT ATGGTGAAGAAAGGAAATATCTTCAAAAAAAAACCAAA C | 36 | chr2_Kl270715v1_random:144, 580-144,789 | Name: ALR/Alpha Family: centr Class: Satellite | TTTATGAATCTGG GTGCTCCTG | 217 | CCTGGCCAGCAAC AAAGA | 274 |
| | | | | | | | | TTTGTCTAGCTTT GAGGATTTCG | 218 | GAAGATATTTCCT TTCTCACCATAGA C | 275 |
| Sepsis JC41 | Set2Ctl17 | hu-sep-CNAD-0037 | 151 | GTTTGGTGGGGAATTCTTCTCTAGCCTTTATATGA AAAAAACCCGTTTCCAACCAAAGGCCTCAAAGAGGTCT GAATATCCACTTGCAGACTTTACAAACAGAGTGTTTC CTAACTGCTCTATGAAAAGAAAAGGTTAAACTCTGTGA GTT | 37 | chr19-27,183,600-27,183,741 | Name: ALR/Alpha Family: centr Class: Satellite | GGGAATTCTTCTG TCTAGCCTTAT | 219 | AGAGCAGTTAGG AAACACTCTG | 276 |

FIG. 1E

Table 1 continued

| | | | | | | | | | |
|---|---|---|---|---|---|---|---|---|---|
| Sepsis JC42 | Set2Ctl18 | hu-sep-CNAD-0038 | AGTTCAACCATTGTGGAAGACAGTGTTGACCAGCCA AAGGATCTAGAACTAGAAATACCCAAAGGATTATAAATGA TCCCATTACTGGGTATATACCCAAAGGATTATAAATGA TTCTACTATAAAGATACATGCAAAGACTGTATGTTATTGT AGCACTCTTCACATAGCAAAGACTGGGAACCAACCC AAATGCCCATCCAATCAATAATAGACTGGATAAAGAAAATGT GGCACATAGATACC | 238 | chr1:221,211,977-221,212,208 | Name: L1PA7 Family: L1 Class: LINE | | GTTCAACCATGT GGAAGACAG | 220 | CCAGTCTATTATT GATGGGCATTT | 277 |
| Sepsis JC43 | Set2Ctl20 | hu-sep-CNAD-0039 | ACCTTTGACTTCAAAGCGGCTGAAATCTCCACTTGCA AATTCCACAAAAAGAGTGTTACAAGTCTGTCTGTGT AAAGGATCGTTCAACTCTGTGAGTTGAATACACACA CACAAGGAAGTTACTGAGAATTCTTCTGTGTAGCCTT TGGTCAAATTATCCACGTGCAGACTTTACAACAGAG TGTTTCCAAACTGCTGAATGAAAAGAAAAGTTAAACTC TGAGAGTTGAACGCACACATCACAAAGGAG | 290 | chr5:48,017,517-48,017,801 | Name: ALR/Alpha Family: centr Class: Satellite | | GACTTCAAAGCG GCTGAAAT | 221 | CCTTTGTGATGTG TGCGTTC | 278 |
| Sepsis JC44 | Set2Ctl21 | hu-sep-CNAD-0040 | CCCATTATTATTGTGTGGGAGTCTAAGTCTCTTTATAG GTCTTCTAAGGACTTGCTTTATGAATCTGGGTGCTCCT GTGTTGGGTGTGTTTGGTTTTGTTGTTGAATTGATCCCT TTACCATTATGTAATGACAAAGAAGCGACCATTACATAAT GGTAAAGGGATCAATTCAACAAGAAGAGCTAACTATC CTAAATATATGCACCCAATACAGAGAGCACCCAGAT TCATAAAGCAAGTCCTTAG | 244 | chr18:80,234,747-80,234,868 | Intron PARD6G RefSeq: NM_032510.3 Status: Validated Description: par-6 family cell polarity regulator gamma Molecule type: mRNA RepeatMasker Information Name: L1PA4 Family: L1 Class: LINE | | CCCATTATTATTG TGTGGGAGTCTA | 222 | AATCTGGGTGCTC CTGTATTG | 279 |
| Sepsis JC45 | Set2Ctl22 | hu-sep-CNAD-0041 | GGATTATTCCATTCCATTAGATGATTCCATTCG GGTCCATTCGATGATTCCTCGCGATTCCATTCCATTCGATAAT CCGTTTTTTCCGTTTGATGTTGATTCCATTCGATTC CATTCGATGATAATTCCATTCGATTCTATGCGATGAT | 151 | chr1:143,265,810-143,265,960 | | | GATGATTCCATTC GGGTCCA | 223 | TCGAATCAACATC AAACGGAAA | 280 |
| Sepsis JC46 | Set2Ctl23 | hu-sep-CNAD-0042 | GGATCGTTCAACTCTGTGAGTTGAATACACACACAC AAGGAAGTTACTGAGAATTCTTCTGTCTAGCAGAATAT GAAGAAATCCCGTTTCAAGCAAGGCCTCAAAGGGG TCTAACTAATCACGTGCAGACTTTACAGACAGAGTCTT TCCAAACTGCTCTATGAAGAA | 172 | chrUn_KI270303v1:1,266-1,488 | Name: ALR/Alpha Family: centr Class: Satellite | | GAGTTGAATACA CACAACACAAGG | 224 | TCTTCATGAGAGCA GTTTGGAAAGA | 281 |
| Sepsis JC47 | Set2Ctl24 | hu-sep-CNAD-0043 | GACGTTTCTGAGAATGCTTCTGTCTGATATTTGATATGA AGATATTCCCGTTTCCAACGAAAATCTCAAATCTATCC AAATGTCCACTTGCAGATTCAACAACAAAAGTGTTTTCA GAACTGCTCTATCAAAAGAATGGATCAACACTGTTAG TTTGAGTACCCACATCACAAACGTGATTCTTTGCCATG TTTGCATTCAACTACATAGAGTTGAACATTCCCTTTGAG AG | 228 | chr21:11,497,251-11,497,422 | Name: ALR/Alpha Family: centr Class: Satellite | | CGTTTCTGAGAAT GCTTCTGTC | 225 | CTTCAAAGGGAA TGTTCAACTC | 282 |
| Sepsis JC48 | Set2Ctl25 | hu-sep-CNAD-0044 | GAATCGAATGGAATCATCGAATCGAATGGAAT AATCATTGAACGGAATCGAATGGAATCATCATCGGAT GGAAATGAATGAATCATCATCGAATGGAATCGAATA GAATTATGGAATGAAATCGAACTCCAGTGATCATCGAA TGG | 151 | chr1:125,182,565-125,182,715 | Name: (ATTCCATTCG)n Family: Simple_repeat Class: Simple_repeat | | TCGAATGGACTC GAATGGAATAA | 226 | TCGATGATGATCA CACTGGATTT | 283 |

FIG. 1F

Table 1 continued

| | | | | | | | | |
|---|---|---|---|---|---|---|---|---|
| Sepsis JC49 | Set2Cct26 | hu-sep-CNAD-0045 | 274 | AACATTCCGTTTCAGAGAGCAGCCACTCTT TTTGTAGTATGTGCAAGCTGGATATTTGAGCGCTCTG AGGCCTACGGTGAAAACATTCTCAGAAACTTCCCATAACC TATGCACTCCACCTAACAGAAAAGTCCACTTCCATATAC TACAAAAAGAGCGTTTCAAACCTGCTCTATGAAAGGC AATGTTCAACTCTGTGACTTGAATGCAGAACACAG AGCCAGTTTCTGAGA | 45 | chr22:14,171,314-14,171,509 | Name: ALR/Alpha Family: centr Class: Satellite | ACATTCCGTTCA GAGAGCAG | 227 | TCTGTGATGTCTG CATTCAAGT | 284 |
| Sepsis JC50 | Set2Cct27 | hu-sep-CNAD-0046 | 245 | AGATATAGAAAAGGCCTTTGACAAATTCAACAACTCT TCATGCTATAAACTCTCAGTAAATTAGGTATGGATGG GAAATATCTCAAAATAATAGGAGCTATCTATGACAAAC AGCAGCAATATCACTACTGAATGGGCAAAAACTGGG AGCATTCCCTTGAAAACTGGCACAAGACAGGGATGG CCTCTCTCACCACTCCTATTCAACATAGTGTTGGAAG TTCTGGGCAGGGCAATTAGGC | 46 | chrX:33,442,220-33,442,459 | Name: L1PA4 Family: L1 Class: LINE | CAAACAACTCTCA TGCTATAAACTCT C | 228 | GGCCAGAACTTCC AACACTAT | 285 |
| Sepsis JC51 | Set2Cct28 | hu-sep-CNAD-0047 | 151 | ATTCATTTCCATCCGATGAATGATTCCATTCGATTCCGT TCAATGATTATTCCATTCGAGTGATTCCATTCCGATTCA TTCGATTCCATTCGATGATGATTCGATTCCGAGTCCAT GGATTATTCCATTCCATTCCATTAGATGATTCCATTCG | 47 | chr1:143,232,400-143,232,550 | Name: (ATCGAATGGA)n Family: Simple_repeat Class: Simple_repeat | TCCATCCGATGAT GATTCCAT | 229 | GGAATAATCCATG GACTCGAATG | 286 |
| Sepsis JC52 | Set2Cct29 | hu-sep-CNAD-0048 | 151 | AAGAAATTTTCTGAGAATGATTCTCTGCTGGTTTCTTCCT ATAGAAACTACAGAATGATTCTCAGAACTCCTTTG TGATGTGCGTTCAACTCACATAGTTAACCTTTCTT TTCATAGAGCAGTTTGGAAACACTCTGTTTGTAAAGT | 48 | chr5:48,164,599-48,164,718 | Name: ALR/Alpha Family: centr Class: Satellite | ATGAATTCTGTCTG GTTCTTCCT | 230 | ACAAACAGAGTGT TTCCAAACTG | 287 |
| Sepsis SC1 | HSMC1 | hu-sep-CNAD-0049 | 195 | TCAACACCACCTTCTTCGACCCCGCCGGAGGAGGAG ACCCATTCTATACCAACACACCTATTCTGATTTTCGT CACCCTGAAGTTTATATTCTTATCCTACCAGGCTTCG GAATAATCTCCCATATTGTAACTTACTACTCCGAAAA AAAGAACCATTTGGAATACATAGGTATGGTCTGAGCTA TGATATCAATTGGC | 49 | MT:6547 - 6746 | MT-CO1 Cytochrome c oxidase | TCAACACCACCTT CTTCGAC | 231 | TTGATATCATAGC TCAGACCATACC | 288 |
| Sepsis SC2 | HSMC2 | hu-sep-CNAD-0050 | 186 | GTGGATATTCGGAGACCTCTTTGAGCCCTTCGGTTGAAAA CGGGATTCTTCCATATTATGCTAGAACAGAAGATTTCTC AGTAACTTCTTTGCGTTGCTGTATGCAACTCACAGA GTTCAAACCTTCCTTAGACAGAGACAGTTTGAAACAC TCTTTTTGTGAAATTTGCAAGTGGAGATTTCAAGCGC TTCGATGCCAATGG | 50 | 16:36853542 - 36853741 | Name: ALR/Alpha Family: centr Class: Satellite | GTGGATATTCGG ACCTCTTGA | 232 | GCGCTTGAAATCT CCACTTG | 289 |
| Sepsis SC3 | HSMC4 | hu-sep-CNAD-0051 | 194 | GAACCATTTGGATACATAGGTATGGTCTGAGCTATGA TATCAATTGGCTTCCTAGGGTTTATCGTGTGAGCACA CCATATATTCACTTCCGCTACCTACCTAATCATCGCTATCC GCACCGGCGCTAAGTTATTTAGCTGACTCGCCACACT CCACGGAAGCAATAT | 51 | 1:631870 - 632069 | | ATTTGGATACATA GGTATGGTCTGA G | 233 | TATTGCTTCCGTG GAGTGTG | 290 |
| Sepsis SC4 | HSMC5 | hu-sep-CNAD-0052 | 150 | ACAGAACAGGGCTCCTCTAGAGGGATATGAAGCACCG CCAGGTCCTCTTTGAGTTTTAAGCTGTGCCTCGTAGTGT TGGGCGAGCAGTTTTGTTGATTTAACTGTTGAGGTTT AGGGCTAAGCATAGTGGGG ATCTAATCCCAAGTTTGG GT | 52 | 13:109424100 - 109424299 | | ACAGAACAGGCT CCTCTA | 234 | ACCCAAACTGGGA TTAGATAC | 291 |
| Sepsis SC5 | HMSC7 | hu-sep-CNAD-0053 | 180 | CAATAACTTGACCAACGAACAAGTTACCCTAGGGAT AACAGCGCAATCCTATTCTAGAGTCCATATCAACAATA GGGTTTACGACCTCGATGTTGGATCAGGACATCCCGA TGGTGCAGCCGCTATTAAAGGTTCGTTTGTTCAACGA TTAAAGTCCTACGTGATCTGAGTTCAGACCGGAGTAA TCCAAGGTCGGTTTC | 53 | MT:2900 - 3099 | MT-RNR2 mitochondrially encoded 16S RNA | CCAACGGAACAA GTTACCCTA | 235 | CTGGATTACTCCG GTCTGAAC | 292 |

FIG. 1G

Table 1 continued

| | | | | | | | |
|---|---|---|---|---|---|---|---|
| Sepsis SC6 | HSMC8 | hu-sep-CNAD-0054 | 180 | CAACTAGGACTCATAATAGTTACAATCGGCATCAACC AACCACACCTAGCATTCCTGCACATCTGTACCCACGC CTTCTTCAAAGCCATACTATTTATGTGCTCCGGGTCC ATCATCCACAACCTTAACAATGAACAAGATATTCGAAAA AATAGGAGGACTACTCAAAACCATACCTCTCACTTCA ACCTCCCTCACCAT | 54 | MT:13261 - 13460 | MT-ND5 mitochondrial membrane respiratory chain NADH dehydrogenase (Complex I) | GTTACAATCGGC ATCAACCAAC | 236 | GGTGAGGGAGGT TGAAGTG | 293 |
| Sepsis SC7 | HSMC14 | hu-sep-CNAD-0055 | 162 | CTGGCATTTTGTAGATGTGGTTTGACTATTTCTGTATG TCTCCATCTATTGATGAGGGTCTTACTCTTTTAGTATA AATAGTACCGTTAACTTCCAATTAACTAGTTTTGACAA CATTCAAAAAGAGTAATAAACTTCGCCTTTAATTTTAA TAATCAACACACCCCTCCTAGCCTTACTACTAATAATTATT ACATTTTGAC | 55 | MT:9929 - 10128 | MT-CO3 Cytochrome c oxidase subunit 3 | GTAGATGTGGTTT GACTATTTCTGTA TG | 237 | GGCTAGGAGGGT GTTGATTATT | 294 |
| Sepsis SC8 | HSMC15 | hu-sep-CNAD-0056 | 167 | AATCATTTTATTGCCACAACTAACCTCCTCGGACTCC TGCCTCACTCATTACACCACAACCACCCAACTATCTATA AACCTAGCCATGGCCATCCCCTTATGAGCGGGCGCA GTGATTATAGGCTTTCGCTCTAAGATTAAAAATGCCCT AGCCCCACTTCTTACCACAAGGCACACCTACACCCTT ATCCCTATACTAG | 56 | 1:633920 - 634119 | | ATTGCCACAACTA ACCTCCTC | 238 | GGTGTGCCTTGTG GTAAGAA | 295 |
| Sepsis SC9 | HSMC18 | hu-sep-CNAD-0057 | 180 | TATTCGAGCCGAGCTGGGCCAGCCAGGCAACCTTCT AGGTAACGACCACACTCTACAACGTTATCGTCACGCC CATGCATTTGTAATATCTTCTTCATAGTAATACCCAT CATAATCGGAGGCTTTGGCAACTGACTAGTTCCCCTA ATAATCCGGTGCCCCGATATGGCGTTTCCCCGATAA ACAACATAAGCTTCT | 57 | MT:6011 - 6210 | MT-CO1 Cytochrome c oxidase | AGCCAGGCAACC TTCTA | 239 | AGAAGCTTATGTT GTTTATGCG | 296 |

FIG. 1H

Table 2

| Final motif ID | Interim motif ID | Patent ID | Length (bp) | Sequence | SEQ ID NO: | Locus | Annotation | Fwd Primer | SEQ ID NO: | rev Primer | SEQ ID NO: |
|---|---|---|---|---|---|---|---|---|---|---|---|
| Sepsis.iU1 | SetLRef01 | hu-sep-CMAD-0058 | 218 | ATATTCTGTTGATTTGGGGTGGAGAGCTGGAGTTCAATGCTCTATTAAGGTCCACTTGGTGCAGAGCTGAGTTCAATTCCTGGGTATCCTTGTTGACTTTCTGTCTCATTGAATCTGTCTAATGTTGACAGTGGGGTGTTAAAGTCTCCCATTATTAATGTATGGAGGTCTAAGCTCTCTTTGTAGATCACTCAGGACTTGCTTTATGAATCTGGGTGCTGCTG | 58 | chr16:55,601,126-55,601,343 | Name: L1PA3 Family: L1 Class: LINE | GGGTGGAGAGTTCTGTAG ATGT | 297 | CAGGAGCACCCAGATT CATAAAG | 333 |
| Sepsis.iU2 | SetLRef02 | hu-sep-CMAD-0059 | 256 | ATATGAACTTTAAAGTAGTTTTTCCAATTCTGTGAAGAAAGTCATTGGTAGCTTCATGCGGGATGGCATTGAATCATAAATTACCTTGGGCAGTATGGCCATTTTCATGATATTGAATTCTCCTATCCATGAAGCATGGAATGTTCCATTTGTTTTGTGTCCTCTTTTATTTCATTGAGCAGTGGGTTCGTAGTTCTCCTTGAAGAGTCCTTGCACATCCCTTGTAAGGTGGAATTCCTAGGTATTTTATTCCTGAAACG | 59 | chr6:40,091,882-40,092,137 | Name: L1PA5 Family: L1 Class: LINE | TCCAATTCTGTGAAGAAA GTCATTG | 298 | AAATTACCTAGGAATCC ACCTTACAA | 334 |
| Sepsis.iU3 | SetLRef03 | hu-sep-CMAD-0060 | 249 | AGAGAATAAAATACCTAGGAATCCAACTTACAAGGCATGTGAAGAGGACCTCTTCAAGGGAGAACTACAAACTGCTACTCAAGGGAAATAGAAGAAGGACTACAAACAAATGGAAGAAATATTCCAATGCTCATGGGATAGGAAGAATCAATATGGTGAAAAAATGGCCATACTGGCCAAGGTAATTTACAGAATTCAATGCCATCGCCAAGCTACCAATGACCTTTCTTCACAGAATTGGAAAAAAACTACTTTAAAG | 60 | chr4:97,637,753-97,638,000 | Intron: STPG2 Description: Homo sapiens sperm tail PG-rich repeat containing 2 (STPG2), mRNA. (from RefSeq NM_174952) Gencode Transcript: ENST00000295268.3 Gencode Gene: ENSG00000163116.9 RepeatMasker Information Name: L1PA3 Family: L1 Class: LINE | ACCTAGGAATCCAACTTAC AAGG | 299 | TCCAATTCTGTGAAGA AAGTCATTG | 335 |
| Sepsis.iU4 | SetLRef04 | hu-sep-CMAD-0061 | 277 | ACCTTGGGCAGTATGGCCAGTTTTTCCAAGGATATATTGAATTCTTCCTACCCATGAGCATGGAATTTCTTCCATTTGTTTTGTATCCTCTTTTATTTCACTGAGCAGTGGGTTTGTAGTTCTCCTTGAAGAGGTCCTTCACATCCCTTGTAAGTTGGAATTCCTAGGTATTTTATTCTTCTTTGAAGCAATTGTGAATGGCAGTTCACTCATGATGGCTCTCTGTCTGTGTGGTGTATAAGAATGCTTGTGATTTTTGTACATTGATTTTGTATCCTGAGAC | 61 | chr6:124,708,424-124,708,700 | Intron: NKAIN2 Description: Homo sapiens Na+/K+ transporting ATPase interacting 2 (NKAIN2), transcript variant 3, mRNA. (from RefSeq NM_001302737) RepeatMasker Information Name: L1PA2 (link requires registration) Family: L1 Class: LINE | ACCTTGGGCAGTATGGC | 300 | GCATTCTTATACACGAA CAACAGA | 336 |
| Sepsis.iU5 | SetLRef05 | hu-sep-CMAD-0062 | 232 | CCTATTCAACATAATCTTCGAACTTCTCACCCAGGAGACAATCAGGCAGGAGAAACAAATAATCTTGGGCAAGCTACTCAATTAGGAAAAAAGAGGAAAGTCAAAATTGTCCCTGTATGCAGATAACATGATTGTATATTTAGAAAAACCCCATCATCCAGCCCAAAATCTCCTTAAGCTGATAAGCCAACTTCAGCAAAGTCTCAGGATACAAAATCAATGTGCAAAAATCACAAGCATTCCTATAC | 62 | chr8:132,599,894-132,600,121 | Intron: LR4C6 Description: leucine rich repeat containing 6 (from HGNC LRRC6) RefSeq Summary (NR_073525): The protein encoded by this gene contains several leucine-rich repeat domains and appears to be involved in the motility of cilia. Defects in this gene are a cause of primary ciliary dyskinesia-19 (CILD19). Alternative splicing of this gene results in multiple transcript variants. Related pseudogenes have been identified on chromosomes 4, 11 and 22. [provided by RefSeq, Apr 2016]. RepeatMasker Information Name: L1PA5 Family: L1 Class: LINE | ACATAATGTTGGAAGTTCT AGCCA | 301 | TTGTATCCTGAGACTTT GCTGAAAG | 337 |

FIG. 2A

Table 2 continued

| | | | | | | | | |
|---|---|---|---|---|---|---|---|---|
| Sepsis IU6 | SetIRef07 | hu-sep-CNAD-0063 | 270 | CTTTAAAGTAGTTTTTTCCAATTCTGTGAAGAAAGTCATTGGTAGCTT GATGGGGAATGGCATTGGAATCTTCCTATCCATGAGCATGGAATGTTCTTCC ATTTGTTTGTGTCCTCTTTATTTGTGAACAGTGGTTTGTAGTTTT CCTTGAAAAGGTGCTTCGCATTCCTTGTAAGTTGGATTCCTAGATAT TTTATTCTCTTTGTAGCAATTGTGAATGGGAG | 63 | chr21,27,521,783-27,522,043 | Name: L1PA6 Family: L1 Class: LINE | CTCCCATTCACAATTGC TACAAA | 338 |
| Sepsis IU7 | SetIRef10 | hu-sep-CNAD-0064 | 210 | ATGTTCTTCGACATTTGTTGTCTCCTCTTTATTTCCTTGAGCAGTGGT TTGTAGTTCTCCTTGAAGAGGTCCTTCACATCCCTTGTAAGTTCGAT TCCTAGGTATTTTATTCTCTTTGAAGAATTCTGAAGTGGGAGTTCACC CATGATTTGGCTCTCGTCTTGTCTGTTGGTGTATAAGAATGCTT GTGATTTTTGTACATTGAT | 64 | chrX,81,845,334-81,845,543 | Name: L1H5 Family: L1 Class: LINE | GTTCTTCCATTGTTTGTCT CCTC | 339 |
| Sepsis IU8 | SetIRef11 | hu-sep-CNAD-0065 | 206 | CACAATAATAAATGGGAGAACTTTAACACCCCACTGTCAACATTAGACA GATCAAATGAGACAAGAGAAAAGTTAACAGGATACCCAGGAATTGAACTCA GCTCTGCACCAAGCAGACAGAACCAATGACATCTACAGAACTCTCACCC CAAATCAACAACAATAATACAATCTTTTTCATCACCAACCCTATTGCAAAA TTGACCACATAGTTGGA | 65 | chr9,26,446,085-26,446,290 | Name: L1PA3 Family: L1 Class: LINE | CACAATAATAATGGGAGA CTTTAACACC | 340 |
| Sepsis IU9 | SetIRef12 | | | CTGTGATCGTGAGAGCCTGTTGTTATGAATTTCTGTTCTTTCCATTTG CTGAACGAGTGTTTTGCTTCCAATTATGTGGTTGATTTTAGAATAAGTG CTATGTGGTGCTGAACAAGAATATATATCTTGTGATTTGGGGTGAG AGTTCTGTAGAATGTCTATTAGGTCCACTTCGGTGCAGAGCTGAGTTCA ATTCCTGGATATCCTTGTTAACTTTCTGTCTCGTTCGATCTGTCTAATG TTGAC | 66 | | Description: The sequence shown here is derived from an Ensembl automatic analysis pipeline and should be considered as preliminary data. (from UniProt C9JR35G) RefSeq Summary [NM_001242643]: The protein encoded by this gene is a member of the phosphatase and actin regulator family of proteins. This family member can bind actin and regulate the reorganization of the actin cytoskeleton. It plays a role in tubule formation and in endothelial cell survival. Polymorphisms in this gene are associated with susceptibility to myocardial infarction, coronary artery disease and cervical artery dissection. Alternative splicing of this gene results in multiple transcript variants. [provided by RefSeq, Apr 2016]. RepeatMasker Information | | 243 | chr12,743,727-12,743,969 | | ATGTGAGAGCCTGTTGTT ATGA | 341 | TCAACATTAGACAGAT CAACGAGA |
| Sepsis IU10 | SetIRef13 | hu-sep-CNAD-0067 | 213 | TGCCATCCCCATCCAAGCTACCAATGACTTTCTTCACAGAATTGGAAA AAACTACTTTAAAGTTCATATGGAACCAAAAAGAAGAGCCTGCATTGCC AAGTCAATCCTTAAGCCAAAAACAAAGCAACAAAAGCTGGAAGGCATCATCTGCTACC TGACTTCAAACTATAACCTAACAAGAATTACAGTAACCAAAACAGCATGGTA CTGGTACCAAAACAGAGATATAGA | 67 | chr5,180,758,034-180,758,246 | Name: L1PA4 Family: L1 Class: LINE | CCCATCAAGCTACCAATGA CT | 342 | GGTACCAGTACCATGC TGTTT |
| Sepsis IU11 | SetIRef15 | hu-sep-CNAD-0068 | 193 | TTTTTGGTATCAGATACATGCTCTGTTTTGGTTACTGTAGCCTTGTAGTAT AGTTTGAAGTCAGGTAGCGTGAGTGCCTGACATGCCTCCTGTCTTTTGGCT TAGGATTGACTTGGCGATGCGGGCTCTTTTTGTTCCATATGAAACT TTAAGTAGTTTTTCCAGTTCTGTGAACAAAGTCATTGGTAGCTT | 68 | chr2,210,760,331-210,760,518 | Name: L1PA3 Family: L1 Class: LINE | TGGTATACAGTACCATGCTG TTT | 343 | GCTACCAATGACTTTCT TCACAG |
| Sepsis IU12 | SetIRef16 | hu-sep-CNAD-0069 | 262 | CCTGTAGCCTTGTAGTAGTTTAGGATTGGCTTAGGGATTGACTTTGGGTGCCTCCG GCTTTGTTCTTTTTTGGCTTAAAGTAGTTTTTCCAATTCTGTGAAGAA AGTCATTGGTAGCTTTGATGGGATGGCATTGAATCTATAAATTACCT TGGGCAGTATGGCCATTTTCACGATATTGAATTCTTCCTATCCATGAG CATGGAATGTTCTTCCATTCTTTGTT | 69 | chr1,83,340,427-83,340,688 | Name: L1PA2 Family: L1 Class: LINE | TGTTAGCCTTGTAGTAAGT TTGAAGTC | 344 | ATGGAAGAACATTCCA TGCTCA |

FIG. 2B

Table 2 continued

| | | | | | | | | |
|---|---|---|---|---|---|---|---|---|
| Sepsis.IU13 | Set2Ref01 | hu-sep-CNAD-0070 | 191 | AAATAAAAGAAGAACACAAATAAATGGAAGAACATTCCATACTCGTCG ATAGGAAGAATCAATATTGTGAAAATGGCATACTCCCCAAGGTAAT TTATAGATTCAATGCCATCCCCATCAAGCTACCAACTGACTTTCTCAC AGAAATTGGAAAAACTACTTTAAAGTTCATATGGAACCAAAAAACAGC C | chr7:104,588,599-104,588,789 | Description: The sequence shown here is derived from an Ensembl automatic analysis pipeline and should be considered as preliminary data. (from UniProt C9JAS2) RefSeq Summary (NM_199050): This gene is a member of the lipoma HMGIC fusion partner (LHFP) gene family, which is a subset of the superfamily of tetraspan transmembrane protein encoding genes. Mutations in one LHFP-like gene result in deafness in humans and mice, and a second LHFP-like gene is fused to a high-mobility group gene in a translocation-associated lipoma. A partial gene fragment named LHFPL4 corresponds to a portion of the first exon of this gene. [provided by RefSeq, Jul 2008]. ##Evidence-Data-START## Transcript exon combination :: AY260763.1, SRR1660809.247031.1 | AATGGAAGAACATTCCAT ACTCGT | TCCAATTCTGTGAAGA AAGTCATTG | 345 |
| Sepsis.IU14 | Set2Ref02 | hu-sep-CNAD-0071 | 247 | CCCTCTCTCACCCACTCCAATCTAGTATTGGAAGTTCTGGCCA CAGCAATCACGCAAGAAGAAGAAATAAAGAGTATTCAAGTAGGAAAA GAGGAAGTCAAATTGTCCCTGTTTGCAGATGAACTGATTGTATATCT AGAAAACCCCATCATCTCAGGATACAAAATCAATGTGCAAAAATCACAA ACTTCAGCAAAGTCTCAGGATACAAAATCAAATGTGCAAAAATCACACAA GCATTCCTATAC | chr16:23,097,925-23,098,171 | Name: L1P2 Family: L1 Class: LINE | TCTCTCACCACTGCCATC A | TTGTATCCTGAGACTTT GCTGAAG | 346 |
| Sepsis.IU15 | Set2Ref03 | hu-sep-CNAD-0072 | 199 | ATAAGCAACTTCAGCAAAGTCTCAGGACAACAAATCAATGTACAAAA ATCACAAGCATTCTTATACACCAATAACGACAAACAGAGAGCCAAA TCATGAGTGAACTCCCAATTCACAAGTTGCTTCAAAAGAATAAAATACT TAGGAATCCAACTTACAAGGACGTGAAGGACCTCTTCAAGGAGAA CTACAAACCAC | chr15_KI270805v1_alt:132,156-132,354 | Name: L1PA3 Family: L1 Class: LINE | AGCAACTTCAGCAAAGTCT CA | CTTGAAGAGGTCCTTC ACGTC | 347 |
| Sepsis.IU16 | Set2Ref04 | hu-sep-CNAD-0073 | 279 | CTCTTTTTGGTACAAGTACCATGCTGTTTGGTTACTGTAGCCTTGT AGTATAGTTTGAAGTTCAAGTCAGCATGATGCCTCCAGCTTTGTTCTT TTACTTAGCATTGCTTGGCAATGTGTCGTGTTTTCGTTCGTTCCATATG GACTTTAAAGTAGTTTTTCCAATTCTGTGAAGAAAGTCATTGGTAGC TTGATGGGATGGCATTGAAATCTATAAATTACCTGGGCAGTATGGC CATTTTCATGATATATTGATTCTTCCTATCCATGAGCATGGAA | chr15:54,948,582-54,948,860 | Name: L1PA6 Family: L1 Class: LINE | GGTACAAGTACCATGCTG TT | GCTCATGGATAGGAAG AATCAA | 348 |
| Sepsis.IU17 | Set2Ref05 | hu-sep-CNAD-0074 | 282 | ATAAGAATGCTTGTGATTTTGCACAATTGATTTTGTATCCTGAGACTTT GCCTGAAGTTGCCTTATCAGCTTAAGGAGATTTGGGCTGAGACGATG GGGTTTCTAGATATACAATCATGTCATCTGCAAACAGCGACAATTG GACTTCCTCTTTTGCCTAATTGAAATACCCTTTATTCCCTTCCCTGTTTC ATTGCCCTGGTGCCCAGAACTTCCAACACTATGTTGAACAGGAGTGGTGA GAGAGGGTCTGCGTGTTGTGCCACGCTTTCAAAGGGAATGCTT | chr15:20,033,752-20,034,028 | Name: L1PA4 Family: L1 Class: LINE | TTGTATCCTGAGACTTTGC TGAA | AAGCATTCCCTTTGAA AGCTG | 349 |
| Sepsis.IU18 | Set2Ref06 | hu-sep-CNAD-0075 | 253 | TTTGATTGCACTGTGTCTGAGAGACAGTTGGTTGTGATTTCTGTTC TTTTACATTAAATGTGCTGAGGAGTGCTTTACTTCCAACTATCGGTAGTTT GGAATCAAATCTGTGTGCTGCTCGAAAAAAATGTATATCTGTTGATT TGGGGTGGAGAGTTCATCCTGTAGATGTCTATTAGGCTGCTTGGTGCAG AGCTGAGTTCAATTCCTGCAGGTATCCTTGTTGACTTTCTGTCTCGTTG ATCGTGTCTAATGTTGAC | chr7:43,061,531-43,061,783 | Name: L1PA2 Family: L1 Class: LINE | TGATTGCACTGTGTCTGA G | AGACAGATCAACGAAG CAGAAAG | 350 |

Table 2 continued

| | | | | | | | | |
|---|---|---|---|---|---|---|---|---|
| Sepsis SU16 | HRCF05 | hu-sep-CNAD-0092 | TCACAAAGCAGATTCTGATAATGCTTCTGTCTAATTTTTATATAAAGA TATTCCTGTTTCCAATGAAATCCTCAAAGCTATTCAAATATCCACTTG CAGATTATACAAAAACCGTGTTTCAAAACTACCAAAATAAATGTTCAA CTCTGTTCTTTGAGTACACTCATCATAAACAAGTTTCTGAGAAGGCTT CTGTCAAT | 92 | 16:34619874 - 34620073 | 170 | Name: ALR/Alpha Family: centr Class: Satellite | TCACAAAGCAGATTCTGAT AATGC | 331 | ATGATGAGTGTACTCA AAGAACAGA | 367 |
| Sepsis SU17 | HRCF06 | hu-sep-CNAD-0093 | GTTTCAAAACTGCTCTATGAAACGAATGTTCAACCCTGTGACGTGAA TGCAGACATCACAAAGCAGTTTCTGAGAATGCTTCTGTCTCGATTTT ACATGAAGATATTCCCGTTTCCAAAGAAATCTTCAAAGTTATCCAAAT ATCCACTTGCAGATTCTACAAAAAGAGTGTTTCCAAACTGCTGTATCA AAAGAAAAGGT | 93 | 18:20822641 - 20822840 | 182 | Name: ALR/Alpha Family: centr Class: Satellite | CTGCTCTATGAAACGAATG TTCAA | 332 | TTGATACAGCAGTTTG GAAACAC | 368 |

FIG. 2F

Table 3

| Final motif ID | Interim motif ID | Patent ID | Length (bp) | Sequence | SEQ ID NO: | Locus | Annotation | fwd Primer | SEQ ID NO: | rev Primer | SEQ ID NO: |
|---|---|---|---|---|---|---|---|---|---|---|---|
| Sepsis_J1 | Set1Dis01 | hu-sep-CNAD-0094 | 212 | GCACACGTATGTTTATCGCAGCACTACTCACAACAACAAAGACTTGGAACCAACCAAATGTCCACCAAATGATAGACTGGATTAAGAAAATGTGGCACATATACACCATGGAATACTATGCAGCCATAAAAAATGATGAGTTCATGTCCTTTGTAGGGACATGGATGAAGCTGGAAACCATCATTCTCAGCAAACTATTGCAAGGACAAAAA | 94 | chr2:56,600,561-56,600,772 | Name: L1PA4 Family: L1 Class: LINE | GCAACACGTATGTTTATCGCA | 369 | TTGTCCTTGCAATAGTTTGCT | 424 |
| Sepsis_J2 | Set1Dis02 | hu-sep-CNAD-0095 | 270 | TTTTTTTGAGACGGAGTCTCGCTCTGTCGCCCAGGCTGGAGTGCAGTGGCGCAATCTCGGCTCACTGCAAGCTCCGCCTCCCGGGTTCAAGCGCCATTCTCCTGCCTCAGCTTCCCAAGTAGCTGGGACTACAGGCGCCCGACCATCACGGCGGCTAATTTTTTGTATTTTTAGTAGAGACGGGGTTTCACCGTTTTAGCCGGGATGGTCTCGATCTCCTGACCTCGTGATCCGCCGCCTCGGCCTCCCAAAGTGCTGGGATTATAGG | 95 | chr4:112,548,854-112,549,122 | Name: AluYa5 Family: Alu Class: SINE | | | | |
| Sepsis_J3 | Set1Dis03 | hu-sep-CNAD-0096 | 135 | CATGTGTCTTTATAGCAGCATGATTTATAATCTTTGGGTATATACCCAGTAATGGATGGCTGGGGTCAAATGGTATTTCTAGTTCTAGAATCCTTGAGGAAATTGCCACACTGTCTTCCACACTGGGTTGAACTAGT | 96 | chr8:97,429,349-97,429,483 | Name: L1PA5 Family: L1 Class: LINE | CATGTGTCTTATAGCAGCATGATT | 370 | CCTATAATCCAGCACTTTGGG | 425 |
| Sepsis_J4 | Set1Dis04 | hu-sep-CNAD-0097 | 273 | TGTGTCCATGTGTTCTCATTGTTCGATTCCCACCTATGAAGTGAGAATATGATGGTTTGGTTTTTGTCCTTGTGATAGTTTGCTGTGAACTTCATCATTTTTATGGCTCACAGCTCCCATGTCCCACAAGGACATATGTGCCACATTTTGTTAATCCAGTCTATCATTGTTGGACATTTGGGTTGGTTCCAAGTCTTTGCTATGTGAATAATGCCGCAATAAACATACGTGTGCA | 97 | chrX:81,972,729-81,973,002 | Name: L1PA3 Family: L1 Class: LINE | GTGTCCATGTGTTCTCATTGTTC | 371 | TAGTTCAACCAGTGTGGAAGAC | 426 |
| Sepsis_J5 | Set1Dis05 | hu-sep-CNAD-0098 | 164 | TCCCACAGAATAATAATGGGAGAATTTGAATACGCCACTGTCAACATTAGAACAGATCAACGAGACAGAAAAGTTAACAAGGATATCCAGGAATTGAACTCAGCACTGCACCAAGCAGACCTAATAGACATCTACAGAACTCTCCACACAAATCAACAGAATATAC | 98 | chr5:130,522,657-130,522,814 | Name: L1PA5 Family: L1 Class: LINE | | 372 | CACGTATGTTTATTGCGGCAT | 427 |
| Sepsis_J6 | Set1Dis06 | hu-sep-CNAD-0099 | 102 | TGGCTGGTACCAGTTGTTCCTTCCATGTTTAGTGCTTCCTTCAGGAGCTCTTTTAGGGCAGGGCCTGGTGGTGACAAAATCTCTCAGCATTTGCTTGTCTGT | 99 | chrX:16,323,570-16,323,671 | Name: L1PA3 Family: L1 Class: LINE | TCCCACAGAATAATAATGGGAGAAT | 373 | TCTGTTGATTTGGTGTGTGGAGAG | 428 |
| Sepsis_J7 | Set1Dis07 | hu-sep-CNAD-0100 | 232 | TTTTTTTGGAATAGTTTACTGAGAATGATGTTTTCCAATTTCATGTCCCTACAAAGGACATGGAAACTCATCATTTTTTATGGCTCCATGATATTCCATGGTGTATATGTGCCACATTTTCTTAATCCAGTCTATCATTGTTGGACATTTGGGTTGCTTCCAAGTCTTTGCTATTGTGAATAATGCCGCAATAAACATACGTGTGCATGTGTCTTTAGAGCAGCATGAT | 100 | chrX:125,043,686-125,043,920 | Name: L1PA2 Family: L1 Class: LINE | TGGTACCAGTTGTTCCTTCC | 374 | AGACAAGCAAATGCTGAGAGA | 429 |
| Sepsis_J8 | Set1Dis08 | hu-sep-CNAD-0101 | 133 | CTCTATATCTTCCCTTCTCGCTTCATTTCATTCATTCCATTGCTTCGATACCCTTTCTTCCAGTTCGATCGGCATCGGCTCCTGAGGCTTCGCATTCTTCACGTAGTTCTCGAGCCTTGGTTTCAGCTC | 101 | chr17:56,191,929-56,192,061 | Intron ANKFN1 RefSeq: NW_153228.2 Status: Validated Description: ankyrin repeat and fibronectin type III domain containing 1 RepeatMasker information Name: L1HS Family: L1 Class: LINE | TTGTTGCGAATGTTTACTGAGAATG | 375 | TGCTGCTCTAAAGACACATGC | 430 |
| | | | | | | | | CTCTATACTTCCCTTCTCGCTTC | 376 | AACCAAGGCTCGAGAACTAC | 431 |

FIG. 3A

Table 3 continued

| | | | | | | | |
|---|---|---|---|---|---|---|---|
| Sepsis J9 | SetIDis09 | hu-sep-CNAD-0102 | ATGGTGTATATGTGCCACATTTCTTAATCCAGTCTATCATTGT TGGACATTTGGGTTGGTTCCAAATCTTTGCTATTGTGAATAAT GCCGCAAAAACATACATGTGCGTGTGTCTTTATGCAGCATG ATTTATATTCCTTTGGGTATATACCCAGTAATGGGATGGCTGG GTCAAATGGTATTTCTAGTTCTAGATCCCTGAGGAATTGCCAC ACTGACTTCCACAATGGTTGAACTAGTTTACAGTCCCACCAAC AGTGTAAAAGTGTTCCTATTTCTCCAC | 205 | chr20:30,141,194-30,141,479 | Name: L1PA3 Family: L1 Class: LINE | 102 | ATCCAGTCTATCATTGTTGGA CATT | 377 | TTTACACTGTTGGTGGGAC TG | 432 |
| Sepsis J10 | SetIDis10 | hu-sep-CNAD-0103 | AGGCATGGGCAAGGATTTCAAGAGGATTTCAAGACTAAAACACCCAAAAGCAAT GGCAACAAAAGCTAATATTTGACAAATGGGATCTAATTAAACTA AAGAGCTTTCTGCACACGCAAAAGAAAACTTTCAGAGTGAACA GGCAACCTACAGAATGGGAGAAAATTTTTGCAATGCTACTCATC TGACAAAGGGCTAATATCCGGAATCTACAATGAACTCAAACAA ATTTACAAAAAAAAACC | 231 | chr7:54,294,767-54,295,004 | Name: L1PA4 Family: L1 Class: LINE | 103 | AGGGCATGGGCAAGGATTT | 378 | TTGTTTGAGTTCATTGTAGA TTCCG | 433 |
| Sepsis J11 | SetIDis11 | hu-sep-CNAD-0104 | GTTTCTGCTGAGGGATCTGCTCTTAGTCTAATGGGCTTCCCTT TGAGGGTAACCCGACCTTTCTTCTTTGGCTGCCCTTAACATTTT TTCCTTCATTCAACTTTGTGAATCGACAATATGTGTCTTTG GAGTTGCTCTTCTCGAGGAGTATCTTTGTGGCATTCTCTGTAT TTCTGAATCTGAATGTTGGCCTTGCTAGATTGGGGAA GTTCTCTGGAATAATATCCTGCAGAGTGTTTTCCAACTTGGTT CCATTCTCCCCA | 270 | chr4:126,929,562-126,929,931 | Name: L1PA2 Family: L1 Class: LINE | 104 | TGCTTGAGGGATCTGCTCTTA | 379 | GGAGAATGGAACCAAGTT GGAA | 434 |
| Sepsis J12 | SetIDis12 | hu-sep-CNAD-0105 | GATCACGAGGTCAGGAGATTGAGACCATCCTGGCTAACACGG TGAAACCCCGTCTCTACTAAAAATACAAAAATTAGCCAGGCG TGGTGGCAGGGCGCCTGTAGTCCCAGCTACTCGGGAGGCTGA GAGCCAAGAATGGCATGAACCCAGGAGGCGGAGCTTGCAGT GGAGACTCCGTCCAAAAAAAGAAAAGAAAAGAAAAAAAA | 246 | chrX:51,840,690-51,840,930 | Intron UNC13C RefSeq: NM_001080534.1 Status: Provisional Description: unc-13 homolog C (C. elegans) RepeatMasker Information Name: AluY Family: Alu Class: SINE | 105 | GATCACGAGGTCAGGAGATT G | 380 | ACGGAGTCTCAGTCTGTCG | 435 |
| Sepsis J13 | SetIDis13 | hu-sep-CNAD-0106 | TATAAAACATGCTGCTATAAAGGCACATGCACATGTATGTTTA TTGCAGCACATTCACAATAGCAAAGACTTGGAACTAACCCAA ATGTCCATCAGTGATATACTGGAGTTAAGAAAACGTGGCACATA TACACCATGGAATACTATGCAGCCATAAAAAATGATGAGTTCA TGTCCTTTGTAGGGACATGGACAATGGAAATTGGAAATCATTCT CAGTAAACTATCGCAAGGACAAAAAA | 241 | | Intron MAGED1 RefSeq: NW_001005232.1 Status: Reviewed Description: MAGE family member D1, transcript variant 3 RepeatMasker Information Name: L1PA3 Family: L1 Class: LINE | 106 | CTGCTATAAAGGCACATGCA C | 381 | GTCCTTGCGATAAGTTTACTG AGA | 436 |
| Sepsis J14 | SetIDis14 | hu-sep-CNAD-0107 | TGTGGTCTGAGAGACAGTTTGTTATAATTTCTGTTCTTTTACAT TTCCTGAGGAGTGCTTTACTTCCAACTATGGTGCAATTTTGG AATAGGTGTGGGTGTGGTGCTGAGAAGAATGTATATTCTGTTG ATTTGGGGTGGAGAGTTCTGTAGATGTCTGTTAGGTCCACTT GGTGCAGAGCTGAGTTCAAGTTCCTGGATATCCTTGTTAAGCT TCTGTCTCATGGAATCTGTCT | 233 | chr6:83,545,838-83,546,070 | Name: L1PA5 Family: L1 Class: LINE | 107 | GTGGTCTGAGAGACAGTTTG TT | 382 | GACAGAATCATGAGACAGA AGC | 437 |

FIG. 3B

Table 3 continued

| | | | | | | | |
|---|---|---|---|---|---|---|---|
| Sepsis 115 | Set1Dis15 | hu-sep-CNAD-0108 | 244 | AAACATACGTGCATGTGTCTTTATAGTAGAATGATTTATAAT CCTTTGGGTATATACCCAGTAATGGGATTGCTGGGTCAAATG GTATTTCTGGTTCCAGATCCTTGAAGGAATCACCCACTGTCTTC CACAATGGTTGAACTAATTTACACTCCCACCAACAGTGTAAAA GCATTCCTGTTTCTCCACATCCTCCAGCATCTGTGTTTC TGACTTTTTAATGATCATTCTAACTG | 108 | chr14:37,839,101-37,839,344 | Intron TTC6 RefSeq: NM_001310135.1 Status: Validated Description: tetratricopeptide repeat domain 6 RepeatMasker Information Name: L1PA7 Family: L1 Class: LINE | ACATACGTGTGCATGTGTCTT 383 | AAACAACAGATGCTGGAG AGG 438 |
| Sepsis 116 | Set1Dis16 | hu-sep-CNAD-0109 | 236 | ATTCAACATAGTATTGGAAGTTCTGGCCAGGGGTAATTAGGCA GGAGAAGGAAATAAAGGGTATTCAATTGCGAAAAGAAGGAAGT CAAATTGTTCCTGTTTGCAGATGACATGATTGTATATCTAGAA AACCCCATTGTCTCAGCCCAAAATCTCCTTAAGCTGATAAGCA ACTTCAGCAAAGTCTCAGGATACAAAAATCAATGTACAAAAATC ATAAGCATTCTTATACCACCAAACAAC | 109 | chr3:105,995,077-105,995,314 | Name: L1PA3 Family: L1 Class: LINE | TCAACATAGTATTGGAAGTT CTGG 384 | GTATCCTGAGACTTTGCTG AAG 439 |
| Sepsis 117 | Set1Dis17 | hu-sep-CNAD-0110 | 198 | GGTCAGGAGTTCGAGACCAGCCTGGCCAACATGGTGAAACC CCATCTCTACTAAATATACAAAAATTACCCGGGCATGGGGACG GGTGCCTGTAATCCCAGCTGTTCAGGAGGCTGAGGCAGGGG AATCGCTTGAACCCGGGAGGCGGAGGTTGCAGTGAACAGAG ATCGTGTCACTGCACTCCAGCCTGGGTGATAG | 110 | chr19:47,935,336-47,935,533 | Name: AluSx1 Family: Alu Class: SINE | GGTCAGGAGTTCGAGACCA 385 | CAGGGTGCGAGTGCCAGTG 440 |
| Sepsis 118 | Set1Dis18 | hu-sep-CNAD-0111 | 111 | GTGTCTGTGTAGAAAGAAGTAGACATGGGAGACTTTTCATTTT GTTCTGTACTTAAGAAAAAATTCTTCTGCCTTGGGATCCTGTTGA TCTGTGACCTTAGCCCCCAACCCTGT | 111 | chrX:54,572,310-54,572,420 | Name: SVA_A Family: SVA Class: Retroposon | GTGTCTGTGTAGAAAGAAGT AGA 386 | GGGTAAGGTCACAGATCAA C 441 |
| Sepsis 119 | Set1Dis19 | hu-sep-CNAD-0112 | 160 | TCTTTGAAACCAACAACAAAGACAACAACATACCAGAATCT CTGGGAACACATTCAAAGCAGTGTGTAGAGGGAAATTTATAGC ACTAAATGCCCAAAGAAGAACAGGAAAGATCCAAAATTGAC ACCCTAACATCACAATTAAAAGAACTAGAAAAA | 112 | chrX:43,673,511-43,673,670 | Intron MAOA RefSeq: NM_001270458.1 Status: Reviewed Description: monoamine oxidase A, transcript variant 2 RepeatMasker Information Name: L1PA3 Family: L1 Class: LINE | GAAACCAACAACAAGAACAAAG ACAC 387 | AATTGTGATGTTAGGGTGT CAA 442 |
| Sepsis 120 | Set1Dis20 | hu-sep-CNAD-0113 | 288 | TCTCTGTTTGTCTTGTTATTGGTGTATAAGAATGCCTTGTGATTTT TGCACGTTGATTTGTATCCTGAGACTTTGCTGAAGTTGCCTA TCAGCTTAAGGAGATTTTGGGCTGAGAACAATGGGGTTTCTA GATATACAAATCATGTCATCTGCAAACAGGAGACAATCTGACTTC CTCTTTTCCCTAATTGAGTACCCTTTATTCCTTCCTCCCTGA TTGCCCTGCCGACGAACTTCCAACACTATGTTGAATAGGAGTG GTGAGAGAGGGGCATCCGCTGTCTTCTGCCAG | 113 | chr3:75,846,800-75,847,087 | Name: L1PA5 Family: L1 Class: LINE | CTCTGTTTGTCTGTTATTGGT GTATAAG 388 | CTGGCAGAAGACAGCGGAT 443 |

FIG. 3C

Table 3 continued

| | | | | | | | |
|---|---|---|---|---|---|---|---|
| Sepsis 121 | Set1Dis21 | hu-sep-CNAD-0114 | 202 | TTTTTGTTCTTGTGATAGTTTGCTGAGAATGATGGTTTCCAG CTTCATCCATGTCCATACAAAGGACATGAACTCATCATTTTAT GGCTGCATAGTATTCCATGGTGTATATGTGCCACATTTTCTTA ATCCAGTCTATCATTGTTGGATATTTGGGTTGGTTCCAAGTCT TTGCTATTGTCAGTAATGTCTCAATAAAC | chrUn_GL000218v1:157,881-158,082 | Name: L1PA5 Family: L1 Class: LINE | TTGTTCTTGTGATAGTTTGCT GAG | 389 | GAGACATTACTGACAATAG CAAAGAC | 444 |
| Sepsis 122 | Set1Dis22 | hu-sep-CNAD-0115 | 256 | ATGCTGGCCTCATAAAATAAGTTAGGGAGGAGGATTCCCTCTTTT CTACTGATTGGAATAGTTTCAGAAGGAATGGTATCAGCTCCTC CTTGTACCTCTGGTAGGATCCGGCTGTGAATCCATCTGGTCC TGGACTTTTTTGGTTGGTAAGCTATTAATTATTGCCTCAATTT CAGAGTCTGTTATTGCTCATTCAGAGATTCAACTTCTTCCTG ATTTAGTCTTGGGAGGGTGTATGTGTGAAGGAATTTATCCA | chr4:144,986,249-144,986,504 | Name: L1P1 Family: L1 Class: LINE | ATAAGTTAGGGAGGAGGATTCCC TCTT | 390 | TGGATAAATTCCTGGACAC ATACAC | 445 |
| Sepsis 123 | Set1Dis23 | hu-sep-CNAD-0116 | 233 | GAGAGATCCACTTGTTAGTCTGATGGGCTTCCATTTGTGGGTA ACCCGACCTTCTCTCTGCTGCCCTTAACATTATTCCTCAT TTCAACTTTGCTGAATCTGAACAATTATGTGTCTTGGAGTTGCT CTTCTCGAGGAGTATCTTTGTGGCATTCTCTGTATTCCTGAA TTTGATTGTTGGCCTGCCTTGCTAGATTGGGGAAGTTCTCCT GGATAATATCCTGCAGAGTG | chrX:110,547,471-110,547,704 | Name: L1PA4 Family: L1 Class: LINE | GAGAGAATCCACTGTTAGTCT GATGG | 391 | CAATCTAGCAAGGCAGGCC AA | 446 |
| Sepsis 124 | Set1Dis24 | hu-sep-CNAD-0117 | 140 | GTCTTGCTCTGTCTGCGCCAGGCTGGAGTGCAGTGGCGCGATC TCGGCTCACTGCAAGCTCCGCCTCCTGGGTTCACGCGATTCT CCTGCCTCAGCCTCCTGAGTAGCTGGGACTACAGGCGTCCAC CACCACGCCCAGCTA | chr5:131,241,005-131,241,144 | Name: AluY Family: Alu Class: SINE | CAGGCGTGGAGTGCAGTG | 392 | TGGTGGACGGCCTGTAGT | 447 |
| Sepsis 125 | Set2Dis01 | hu-sep-CNAD-0118 | 285 | GTTTATATTTGGGATATAAACCCAAAGGATTATAAAATCATGCTT CTATAAAGACACATGCACAAATGTTTATTGTGGCACTATTC ACCATAGCAAAGACTTGGAACCAACCCAAATGTCCAACAATGA TAGAACTGGATTAAGAAAATGTGCACATATACACCATGGAATA CTATGCAGCCATAAGAAATGATGAGTTCATGTCCTTTGTAGGG ACATGGATGAAATTGGAAATCATCATTCTCAGTAAAGTATTGC AAGGACAAAAACCAACCCAACACAC | chr1:147,125,078-147,125,342 | Name: L1PA3 Family: L1 Class: LINE | TTGGGATATAAACCCAAAGG AT | 393 | TTTGTCCTTGCAATACTTTA CTGAG | 448 |
| Sepsis 126 | Set2Dis02 | hu-sep-CNAD-0119 | 292 | AGTTATACATTCTTCTAAATTTTCAAAGTTTTCAACTTCTTT GCCTTTTGGTTTGAATGTCCTCTGATAGCTCAGAGTAATTTGAT CGTCTGAAGCCTTCTTCTCAGCTGCTGCGTCAAAGTCATTCTCCA TCCAGCTTTGTTCTTGTTGCTGGTGGAGGAACTTCGTTCCTTTGG AGGAGGAGGGCGCTCTGCCATCTTTGTTGAGTTTCAGTTTTTCT GTTCGTTTTTCTCCATCTTGTGGTTTATCTACTTTTGGTCT TTGATGATGATCATGATGGGTTTTTTGG | chrX:152,545,367-152,545,651 | Name: L1PA2 Family: L1 Class: LINE | TCAACTTCTTTGCCTTTTGGTT T | 394 | AACCCATCTGTACATCATCA TCA | 449 |
| Sepsis 127 | Set2Dis03 | hu-sep-CNAD-0120 | 243 | GCTAAAAACTCTCAATAATTAGGTATTGATGGATGTATCTC AAAATAATAAGAGCTATTTATGACAAACCCACAGCCAATATCAT ACTGAATGGGCAAAAACTGGAAGCATTCCCTTTGAGAAACTGG CACAAGACAGGGATGCCACTCTATTCAACACTCACCACTCCT ATTCAACATAGTGTTAAGTTCTGGCCAGGGCAATCAGGCA GGAGAAGAAATAAAGGGTATTCAACTAG | chr10:88,630,548-88,630,790 | Name: L1PA5 Family: L1 Class: LINE | AGGTATTGATGGATGTATC TCAAAA | 395 | CCCTTTATTTCTTTCCTGC CT | 450 |
| Sepsis 128 | Set2Dis04 | hu-sep-CNAD-0121 | 259 | TTGTTATTCCTGAGTTCTTAGTTTGGTTAAGGCACTGTGGTCTG AGAGACAGTTTGTTATAATTTCTTTTACATTTGGTTGCTGAGG AGAGCTTTACTTCCAACTATGTGTTCAGTTTTGAAACTTGTCCC TGTTTGCAGATGACATGATTGTATATCTGATAAGCAACTTCAGCACA GTCTCAGGATACAAAATCAATGTACAAAATCACAAGCATTCT TAT | chr6:81,285,316-81,285,574 | Name: L1PA4 Family: L1 Class: LINE | ATTCCTGAGTTCTTAGTTTGGT TACA | 396 | GTATCCTGAGAGTGTGCTG AAG | 451 |

FIG. 3D

Table 3 continued

| | | | | | | | | |
|---|---|---|---|---|---|---|---|---|
| Sepsis 129 | Set2Dis05 | hu-sep-CNAD-0122 | 279 | AATTCGGAACTGGTACCATTCCTTCTGAAAACTATTCCAATTAAT AGAAAAAGAGGGAATCCTCCCTAACTCATTTAAGAGGCCAG CATCATTCTGATACCAAAGCCGGCAGAGACCACAACCAAAAAT CAGAATTTTAGACCAATATCCTTGATGAACATTGATGCAAAAAT CCTCAATAAAATACTGGCAAACTGAATCCAGCAGACATCAAA AAGCTTATCCACCATGACAAGTGGCCTTCATCCCTGGGACG CAAGGCTGGTTCAATATACGC | chr7:72,296,175-72,296,469 | Intron CALN1 RefSeq: NM_001017440.2 Status: Validated Description: calneuron 1, transcript variant 2 RepeatMasker Information Name: L1P1 Family: L1 Class: LINE | CTGGTACCATTCCTTCTGAAA CTA | 397 | GCGTATATTGAACCAGCCT TG | 452 |
| Sepsis 130 | Set2Dis06 | hu-sep-CNAD-0123 | 272 | ACCGCTAGCCAAGACTAATAAAGAAAAAAGAGAAGAATCAA ATAGACGACAATAAAAAATGATAAAGGGGATACCACCACTGATC CCAAGAGAAATACAACACTACCATTCAGAGAATACTACAAACACCT CTATGCAAATAAAACTAGAAAATCTAGAAGCAAATGGATAAATTC CTTGACACGTACATGCTCCCAAGACTAAACCAGGAAGAAGTT GAATCTCTGAATAGAACCAATAACAGGAGCTGAAATTGGGGCA ATAATCAATAGCTTAC | chr4:44,049,367-44,049,638 | Name: L1PA3 Family: L1 Class: LINE | ACCGCTAGCAAGACTAATAA AG | 398 | CCCAATTTCAGCTCCTGTT | 453 |
| Sepsis 131 | Set2Dis07 | hu-sep-CNAD-0124 | 241 | TGACATGGGGTCTCCTGAATACAAGCACACTGATGGGTCTTGAC TCTTTATCCAATTTGCCAGTCGTGTCTTTTAATTGGGGCATT CAGCCCATTTACATTTAAGGTTTAATTTATGTTATGTGTGAATTTG ATCCTGTCATTATGATGTTAGCTGCATCTATGGTCTTTACAGTCTGGCA GATGCAGTTTCTTCCTAGCATCTATGGTCTTTACAGTCTGGCA TATTTTGCAGTGGCTGGTACTGGGTTG | chr9:14,682,060-14,682,301 | Intron ZDHHC21 RefSeq: NW_178566.4 Status: Validated Description: zinc finger DHHC-type containing 21 RepeatMasker Information Name: L1PA5 Family: L1 Class: LINE | TGACATGGGGTCTCCTGAATA C | 399 | AGTACCAGCCACTGCAAA | 454 |
| Sepsis 132 | Set2Dis08 | hu-sep-CNAD-0125 | 184 | CCTTTGTGATGTGTGTGTTCAACTCACAGAGTTTAACACCCAC ACCCCAAACACACACCCAACACAAAGGAGTTTCTGAGAATCATTC TGTCTAGTTTTCTACGAAGATATTTCCTTTTCTACTATTGACC TCAAAGCGGCTGAAATCTCCACTTGCAAATTCCAACGAAAAGAG TGTTTCAAGTC | chr5:49,480,986-49,481,117 | Name: ALR/Alpha Family: centr Class: Satellite | CCTTTGTGATGTGTGTGTTCA A | 400 | CGTTGGAATTTGCAAGTGGA G | 455 |
| Sepsis 133 | Set2Dis09 | hu-sep-CNAD-0126 | 278 | CACCCACTCCAGCATATAAACAGAACCAAAAGACAAAAACCACA TGATTATCTCAATGGATGCAGAAAAAGGCCTTTGACAAAATTCA ACAACCCTCATGTCTAAAAACTCTCAATAAGTTAGGTATTGAT GGGACATATTTCAAAATAATACTAAGAGCTATCTATGACAAACCCA CAGCCAATATCATATCGACAAGACAGGGATGTCTCTCTTACCACTC TTTGAAAACTGGACAAGAGCATTTCC TTATTCAACATAGTAATGGA | chr9:63,108,686-63,108,956 | Name: L1PA3 Family: L1 Class: LINE | CACCCACTCCAGCATATAAA CA | 401 | GAATAAGAGTGGTAAGAG AGGACATC | 456 |
| Sepsis 134 | Set2Dis10 | hu-sep-CNAD-0127 | 274 | CCTCAAGCTATCCAAATATCCACTTTCAGATTCCACAAAAG AGTGCTGTCTGTAATAAGAAAAGGTTCATCCCTGTTAGTTGAA TACACACATCACAAAACAAGTTTCTGAGAATGCTTCTGTCTAGT TTTATGGGAAGATATATTCCTTTTCAACATAGGCCTCAAAGC GCTCCAAACGTCCACTTCCAGGTAGTGCAGAAAAGAGTGTCTC AAACCTGGTATATAAACAGGGAACATTCTATTCTGTGACTTGAA TGAAAACATCACAAAGC | chr9:44,936,918-44,937,199 | Name: ALR/Alpha Family: centr Class: Satellite | CCTCCAAGCTATCCAAATATC CA | 402 | TCACAGAATAGAATGTTCC CTGTTA | 457 |

FIG. 3E

Table 3 continued

| | | | | | | | | | |
|---|---|---|---|---|---|---|---|---|---|
| Sepsis.136 | Set2Dis11 | hu-sep-CNAD-0128 | 289 | TACCCCTTCTTCCAGTTGATCGCATCGGCTCCTGGAGGCTTCTG CATTCTTCACGTAGTTCTCGAGCCTTGGTTTCAGCTCCATCA GCTCCTTAAGCACTTCTCTGCAGTTGTTATTCTAGTTATAAAT TCTTCTAAATTTTTTCAAAGTTTTCAACTTCTTTGCCTTTGGT TTGAATGTCCTCCCGTAGCTCAGAGTAATTTGATCGTCTGAAG CCTTCTTCTCTCAGCTCGTCAAAATCATTCTCCATCCAGCTTT GTTCCCGTTGCCTGGTGAGAGAACTGCGTTCC | 128 | chrX:106,470,255-106,470,543 | Name: L1HS Family: L1 Class: LINE | TACCCTTCTTCCAGTTGATC G | 403 | AACGGCAGTTCCTCACCAG |
| Sepsis.136 | Set2Dis12 | hu-sep-CNAD-0129 | 227 | AGTTGGCTTCATCCCTGGGATGCATGGCTGTTCAACATACA CAAATCAATAAACGTAATCCATCATATAAACAGAACCAAAGACA AAAACCACATGATTATCTCAATAGATGCAGAAAAAGGCCTTTGA CAAAATTCAACAACTCTCATGCTAAAAACTCTCAATAAATTAG GTACTGATGGGACGTGTCTCAAAATAATAAGAGCTATCTATGA CAAACCCACAC | 129 | chr19:23,617,308-23,617,533 | Name: L1PA5 Family: L1 Class: LINE | GGATGCATGGCTGTCGTTCAA | 404 | GTGTGGGTTTGTCATAGAT AGCTC |
| Sepsis.137 | Set2Dis13 | hu-sep-CNAD-0130 | 283 | GAGTCAGAGAGGATTCCCTCTTTTCTGTTGATTGGAATAGTT TCAGAAGGAATGGTACCAGCTCCTCCTTGTACCTCTGGTAGA ATTCGGCTGTGAATCCATCTGGTCCTGGACTCTTTTGGTG GTAAGCTATTGATTATTGCCACAATTCAGATCCTGTTATTGG TCTATTCAGAGATTCAACTTCTTCCGTTTAGTCTTGAGAGA GTGTAACATGTCTAGAAATTTATCCATTTCTTCTAGATTTTCTAG TTATTTGCATAGAGGTATTGTAGT | 130 | chr1:166,226,536-166,226,810 | Name: L1P1 Family: L1 Class: LINE | TGTTGATTGGAATAGTTTCA GAAGG | 405 | CTAGACATGTACACTCTCTC AAGAC |
| Sepsis.138 | Set2Dis15 | hu-sep-CNAD-0131 | 277 | CATTTATTGATTTGCATATATTGAACCAGCCTTTCATCCCAGG GATGAAGCCCACTTGATCATGGTGATAAGCTTTTTGATGTG CTGCTGGATTCGGTTTGCCAGTATTTGTTCTAAAATTCTTTTGTTGTG TCATGGATATTGTTCATAAATTCTTTTTGTTGTG TCTCTGCCAGGCTTTGTATCAGGATGATGATGATCGGCGCTCATAA AATCAGTTAGGGAGGAATTCCCCTCTTTTCAGTTGATTGGAATA GTTTCAGAAGGAATGGTACC | 131 | chr4:182,781,356-182,781,633 | Name: L1PA2 Family: L1 Class: LINE | TGCATATATTGAACCAGCCTT TC | 406 | GGTACCATTCCTTCGAAAC TATTC |
| Sepsis.139 | Set2Dis16 | hu-sep-CNAD-0132 | 246 | TTTGGTTTGTTTGTTACAGCATTTGGAAACCTTCAAATCTAT CCAAATATCCCAGATCCAGATCCCACAAAAAGAGTGTTTCCAAA ATGCTGTATCCAAAACAAAGGTTCAACTCTCTGTTAGTTGAGAACA CACATCGCAAATAAGTTTCTGAGAATGCTTCTGTCTAGTTTTT ATTTGAAGATATTTCCCTTTTCACCACAGCGCTGAAAGCGCTT GAAACGTCCGCTTGCAGATACTACAAAAGG | 132 | chr9:45,070,186-45,070,399 | Name: Alr/Alpha Family: centr Class: Satellite | GGAAAACCTTCAAATCTATCC AAATATCC | 407 | TATCTGCAAGCGGACGTTT C |
| Sepsis.140 | Set2Dis18 | hu-sep-CNAD-0133 | 259 | GTTTGGGTTGTTTGTGCATGCATTGTTGTATGCTGAGACTTTGC TGAAGTTGCTTATCAGCTTAAGGAGATTTTGGCATGAAGGGTT GTTGAAATTTTGTCAAAGGCCTTTCTGCATCTATTGAGATAAT CATGTGTTTTTGTCTTTTGGTTTCTCTGTTTATATGCTGGATTACA TTTATTAATTTGCATATATTGAACCAGCCTTGCATCC | 133 | ? | ? | TGGGTTGTTTGTGCATTGATT T | 408 | GGAATGCAAGGCTGGTTCAA TA |
| Sepsis.141 | Set2Dis19 | hu-sep-CNAD-0134 | 285 | AACTATCTCAGACCACAGTGCAATCAAAACTAGAACTCAGGA TTAAGAAACTCGCTCAAAAACGCTCAACTACATGGAAACTGAA CAACCTGTCCTGAATGACTACTGGGTAAATAATGAAATGAAG GCAGAAATAAAGATTTTCTTTGAAACCAACGAAGAACAAAGACA CAACATACCAGAGAATCTCTGGGACACATTCAAAGCAGTATGTAG AGAGAAATTTATAGAACTAAATGCCACAAGAAGAGAAGGAA AGATCTAAAATTGACACCATAATATCA | 134 | chr1:74,900,774-74,901,052 | Name: L1PA4 Family: L1 Class: LINE | CTCTCAGACCACAGTGCAAT C | 409 | TTAGATCTTTCCTGCTTTCT CTTGT |
| Sepsis.142 | Set2Dis20 | hu-sep-CNAD-0135 | 234 | GGTTTTTTGGTTTGAAAGTCCTCCTGTAGCTCGAAGTAATTTG ATCTTCTGAAGCCTTCTTCTCTGCTGTCAGTCATTCTCCG TCCTGCTTTGTTCCGTTTGCTGCTGGAAGAACTGCGTTCCTTG GAGGAGGAGGGTGCTCTGCTCTTTTAAGCTTTCCAGTTTTTC GTTCTGTTTTTTTCCCCATCTTTGTGGTTTTATGTATCTTTGGTC TTTGATGATGGTGAATGTAC | 135 | chr10:90,158,388-90,158,618 | Name: L1PA3 Family: L1 Class: LINE | TGGTTTTGAAAGTCCTCCTGTA G | 410 | CATCACCATCATCAAAGAC CAAA |

FIG. 3F

Table 3 continued

| | | | | | | | |
|---|---|---|---|---|---|---|---|
| Sepsis 143 | Set2Dis21 | hu-sep-CNAD-0136 | 270 | CACACCCAACACAATCAAAAAGCTTATCCACCATGATCAAGTGG GCTTCATCCCTGGGATGCAAGCTGGTTCAATATACGCAAAT CTATAAGTGTAATCCAGCATACAAACAGAACGACAAAAA CCACATGATTATCTCAATAGATGCAGAAAAGGCCTTTGAACAA ATTCAACAACCCTTCATGCTAAAAACTCTCAGTAAATTAGGTAT TGAATGGGATGTATCTCAAAATAATAAGAGCTATTTATGAACAAA CCCACACCAAAC | 136 | chr8:47,022,369-47,022,631 | Name: L1PA3<br>Family: L1<br>Class: LINE | CCATGATCAAGTGGGCTTCA | 411 | TTTGGTGTGGGTTTGTCAT AAATAG | 466 |
| Sepsis 144 | Set2Dis22 | hu-sep-CNAD-0137 | 264 | CCTCATAAGTTGGATTCCTAGGTATTTGTTCTTTTTGAAGCA ATTGTGAATGGGAGTTTACTCATGATTTGTTATTTTGCACATTGAT TGTTATTGGTGTATAGGAATTGTTTGCTCTCTGTTTGTC TTGTATCCTGAGACTTTGCTGAAGTTGCTATCAGCTTAAGAA GATTTTGGGCTGAGACGATGGGGTTTCTAAATATACAATCAT GTCATCTGCAAACAGGGACAATTTGAGTTCCTCTTTTCCTAAT TGAAT | 137 | chr13:63,416,597-63,416,859 | Name: L1PA5<br>Family: L1<br>Class: LINE | GAAGCAAATTGTGAATGGGA GTTT | 412 | AGGAACTCAAATTGTCCCT GTT | 467 |
| Sepsis 145 | Set2Dis23 | hu-sep-CNAD-0138 | 195 | CATAAAATGAGTTAGGGAGGATTCCCTCTTTTTCTATTGATTG GAATAGTTTCAGAAGGAATGGTACCAGTTCCTTCTGAAACTAT TCCAATCAATAGAAAAAGAGGGAATCCTCCCTAACTCATTTTA TGAGGGCCAGCATCATTCTGATACCAAAGCCGGGCAGAGACAC AACCAAAAAAGAGAATTTTAGACC | 138 | chr3:137,636,155-137,636,297 | Name: L1PA2<br>Family: L1<br>Class: LINE | GAGTTAGGGAGGATTCCCTC TT | 413 | GTCTCTGCCGGCTTTG | 468 |
| Sepsis 146 | Set2Dis24 | hu-sep-CNAD-0139 | 205 | TTGGTTTGGTTTGCCAGTATTTTATGAGGCCAGCATCATCCTG ATACCAAAGCCTGTAGAGAACACACCAATATCCCTGATGAACA TCAATGCAAAATCCTCAATAAAAATACTGGCAAACCGAATCCA GCAGCACACTCAAAAAGCTTATCCACCATGATCAAGTGGGCTTC ATCCCTGGGATGCAAGGCTGGTTCAATATACGC | 139 | chrX:104,916,881-104,917,088 | Intron iL1RAPL2<br>RefSeq:<br>NM_017416.1<br>Status: Reviewed<br>Description: interleukin 1 receptor accessory protein like 2<br>RepeatMasker Information<br>Name: L1PA3<br>Family: L1<br>Class: LINE | TTTGGTTTGGTTTGCCAGTATT T | 414 | GTATATTGAACCAGCCTTG CATC | 469 |
| Sepsis 147 | Set2Dis25 | hu-sep-CNAD-0140 | 258 | CTGTTTACATGCTGGATTACGTTTATTGATTTGCGTATGTTGA ACCAAAGACAAAAACCATGATTATCTCAATAGATGCAGAAAA AGGCCTTTGACAAGTTCATGGGACGTATCTCAAAATAATAAA CAATAAATTAGGGTATTAGTGGAACGTATCTCAAAATAATAAAA GCTATCTATGACAAAATCCCACGCCAATATCATATGAATGGGC AAAAACTGGAAGCATTCCCTTTGAAAACTGGCACAAGAAAGG G | 140 | chr2:223,015,742-223,015,958 | Name: L1PA5<br>Family: L1<br>Class: LINE | CTGTTTACATGCTGGATTACG TTTA | 415 | CCCTTCTTGTGCCAGTTT | 470 |
| Sepsis 148 | Set2Dis26 | hu-sep-CNAD-0141 | 289 | GCTCGGAGTAGTTTGATCGTCTGAAGCCTTCCTCCTCAGCT CGTCAAAATCATTCACCATCGCAGCTTTGTTCCGTTGCTGGTGA GGAAGTTTCCAGTTTTCTCTCTGTTTTTCCCCATCTTTGTGG AGAGTTTCCAGTTTTCTCTCTGTTTTTGATGATGGTGATGTACAGATGG TTTTATCTACTTGGTGTGGAAGCTGTCCTTTCGTTGTTTTCCTTCTA ACAGACAGGACCCTCAGCTGCAGGTCTGTAC | 141 | chrX:66,929,807-66,930,093 | Name: L1PA2<br>Family: L1<br>Class: LINE | CTCGGAGTAGTTTGATCGTC TG | 416 | TGAGGGTCTGTCTGTTAG A | 471 |
| Sepsis 149 | Set2Dis27 | hu-sep-CNAD-0142 | 202 | TTTTTGTGTCTCGCCTGGCTTTGGTATCAGAATGATGCT GACCTCATAAAATGAGTTAGGGAGGACTCCCTCTTTTCTGTT GATTGGAATAGTTTCAGAAGGAATGGTACCCAGCTCCTCCTTGT ACCTTGGTAGAATTCGGCTGTGAATCATCTGGTCCTGCTGAC TCTTTTATGAGGGCCAGCATCATTCTGATAC | 142 | chr6:65,099-65,276 | Name: L1PA2<br>Family: L1<br>Class: LINE | CTCGGAGTAGTTTGATCGTC TG | 417 | AGAATGATGCTGGCCTCAT AAA | 472 |
| Sepsis 150 | Set2Dis28 | hu-sep-CNAD-0143 | 104 | GGTCTGGAGTGGACCTCCAAAAAGGGTCTGGAGTGGACCTC CAGCAAACTCCAACAGACCTGCAGTGAGGGTCCTGACTGTT AGAAGGAAACTAACAAACAG | 143 | chr8:56,151,332-56,151,435 | Name: L1PA5<br>Family: L1<br>Class: LINE | CTCTGCCTGGCTTTGGTATC | 418 | TAACAGTCAGGAGACCCTCAG | 473 |

FIG. 3G

Table 3 continued

| | | | | | | | |
|---|---|---|---|---|---|---|---|
| HSMC3 | hu-sep-CNAD-0144 | 184 | TACTTAGATAACCACAGCCTAAGAATTCATTAGCTTTTAAAACA ATCTTGCTTCACACTTGACTTGCCTTCACAATCAACACAA AGTCTTTTGGGTTTAAATGATTTTCAAGTCCTTTCAATGCTGT GATATTATTGTTATCTCCTCCACGTTCTTTGTTTAAACTATTGG TCTGCCGGGCGCCGGTGGGCTCACAC | 144 | 1:160165300 - 160165499 | Intron ATP1A4 RefSeq: NM_144699.3 Status: Reviewed Description: ATPase Na+/K+ transporting subunit alpha 4, transcript variant 1 RepeatMasker Information Inter-Repeat Region Name: L3 Family: CR1 Class: LINE Name: AluYh3a3 Family: Alu Class: SINE | ACTTAGATAACCACAGCCTA AGAA | 419 | CCCCGGCAGACCAATAAGTTT A | 474 |
| Sepsis 51 | | | | | | | | |
| HSMC6 | hu-sep-CNAD-0145 | 170 | GGATGGAATGCCCAACAAATACTTAGATTTATGGGTTTGGAAC CCAGGAGAGATCTCAGTAAAATGATAAAGAGTTGAGAGTCAT TGGCCCTGTAGATTCATTCATCTACTCCATTCAGTAAATATTCACT TACTAACGTGCTTTGTCTCAGGCATTAAGTATACAGTGGTAAA TTAAAACATTATTTTTAGTTTTTCACAAA | 145 | 1:61330172 - 61330371 | Intron NFIA RefSeq: NM_001134673.3 Status: Reviewed Description: nuclear factor I A, transcript variant 1 RepeatMasker Information Name: L2c Family: L2 Class: LINE Name: L2b Family: L2 Class: LINE | GGATGGAATGCCCAACAAAT AC | 420 | ACCACTGTATACTTAATGCC TGAG | 475 |
| Sepsis 52 | | | | | | | | |
| HMSC10 | hu-sep-CNAD-0146 | 145 | GCAGCCTCTACTATTCCTTACTTTATTATACCCACCCATTTTCC TCACTTTCTATCATTTGCCTGGTCCATGTAGGCCATCTGAGTTT AAGATCTCTGGCATACAGTTTATCTGGGAAGATAAGCTACACA TACCACACACTCCACATATC | 146 | 11:95995750 - 95995899 | Intron MAML2 RefSeq: NM_032427.3 Status: Reviewed Description: mastermind like transcriptional coactivator 2 RepeatMasker Information Name: MER102c Family: hAT-Charlie Class: DNA | GCAGCCTCTACTATTCCTTAC TTT | 421 | GTGGAGTGTGTGGTATGTG TAG | 476 |
| Sepsis 53 | | | | | | | | |

FIG. 3H

Table 3 continued

| | | | | | | | | |
|---|---|---|---|---|---|---|---|---|
| Sepsis 54 | HSMC16 | hu-sep-CNAD-0147 | 164 | TCTGCGCTTCAAATGCCACTTTGTTTACTCGCTGTGGTCATCCTTTTCTGTAAATACTGTGTCAGCATTAACAGCCTCCTCTATGGCTACCTAGCAGGTCACTTAGTAAACTATCTTTTAGTAACAACTACATAGAATGAATACTCAGGAGCCTTAATTCAATTTACCCTGCATAAAGAAACTATTCACTATTACAAACACA | 147 | 1:211148562 - 211148761 | | GCTTCAAATGCCACTTTGTTTAC | 422 | AGGTAAATTGAATTAAGGCTCCTG | 477 |
| Sepsis 55 | HSMC17 | hu-sep-CNAD-0148 | 181 | CAGTCCTAAAGAGGGAGACATTATTACTTTCCCCATTCGTAGAATGAGTAAACTGAGTTTTAAGTAGGTTAAATGTTTGTACAGGATTACAGAATTAGAGAATGAAAGAACCACATGGCAAACCCATGTAGTTTGTGCCAAATTTATACTCTTCGTGTCATAGCGGTCCTTGATTGTGAGGTTCATTCAAAGCCAGCA | 148 | 10:85022600 - 85022799 | Name: MIRb<br>Family: MIR<br>Class: SINE | CAGTCCTAAAGAGGGAGACATTATT | 423 | TCACAATCAAGGACCGCTATG | 478 |

FIG. 31

SEQUENCE LISTING

<160> NUMBER OF SEQ ID NOS: 478

<210> SEQ ID NO 1
<211> LENGTH: 166
<212> TYPE: DNA
<213> ORGANISM: Homo sapiens

<400> SEQUENCE: 1
aaacgtccgc ttgcagatac tacaaaaaga gcgtttcaaa cctgctctat gaaaggcaat      60
gttcaactct gtgacttgaa tgcagacatc acagagcagt ttctgagaat gcttctgtct     120
agattttata ggaagatatt cccgtttcca acgaaatctt cacagc                    166

<210> SEQ ID NO 2
<211> LENGTH: 146
<212> TYPE: DNA
<213> ORGANISM: Homo sapiens

<400> SEQUENCE: 2
ggaaatatgg caaagtattt tctgagtatg ctgctgtgta cgttttatat tgcatcccgt      60
ttccaacgaa atcctcaaag cgatccaaat atccacttgc agattccaaa aaagagtgt     120 ttcaaactgc tctgtcagta caaagg                                          146

<210> SEQ ID NO 3
<211> LENGTH: 261
<212> TYPE: DNA
<213> ORGANISM: Homo sapiens

<400> SEQUENCE: 3
tctttgaggc tttcgttgga aacgggattt cttcacataa tgctagacag aagaattctc      60
agtaacttct tttgggatgt atgtattcaa ctcagagagt tgaaccttcc tttagacaga     120
gcggattgga aacacgcttt tgcggaatt tcaggtgga gattccaaga gccttgaggc       180
cagtggtaga aaaggctatc ttcgtataaa aactagaggg aatcattctc agaaactgct     240
ttgtgatgtg tgcattaaac t                                               261

<210> SEQ ID NO 4
<211> LENGTH: 199
<212> TYPE: DNA
<213> ORGANISM: Homo sapiens

<400> SEQUENCE: 4
tgtgaactca gctaacagag gtggatcttt cttttgatag agcagttctg aaaaacactt      60
tttgttgaat ctgcaagtgg acatttggat agatttgaag atttcgttgg aaacgggaat     120
atcttcatat caaatctaga cagcagcatt cccagaaatt tctttcggat atttccattc     180
aactcataga gatgaacat                                                  199

<210> SEQ ID NO 5
<211> LENGTH: 214
<212> TYPE: DNA
<213> ORGANISM: Homo sapiens

<400> SEQUENCE: 5
cttgtggcct tcgttggaaa cgggatttct tcatattatg ctagacagaa gaattctcag      60
taacttcctt gtgttgtgtg tattcaactc acagagttga acgatccttt acacagagca     120
gacttgaaac actcttttg tggaatttgc aagtggagat tcagccgct ttgagttcaa       180 tggtagtata ggaaatatct tcctatagaa acta                                 214

```
<210> SEQ ID NO 6
<211> LENGTH: 171
<212> TYPE: DNA
<213> ORGANISM: Homo sapiens

<400> SEQUENCE: 6
atatttggat agctgtgaag atttcgttgg aaacgggaat atcttcctat aaaatctaga      60
cagaagcatt ctcagaaact gctctgtgat gtttgcattc aagtcacaga gttgaacatt     120
gcctttccta gagaggtttg aaacgctctt ttggtagtat atggaagtgg a              171

<210> SEQ ID NO 7
<211> LENGTH: 160
<212> TYPE: DNA
<213> ORGANISM: Homo sapiens

<400> SEQUENCE: 7
ctcagctaac agaggtggat ctttcttttg atagagcagt tctgaaaaac acttttttgtt     60 gaatctgcaa gtggacattt ggatagattt gaagatttcg ttggaaacgg aatatcttc     120 atatcaaatc tagacagaag cattctcaga atcttctttg                           160

<210> SEQ ID NO 8
<211> LENGTH: 140
<212> TYPE: DNA
<213> ORGANISM: Homo sapiens

<400> SEQUENCE: 8
agtggagaac acacatcaca atcaaggttc tgagaatgct tctgtctaaa ttttctatga      60
agacattccc gtttccaacg aaatcctcac agctatccaa atatccactt gcagattcta     120
caaaaagtgt ggttcaaaac                                                 140

<210> SEQ ID NO 9
<211> LENGTH: 261
<212> TYPE: DNA
<213> ORGANISM: Homo sapiens

<400> SEQUENCE: 9
aatatcttcc cctacaagct agaaagaagc attctgtgaa acttgtttgt gatgtgtgta      60
ctcaactaac agaagagaac cttccttttg acagagcagt tttgatacac tcttttttgta    120 gaatctgcaa gtggatattg ggatagctgt gaagatttcg ttggaaacgg aatatcttc     180 ctataaaatc tagacagaag cattctcaga aactactctg tgatgtctgc attcaagtca     240
cagagttgaa cattgccttt c                                               261

<210> SEQ ID NO 10
<211> LENGTH: 137
<212> TYPE: DNA
<213> ORGANISM: Homo sapiens

<400> SEQUENCE: 10
cctttatgac gtatgcactc acctaacaga gaagaacctt ccttttgaca gagcagtttt      60
gatacactct ttttgtagaa tctgcaagtg gatatttgga tagctgtgaa gatttcgttg     120
gaaacgggaa tatcttc                                                    137

<210> SEQ ID NO 11
<211> LENGTH: 254
<212> TYPE: DNA
```

<213> ORGANISM: Homo sapiens

<400> SEQUENCE: 11

| | | | | | |
|---|---|---|---|---|---|
| tttttgttgt | atctggatgt | ggacatttgg | agcgctttca | gccctatggt | gaaaaggaa | 60 |
| atatcttctc | ctgaaaacta | gacagaagca | ttctcagaat | cttatttgtg | atgtgcgccc | 120 |
| tcaactaaca | gtgttgaagc | tttcttctga | tagagcagtt | ttgaaacact | cttttcgtaa | 180 |
| aatctgcaag | aggatatttt | gatagctttg | aggatttcgt | tggaaacggg | attgtcttca | 240 |
| tataaactct | agac | | | | | 254 |

<210> SEQ ID NO 12
<211> LENGTH: 288
<212> TYPE: DNA
<213> ORGANISM: Homo sapiens

<400> SEQUENCE: 12

| | | | | | |
|---|---|---|---|---|---|
| ctttaaggtc | aatggcagaa | aaggaaatat | cttcgtttca | aaactagaca | gaatcattcc | 60 |
| cacaaactgc | gttgtgatgt | gttcgttcaa | ctcacagagt | ttagcctttc | ttttcataga | 120 |
| gcagttagga | aacactctgt | ttgtaaactc | tgcaagtgga | tattcagacc | tctttgaggc | 180 |
| cttcgttgga | aacgggattt | cttcatacta | tgctagacaa | aagaattctc | agtaacttcc | 240 |
| acgtgttgtg | tgtattcaac | tcacagagct | gaacgatcct | ttacacag | | 288 |

<210> SEQ ID NO 13
<211> LENGTH: 208
<212> TYPE: DNA
<213> ORGANISM: Homo sapiens

<400> SEQUENCE: 13

| | | | | | |
|---|---|---|---|---|---|
| aagaattctc | agtagcttct | tgtgtgtgt | attcaactca | cagagttgaa | ccttcctta | 60 |
| gacagagcag | acttgaaaca | ctcttttgt | ggaatttgca | agtggatatt | tcagccgctt | 120 |
| tgaggtcaat | ggtagaatag | gaaatatctt | ccaatagaaa | ctagacagaa | tgattctcag | 180 |
| aaactccttt | gtgatgtgtg | cgttcaac | | | | 208 |

<210> SEQ ID NO 14
<211> LENGTH: 126
<212> TYPE: DNA
<213> ORGANISM: Homo sapiens

<400> SEQUENCE: 14

| | | | | | |
|---|---|---|---|---|---|
| gaagaattcc | cgtttccaac | gaaggccaca | agatgtcaga | atatccactt | acagacttta | 60 |
| caaacagagt | gtttcctaac | tgctctatga | acagaaaggt | taaactctgt | gagttgaacg | 120 |
| aacaca | | | | | | 126 |

<210> SEQ ID NO 15
<211> LENGTH: 254
<212> TYPE: DNA
<213> ORGANISM: Homo sapiens

<400> SEQUENCE: 15

| | | | | | |
|---|---|---|---|---|---|
| gagttcaacc | tttcttatga | tacagcagtt | tggaaacact | cttttatag | aatttgcaag | 60 |
| ctgatacatg | gatagcccta | actatttcgt | tggaaacggg | aatatcttca | cataaaacct | 120 |
| agacagaagc | actctcagaa | actactttgt | gatatctgca | ttgatatcag | agagttgaat | 180 |
| attccctttc | taagggcagg | cttgaaagcg | tcttttcgtg | gaatctgcag | gaggatattt | 240 |
| ggatagcttg | gagg | | | | | 254 |

<210> SEQ ID NO 16
<211> LENGTH: 171
<212> TYPE: DNA
<213> ORGANISM: Homo sapiens

<400> SEQUENCE: 16

```
attcttctgt ctagcatagt atgaagaaat cccgtttcca acgaaggcct caaagaggtc    60
tgaatatcca cttgcagagt ttacaaacag agtgtttcct aactgctcta tgaagagaaa   120
ggttaaactc tgtgagttga acgcacacat cacaaagaag tttctgagaa t            171
```

<210> SEQ ID NO 17
<211> LENGTH: 219
<212> TYPE: DNA
<213> ORGANISM: Homo sapiens

<400> SEQUENCE: 17

```
gtaaagtctg caagtggatg tttggacctc tttgaggcct tcgttggaaa cgggatttct    60
tcatataatt ctagacagca gaattttcag taacttcctt gtgttgtgtg tattcaactc   120
acagagttga acgatccttt acacagagca gacttgaaac actcttttg tggaatttgc    180
aagtggagat ttcagccgct tgaggtcaa tagtagaaa                           219
```

<210> SEQ ID NO 18
<211> LENGTH: 211
<212> TYPE: DNA
<213> ORGANISM: Homo sapiens

<400> SEQUENCE: 18

```
ctccaccata gccctcaaag cgctccaagt gtccgctagc agattccaca gaaacagtgt    60
ttcaaaactg ctctaacaaa agaaagattc aactccgtga tttgaatgca cacatcacaa   120
agcattttct gtgaatcctt ctgtctagtt tttatatgag gatatttcct tttctaccat   180
gggcatcaaa gggttccaat tatccaattg t                                  211
```

<210> SEQ ID NO 19
<211> LENGTH: 234
<212> TYPE: DNA
<213> ORGANISM: Homo sapiens

<400> SEQUENCE: 19

```
atgacgcttc tgagaatgct tctgtctaga gtttatatga agacaatccc gtttccaacg    60
aaatcctcaa agctatccaa atatcctctt gcagatttta caaaagagt gtttcaaaac   120
tgctctatca aagaaagct tcaacactgt tagttgaggg cgcacatcac aaataggatt   180
ctaagaattc ttctgtctag tttttatttg aagatatttc ctttctcacc atag        234
```

<210> SEQ ID NO 20
<211> LENGTH: 221
<212> TYPE: DNA
<213> ORGANISM: Homo sapiens

<400> SEQUENCE: 20

```
ggaatgttca actctgtgac ttgaatgcag acatcacaga gcagtttctg agaatgcttc    60
tgtctagatt ttataggaag atattcccgt ttccaacgaa atcttcacag ctatccaaat   120
atccacttgc agattcaaca aaagtgtttt tcagaactg ctctatcaaa agaaagatcc    180
acctctgtta gctgagttca cacatcacaa acaagtttat g                      221
```

<210> SEQ ID NO 21
<211> LENGTH: 195
<212> TYPE: DNA
<213> ORGANISM: Homo sapiens

<400> SEQUENCE: 21

```
catccctgtc ttgtgccagt tttcaaaggg aatgcttcca gttttttgccc attcagtatg      60
atattggctg tgggtttgtc atagatagct cttattattt tgagatatgt cccaccaaca     120
ccaaacacac ccaacacaag acaagtatgt cctctctcac cactcctatt caacatagtg     180
ttggaagttc tggcc                                                      195
```

<210> SEQ ID NO 22
<211> LENGTH: 174
<212> TYPE: DNA
<213> ORGANISM: Homo sapiens

<400> SEQUENCE: 22

```
aaaacagact ttaaaccaac aaagatcaaa agagacaaag aaggccatta cataatggta      60
aagggatcaa ttcaacaaga gagctaact atcctaaata tatatgcacc caaaaaccaa     120
acacacccaa cacatacagt aaaattggaa cacacaatca gacgtaaaac aatc           174
```

<210> SEQ ID NO 23
<211> LENGTH: 292
<212> TYPE: DNA
<213> ORGANISM: Homo sapiens

<400> SEQUENCE: 23

```
aaatcctcca attaaaagac acagactggc aaattggata aagagtcaag acccatcaga      60
gtgctgtatt caggaaaccc atctcacatg cagagacaca cataggctca aaatgaaggg     120
atggaggaag atctaccaag caaatggaaa acaaaaaaag gcagaggttg caatcctagt     180
ctctgataaa acagacttta aaccaacaaa gatcaaaaga acaaagaag gccattacat     240
aatggtaaag ggatcaattc aacaagaaga gctaactatc ctaaatatat at            292
```

<210> SEQ ID NO 24
<211> LENGTH: 228
<212> TYPE: DNA
<213> ORGANISM: Homo sapiens

<400> SEQUENCE: 24

```
gcagtagagg atataactgc ccataaaaac tagacagtag cattcccagg aaacactttg      60
tgacgattga gttcaactca cagagctgaa cattcctttg gatggagcag tttcaaaaca     120
cactttctgt agaatctgca agtggatatt tggacctctc tgaggatttc gttggatacg     180
ggagaaaact cacctatcta aagagaagca ttctcagaac cttcttcg                  228
```

<210> SEQ ID NO 25
<211> LENGTH: 264
<212> TYPE: DNA
<213> ORGANISM: Homo sapiens

<400> SEQUENCE: 25

```
gctctgtgta aaggatcgtt caactctgtg agttgaatac acacaacaca aggaagttac      60
tgagaattct tctgtctagc cttatatgaa aaaaacccgt ttccaacgaa ggcctcaaag     120
aggtctgaat atccacttgc agactttaca aacagagtgt ttcctaactt gtgttgggtg     180
tgtttggggt ttctgagaat gcttctgtct agattttaac tgaagacaat cccgtttccc     240
```

```
acgaaatcct caaagctatg caaa                                          264
```

<210> SEQ ID NO 26
<211> LENGTH: 224
<212> TYPE: DNA
<213> ORGANISM: Homo sapiens

<400> SEQUENCE: 26

```
ggggtttcca cttttgcatc ttgcttattt tctcttgcca ctgccaatta agaagtgcct    60
tttgggcagg ggttgcaatc ctagtctctg ataaaacaga cttaaaacca acaaagatca   120
aaagagacaa agaaggtcat tacataatgg taaagggatc aattcaacaa gaagagctaa   180
ctatcctaaa tatatatgca cccaatacag gagcacccag attc                    224
```

<210> SEQ ID NO 27
<211> LENGTH: 199
<212> TYPE: DNA
<213> ORGANISM: Homo sapiens

<400> SEQUENCE: 27

```
gaataatgcc gcaataaaca tacgtgtgca tgtgtcttta tagcagcatg atttatagtc    60
cttgggtat atacccagta atgggatggc tgggtatata cctaaaggat tataaatcat    120
gctgctataa agacacatgc acacgtatgt ttattgcggc actattcaca atagcaaaga   180
cttggaacca acccaaatg                                                199
```

<210> SEQ ID NO 28
<211> LENGTH: 151
<212> TYPE: DNA
<213> ORGANISM: Homo sapiens

<400> SEQUENCE: 28

```
gtttataaag tctgcaagtg gatattcaga ccccctttgag gccttcgttg gaaacgggat   60
ttcttcatat tatgctagac agaagaattc tcagtaactt ccttgtgttg tgtgtattca   120
actgacagag ttgaacgatc ctttacctgt c                                  151
```

<210> SEQ ID NO 29
<211> LENGTH: 251
<212> TYPE: DNA
<213> ORGANISM: Homo sapiens

<400> SEQUENCE: 29

```
gtgttaaagt ctcccattat taacgtgtgg gagtctaagt ctctttgtag gtcactcagg    60
acttgcttta tgaatctggg tgctcctgta ttgggtgcat atatatttag gatagttagc   120
tcttcttgtt gaattgatcc ctttaccatt atgtaagacc ctctttctca agatctcatc   180
aaataaacac gaatggtcaa ccacaagaga aaagactgga gtcatcatca tgcccagaca   240
gacatttcat c                                                        251
```

<210> SEQ ID NO 30
<211> LENGTH: 221
<212> TYPE: DNA
<213> ORGANISM: Homo sapiens

<400> SEQUENCE: 30

```
gtttggaaac actctgtctg taaagtctgc aagcagatat ttggatctct ttgagcccctt   60
cgttggaaac ggggtttctt catattatgc tagacagaag aattctcagt aacttccttg   120
```

```
tgttgtgtgt attcaactca cagagttgaa cgatccttta cacagagcag acttgaaaca    180 ctcttttttgt ggaatttgca agtggagatt tcacaaaaaa c                       221
```

<210> SEQ ID NO 31
<211> LENGTH: 171
<212> TYPE: DNA
<213> ORGANISM: Homo sapiens

<400> SEQUENCE: 31

```
gctctgcgat gtgtgcgttc aactctcaga gtttaacttt tcttttcatt cagcagtttg    60
gaaacactct gtttgtaaag tctgcacgtg gataatttga ccacttagag gccttcgttg    120
gaaacgggat tcttcatat tctgctagac agaagaattc tcagaatctt c              171
```

<210> SEQ ID NO 32
<211> LENGTH: 284
<212> TYPE: DNA
<213> ORGANISM: Homo sapiens

<400> SEQUENCE: 32

```
agtctaagtc tctttgtagg tcactcagga cttgctttat gaatctgggt gctcctgtat    60
tgggtgcata tatatttagg atagttagct cttcttgttg aattgatccc tttaccatta    120
tgtaatggcc ttgtctcttt tgatctttgt tgggtgtgtt tgggttttttg ttttccattt   180 gcttggtaga tcttcctcca tccctttatt ttgagcctat gtgtgtctct gcacgtgaga    240
tgggtttcct gagtacagca cactgatggg tcttgactct atcc                    284
```

<210> SEQ ID NO 33
<211> LENGTH: 234
<212> TYPE: DNA
<213> ORGANISM: Homo sapiens

<400> SEQUENCE: 33

```
gtgttaaagt ctcccattat tattgtttgg gcgtctaagt ctctttgtag gtttctaagg    60
atctgcttta tgaatctagg tgctcctgta ttgggtgcac atatatttag gatagttagc    120
tcttcttgtt gaattgatcc ctttaccatt atgtaatggc cttctttgtc tcttttgatc    180
tttgttggtt taaagtctgt tttatcagag actaggattg caaccccaca ccaa         234
```

<210> SEQ ID NO 34
<211> LENGTH: 233
<212> TYPE: DNA
<213> ORGANISM: Homo sapiens

<400> SEQUENCE: 34

```
ggtggtgtgt gcgttcaact cacagagttt aacctttctt ttcatagagc agttaggaaa    60
cactctgttt gtaaactctg caagtggata ttcagacctc tttgaggcct tcgttggaaa    120
cgggatttct tcatactgtg ctagacagaa gaattctcag taacttcctt gtgttgtgtg    180
tattcaactc aaagaggtct gaatatccac ttgcagagtt tacaaacaga gtg           233
```

<210> SEQ ID NO 35
<211> LENGTH: 151
<212> TYPE: DNA
<213> ORGANISM: Homo sapiens

<400> SEQUENCE: 35

```
gacttgcttt atgaatctgg gtgctcctgt attgggtgca taaatattta ggatagttag    60
ctcctcttgt tgaattgatc cctttaccat tatgtaatgg ccttctttgt ctcttttgat    120
```

```
ctttgttgct ggccagggca atcaggcagg g                                   151
```

<210> SEQ ID NO 36
<211> LENGTH: 225
<212> TYPE: DNA
<213> ORGANISM: Homo sapiens

<400> SEQUENCE: 36

```
tttgtctagc tttgaggatt tcgttggaaa cgggattaca tataaaaagc agacagcggc    60
attcccagaa acttctttgt gatgtttgca ttcaagtcac agagttgaac attcccttcc   120
atagagcagg tttgaaacac tctttctgta gtatctggaa gtgaacatta ggacagcttt   180
caggtctatg gtgagaaagg aaatatcttc aaaaaaaaac caaac                    225
```

<210> SEQ ID NO 37
<211> LENGTH: 151
<212> TYPE: DNA
<213> ORGANISM: Homo sapiens

<400> SEQUENCE: 37

```
gtttggtggg ggaattcttc tgtctagcct tatatgaaaa aaacccgttt ccaacgaagg    60
cctcaaagag gtctgaatat ccacttgcag actttacaaa cagagtgttt cctaactgct   120
ctatgaaaag aaaggttaaa ctctgtgagt t                                   151
```

<210> SEQ ID NO 38
<211> LENGTH: 238
<212> TYPE: DNA
<213> ORGANISM: Homo sapiens

<400> SEQUENCE: 38

```
agttcaacca ttgtggaaga cagtgtggtg attcctcaag gatctagaac tagaaatacc    60
atttgaccca gccatcccat tactgggtat atacccaaag gattataaat gattctacta   120
taaagataca tgcacatgta tgtttattgt agcactcttc acaatagcaa agactgggaa   180
ccaacccaaa tgcccatcaa taatagactg gataaagaaa atgtggcaca tagatacc     238
```

<210> SEQ ID NO 39
<211> LENGTH: 290
<212> TYPE: DNA
<213> ORGANISM: Homo sapiens

<400> SEQUENCE: 39

```
acctttgact tcaaagcggc tgaaatctcc acttgcaaat tccacaaaaa gagtgttaca    60
agtctgctct gtgtaaagga tcgttcaact ctgtgagttg aatacacaca acacaaggaa   120
gttactgaga attcttctgt ctagccttac atgaaaaaaa cccgtttcca acgaaggcct   180
ctaagtggtc aaattatcca cgtgcagact ttacaaacag agtgtttcca aactgctgaa   240
tgaaagaaa agttaaactc tgagagttga acgcacacat cacaaaggag               290
```

<210> SEQ ID NO 40
<211> LENGTH: 244
<212> TYPE: DNA
<213> ORGANISM: Homo sapiens

<400> SEQUENCE: 40

```
cccattatta ttgtgtggga gtctaagtct ctttataggt ctctaaggac ttgctttatg    60
aatctgggtg ctcctgtgtt gggtgtgttt ggttttttgt tgaattgatc cctttaccat   120
```

```
tatgtaatga caaagaaggc cattacataa tggtaaaggg atcaattcaa caagaagagc    180
taactatcct aaatatatat gcacccaata caggagcacc cagattcata aagcaagtcc    240
ttag                                                                 244

<210> SEQ ID NO 41
<211> LENGTH: 151
<212> TYPE: DNA
<213> ORGANISM: Homo sapiens

<400> SEQUENCE: 41
ggattattcc attccattcc attagatgat tccattcggg tccattcgat gattctcttc     60
gattccattc gataattccg ttttttttccg tttgatgttg attccattcg attccattcg   120
atgataattc cattcgattc tatgcgatga t                                   151

<210> SEQ ID NO 42
<211> LENGTH: 172
<212> TYPE: DNA
<213> ORGANISM: Homo sapiens

<400> SEQUENCE: 42
ggatcgttca actctgtgag ttgaatacac acaacacaag gaagttactg agaattcttc     60
tgtctagcag aatatgaaga atcccgtttt ccaacgaagg cctcaaaggg gtctaactaa    120
tcacttgcag actttacaga cagagtcttt ccaaactgct ctatgaagag aa            172

<210> SEQ ID NO 43
<211> LENGTH: 228
<212> TYPE: DNA
<213> ORGANISM: Homo sapiens

<400> SEQUENCE: 43
gacgtttctg agaatgcttc tgtctagatt tgatatgaag atattcccgt ttccaacgaa     60
atcttcaaat ctatccaaat gtccacttgc agattcaaca aaaagtgttt ttcagaactg    120
ctctatcaaa agaatggatc aacactgtta gttgagtacc cacatcacaa acgtgattct    180
ttgcgatgtt tgcattcaac tcatagagtt gaacattccc tttgagag                 228

<210> SEQ ID NO 44
<211> LENGTH: 151
<212> TYPE: DNA
<213> ORGANISM: Homo sapiens

<400> SEQUENCE: 44
gaatcgaatg gaatcatcga atggactcga atggaataat cattgaacgg aatcgaatgg     60
aatcatcatc ggatggaaat gaatggaatc atcatcgaat ggaatcgaat agaattatgg    120
aatgaaatcc agtgtgatca tcatcgaatg g                                   151

<210> SEQ ID NO 45
<211> LENGTH: 274
<212> TYPE: DNA
<213> ORGANISM: Homo sapiens

<400> SEQUENCE: 45
aacattccgt ttcagagagc agctttgagg cactcttttt gtagtatgtg caagtggata     60
tttggagcgc tctgaggcct acggtgaaaa agcaaatatc ttcccataac caccagacag    120
aaacattctc agaaactcct ttatgacgta tgcactcacc taacagaaaa gtccacttcc    180
atatactaca aaaagagcgt ttcaaacctg ctctatgaaa ggcaatgttc aactctgtga    240
```

```
cttgaatgca gacatcacag agcagtttct gaga                                    274
```

<210> SEQ ID NO 46
<211> LENGTH: 245
<212> TYPE: DNA
<213> ORGANISM: Homo sapiens

<400> SEQUENCE: 46

```
agatatagaa aaggcctttg acaaaattca acaactcttc atgctataaa ctctcagtaa         60
attaggtatg gatgggaaat atctcaaaat aataggagct atctatgaca aacccacagc        120
caatatcata ctgaatgggc aaaaactggg agcattccct ttgaaaactg cacaagaca        180 gggatgccct ctctcaccac tcctattcaa catagtgttg aagttctgg ccagggcaat        240 taggc                                                                    245
```

<210> SEQ ID NO 47
<211> LENGTH: 151
<212> TYPE: DNA
<213> ORGANISM: Homo sapiens

<400> SEQUENCE: 47

```
attcatttcc atccgatgat gattccattc gattccgttc aatgattatt ccattcgagt         60
ccattcgatg attccattcg attccattcg atgatgattg cattcgagtc catggattat        120
tccattccat tccattagat gattccattc g                                       151
```

<210> SEQ ID NO 48
<211> LENGTH: 151
<212> TYPE: DNA
<213> ORGANISM: Homo sapiens

<400> SEQUENCE: 48

```
aagaattttc tgagaatgat tctgtctggt ttcttcctat agaaactaga cagaatgatt         60
ctcagaaact cctttgtgat gtgtgcgttc aactcacata gtttaacctt tcttttcata        120
gagcagtttg gaaacactct gtttgtaaag t                                       151
```

<210> SEQ ID NO 49
<211> LENGTH: 200
<212> TYPE: DNA
<213> ORGANISM: Homo sapiens

<400> SEQUENCE: 49

```
tcaacaccac cttcttcgac cccgccggag gaggagaccc cattctatac caacacctat         60
tctgattttt cggtcaccct gaagtttata ttcttatcct accaggcttc ggaataatct        120
cccatattgt aacttactac tccggaaaaa agaaccatt tggatacata ggtatggtct        180
gagctatgat atcaattggc                                                    200
```

<210> SEQ ID NO 50
<211> LENGTH: 200
<212> TYPE: DNA
<213> ORGANISM: Homo sapiens

<400> SEQUENCE: 50

```
gtggatattc ggacctcttt gaggccttcg ttggaaacgg gatttcttca tattatgcta         60
gacagaagat ttctcagtaa cttctttgcg ttgtgtgtat gcaactcaca gagttcaacc        120
ttcctttaga cagagcagat ttgaaacact cttttttgtgg aatttgcaag tggagatttc       180
```

```
aagcgcttcg atgccaatgg                                               200
```

<210> SEQ ID NO 51
<211> LENGTH: 200
<212> TYPE: DNA
<213> ORGANISM: Homo sapiens

<400> SEQUENCE: 51

```
gaaccatttg gatacatagg tatggtctga gctatgatat caattggctt cctagggttt   60
atcgtgtgag cacaccatat atttacagta ggaatagacg tagacacacg agcatatttc  120
acctccgcta ccataatcat cgctatcccc accggcgtca aagtatttag ctgactcgcc  180
acactccacg gaagcaatat                                              200
```

<210> SEQ ID NO 52
<211> LENGTH: 150
<212> TYPE: DNA
<213> ORGANISM: Homo sapiens

<400> SEQUENCE: 52

```
acagaacagg ctcctctaga gggatatgaa gcaccgccag gtccttgag ttttaagctg    60
tggctcgtag tgttctggcg agcagttttg ttgatttaac tgttgaggtt tagggctaag  120
catagtgggg tatctaatcc cagtttgggt                                   150
```

<210> SEQ ID NO 53
<211> LENGTH: 200
<212> TYPE: DNA
<213> ORGANISM: Homo sapiens

<400> SEQUENCE: 53

```
caataacttg accaacggaa caagttaccc tagggataac agcgcaatcc tattctagag   60
tccatatcaa caatagggtt tacgacctcg atgttggatc aggacatccc gatggtgcag  120
ccgctattaa aggttcgttt gttcaacgat taaagtccta cgtgatctga gttcagaccg  180
gagtaatcca ggtcggtttc                                              200
```

<210> SEQ ID NO 54
<211> LENGTH: 200
<212> TYPE: DNA
<213> ORGANISM: Homo sapiens

<400> SEQUENCE: 54

```
caactaggac tcataatagt tacaatcggc atcaaccaac cacacctagc attcctgcac   60
atctgtaccc acgccttctt caaagccata ctatttatgt gctccgggtc catcatccac  120
aaccttaaca atgaacaaga tattcgaaaa ataggaggac tactcaaaac catacctctc  180
acttcaacct ccctcaccat                                              200
```

<210> SEQ ID NO 55
<211> LENGTH: 200
<212> TYPE: DNA
<213> ORGANISM: Homo sapiens

<400> SEQUENCE: 55

```
ctggcatttt gtagatgtgg tttgactatt tctgtatgtc tccatctatt gatgagggtc   60
ttactcttt agtataaata gtaccgttaa cttccaatta actagttttg acaacattca   120
aaaaagagta ataaacttcg ccttaatttt aataatcaac ccctcctag ccttactact   180
aataattatt acattttgac                                              200
```

<210> SEQ ID NO 56
<211> LENGTH: 200
<212> TYPE: DNA
<213> ORGANISM: Homo sapiens

<400> SEQUENCE: 56

```
aatcattttt attgccacaa ctaacctcct cggactcctg cctcactcat ttacaccaac    60
cacccaacta tctataaacc tagccatggc catcccctta tgagcgggcg cagtgattat   120
aggctttcgc tctaagatta aaaatgccct agcccacttc ttaccacaag gcacacctac   180
accccttatc cctatactag                                              200
```

<210> SEQ ID NO 57
<211> LENGTH: 200
<212> TYPE: DNA
<213> ORGANISM: Homo sapiens

<400> SEQUENCE: 57

```
tattcgagcc gagctgggcc agccaggcaa ccttctaggt aacgaccaca tctacaacgt    60
tatcgtcaca gcccatgcat ttgtaataat cttcttcata gtaataccca tcataatcgg   120
aggctttggc aactgactag ttcccctaat aatcggtgcc cccgatatgg cgtttccccg   180
cataaacaac ataagcttct                                              200
```

<210> SEQ ID NO 58
<211> LENGTH: 218
<212> TYPE: DNA
<213> ORGANISM: Homo sapiens

<400> SEQUENCE: 58

```
atattctgtt gatttggggt ggagagttct gtagatgtct attaggtcca cttggtgcag    60
agctgagttc aattcctggg tatccttgtt gactttctgt ctcattgatc tgtctaatgt   120
tgacagtggg gtgttaaagt ctcccattat taatgtatgg gagtctaagt ctctttgtag   180
atcactcagg acttgcttta tgaatctggg tgctcctg                           218
```

<210> SEQ ID NO 59
<211> LENGTH: 256
<212> TYPE: DNA
<213> ORGANISM: Homo sapiens

<400> SEQUENCE: 59

```
atatgaactt taaagtagtt ttttccaatt ctgtgaagaa agtcattggt agcttgatgg    60
ggatggcatt gaatctataa attaccttgg gcagtatggc cattttcatg atattgattc   120
ttcctatcca tgagcatgga atgttccatt tgtttgtgtc ctcttttatt tcattgagca   180
gtggttcgta gttctccttg aagagtcctt cacatccctt gtaaggtgga ttcctaggta   240
ttttattctc tgaagc                                                  256
```

<210> SEQ ID NO 60
<211> LENGTH: 248
<212> TYPE: DNA
<213> ORGANISM: Homo sapiens

<400> SEQUENCE: 60

```
agagaataaa atacctagga atccaactta caagggatgt gaaggacctc ttcaaggaga    60
actacaaact gctactcaag gaaatagaag aggatacaaa caaatggaag atattccat   120
```

```
gctcatgggt aggaagaatc aatatcgtga aaatggccat actgcccaag gtaatttaca      180
gattcaatgc catccccatc aagctaccaa tgactttctt cacagaattg gaaaaaacta      240
ctttaaag                                                               248

<210> SEQ ID NO 61
<211> LENGTH: 277
<212> TYPE: DNA
<213> ORGANISM: Homo sapiens

<400> SEQUENCE: 61
accttgggca gtatggccat tttcaggata ttgattcttc ctacccatga gcatggaatt       60
ttcttccatt tgtttgtatc ctcttttatt tcactgagca gtggtttgta gttctccttg      120
aagaggtcct tcacatccct tgtaagttgg attcctaggt attttattct ctttgaagca      180
attgtgaatg ggagttcact catgatttgg ctctctgtct gttgttggtg tataagaatg      240
cttgtgattt ttgtacattg attttgtatc ctgagac                               277

<210> SEQ ID NO 62
<211> LENGTH: 232
<212> TYPE: DNA
<213> ORGANISM: Homo sapiens

<400> SEQUENCE: 62
cctattcaac ataatgttgg aagttctagc caggacaatc aggcaggaga agaaataaa        60 gggtactcaa ttaggaaaag aggaagtcaa attgtccctg tatgcagata acatgattgt      120
atatttagaa aaccccatca tctcagccca aaatctcctt aagctgataa gcaacttcag      180
caaagtctca ggatacaaaa tcaatgtgca aaaatcacaa gcattcctat ac              232

<210> SEQ ID NO 63
<211> LENGTH: 270
<212> TYPE: DNA
<213> ORGANISM: Homo sapiens

<400> SEQUENCE: 63
ctttaaagta gttttttcca attctgtgaa gaaagtcatt ggtagcttga tggggatggc       60
attgaatcta taaattacct tgggcagtat ggccattttc atgatattga ttcttcctat      120
ccatgagcat ggaatgttct tccatttgtt tgtgtcctct tttattttgt tgaacagtgg      180
tttgtagttt tccttgaaaa ggtgcttcgc attccttgta agttggattc ctagatattt      240
tattctcttt gtagcaattg tgaatgggag                                       270

<210> SEQ ID NO 64
<211> LENGTH: 210
<212> TYPE: DNA
<213> ORGANISM: Homo sapiens

<400> SEQUENCE: 64
atgttcttcc atttgtttgt ctcctctttt atttccttga gcagtggttt gtagttctcc       60
ttgaagaggt ccttcacatc ccttgtaagt tggattccta ggtatttttat tctctttgaa     120 gcaattgtga atgggagttc acccatgatt tggctctctg tttgtctgtt gttggtgtat      180
aagaatgctt gtgattttg tacattgatt                                        210

<210> SEQ ID NO 65
<211> LENGTH: 206
<212> TYPE: DNA
<213> ORGANISM: Homo sapiens
```

<400> SEQUENCE: 65

```
cacaataata atgggagact ttaacacccc actgtcaaca ttagacagat caatgagaca      60
gaaagttaac aaggataccc aggaattgaa ctcagctctg caccaagcag acccaataga     120
catctacaga actctccacc ccaaatcaac agaatataca tcttttttcat caccacacct    180
attgcaaaat tgaccacata gttgga                                          206
```

<210> SEQ ID NO 66
<211> LENGTH: 243
<212> TYPE: DNA
<213> ORGANISM: Homo sapiens

<400> SEQUENCE: 66

```
ctgtgatctg agagcctgtt tgttatgatt tctgttcttt tccatttgct gacgagtgtt      60
ttgcttccaa ttatgtggtt gattttagaa taagtgctat gtggtgctga agaatata       120
tattctgttg atttggggtg gagagttctg tagatgtcta ttaggtccac ttggtgcaga     180
gctgagttca attcctggat atccttgtta actttctgtc tcgttgatct gtctaatgtt    240
gac                                                                   243
```

<210> SEQ ID NO 67
<211> LENGTH: 213
<212> TYPE: DNA
<213> ORGANISM: Homo sapiens

<400> SEQUENCE: 67

```
tgccatcccc atcaagctac caatgacttt cttcacagaa ttggaaaaaa ctactttaaa      60
gttcatatgg aaccaaaaaa gagcctgcat tgccaagtca atcctaagcc aaaagaacaa     120
agctggaggc atcatgctac ctgacttcaa actatactac aagattacag taaccaaaac    180
agcatggtac tggtaccaaa acagagatat aga                                  213
```

<210> SEQ ID NO 68
<211> LENGTH: 188
<212> TYPE: DNA
<213> ORGANISM: Homo sapiens

<400> SEQUENCE: 68

```
ttttggtatc agtaccatgc tgttttggtt actgtagcct tgtagtatag tttgaagtca      60
ggtagcgtga tgcctccagc tttgttcttt tggcttagga ttgacttggc gatgcgggct    120
ctttttttggt tccatatgaa ctttaaagta gttttttcca gttctgtgaa gaaagtcatt    180
ggtagctt                                                              188
```

<210> SEQ ID NO 69
<211> LENGTH: 262
<212> TYPE: DNA
<213> ORGANISM: Homo sapiens

<400> SEQUENCE: 69

```
ctgtagcctt gtagtatagt ttgaagtcag gtagtgtgat gcctccggct ttgttctttt      60
ggcttaggat tgacttggca atgcggggtc tttttttggtt ccatatgaac tttaaagtag    120
ttttttccaa ttctgtgaag aaagtcattg gtagcttgat ggggatggca ttgaatctat    180
aaattacctt gggcagtatg gccattttca cgatattgat tcttcctatc catgagcatg    240
gaatgttctt ccatttgttt gt                                              262
```

<210> SEQ ID NO 70
<211> LENGTH: 191
<212> TYPE: DNA
<213> ORGANISM: Homo sapiens

<400> SEQUENCE: 70
aaataaaaga agacacaaat aaatggaaga acattccata ctcgtggata ggaagaatca    60
atattgtgaa atggccata ctgcccaagg taatttatag attcaatgcc atccccatca   120
agctaccaat gactttcttc acagaattgg aaaaaactac tttaaagttc atatggaacc   180
aaaaaacagc c                                                       191

<210> SEQ ID NO 71
<211> LENGTH: 247
<212> TYPE: DNA
<213> ORGANISM: Homo sapiens

<400> SEQUENCE: 71
ccctctctca ccactcccat tcaacatagt attggaagtt ctggccacag caatcacgca    60
agagaaagaa ataaagagta ttcaagtagg aaaagaggaa gtcaaattgt ccctgtttgc   120
agatgacatg attgtatatc tagaaaaccc catcatctca gcccaaaatc tccttaagct   180
gataagcaac ttcagcaaag tctcaggata caaaatcaat gtgcaaaaat cacaagcatt   240
cctatac                                                            247

<210> SEQ ID NO 72
<211> LENGTH: 199
<212> TYPE: DNA
<213> ORGANISM: Homo sapiens

<400> SEQUENCE: 72
ataagcaact tcagcaaagt ctcaggacac aaaatcaatg tacaaaaatc acaagcattc    60
ttatacacca ataacagaca aacagagagc caaatcatga gtgaactccc attcacaatt   120
gcttcaaaga gaataaaata cttaggaatc caacttacaa gggacgtgaa ggacctcttc   180
aaggagaact acaaaccac                                               199

<210> SEQ ID NO 73
<211> LENGTH: 279
<212> TYPE: DNA
<213> ORGANISM: Homo sapiens

<400> SEQUENCE: 73 ctctttttttg gtacaagtac catgctgttt tggttactgt agccttgtag tatagtttga    60
agtcaggtag catgatgcct ccagctttgt tcttttttact tagcattgtc ttggcaatgt   120
gtgctgtttt ttggttccat atggactttta aagtagtttt ttccaattct gtgaagaaag   180
tcattggtag cttgatgggg atggcattga atctataaat taccttgggc agtatggcca   240
ttttcatgat attgattctt cctatccatg agcatggaa                         279

<210> SEQ ID NO 74
<211> LENGTH: 282
<212> TYPE: DNA
<213> ORGANISM: Homo sapiens

<400> SEQUENCE: 74
ataagaatgc ttgtgatttt tgcacattga ttttgtatcc tgagactttg ctgaagttgc    60
ttatcagctt aaggagattt tgggctgaga cgatggggtt ttctagatat acaatcatgt   120

| | |
|---|---|
| catctgcaaa cagcgacaat ttgacttcct cttttcctaa ttgaataccc tttatttcct | 180 |
| tctcctgttt cattgccctg gccagaactt ccaacactat gttgaatagg agtggtgaga | 240 |
| gagggtgtcg ctgtgttgtg ccagctttca aagggaatgc tt | 282 |

<210> SEQ ID NO 75
<211> LENGTH: 253
<212> TYPE: DNA
<213> ORGANISM: Homo sapiens

<400> SEQUENCE: 75

| | |
|---|---|
| tttgattgca ctgtggtctg agagacagtt ggttgtgatt tctgttcttt tacatttgct | 60 |
| gaggagtgct ttacttccaa ctatgtggtc agttttggaa taaatgtggt gtggtgctga | 120 |
| aaaaaatgta tattctgttg atttggggta gagagttctg tagatgtcta ttaggtctgc | 180 |
| ttggtgcaga gctgagttca attcctgggt atccttgttg actttctgtc tcgttgatct | 240 |
| gtctaatgtt gac | 253 |

<210> SEQ ID NO 76
<211> LENGTH: 283
<212> TYPE: DNA
<213> ORGANISM: Homo sapiens

<400> SEQUENCE: 76

| | |
|---|---|
| accccactgt caacattaga cagatcaacg agacagaaag ttaacaagga tatccaggaa | 60 |
| ttgaactcag ctctgcacca agcggaccta atagacatct acagaactct ccaccccaaa | 120 |
| tcaacagaat atacattctt ctcagcactg catcgcactt attccgaaat tgaccacata | 180 |
| gttggaagta aagccctcct cagcaaatgt aaaagaacag aaattataac aaactgtctc | 240 |
| tcagaccaca gtgcaatcaa actagaactc aggattaaaa aac | 283 |

<210> SEQ ID NO 77
<211> LENGTH: 211
<212> TYPE: DNA
<213> ORGANISM: Homo sapiens

<400> SEQUENCE: 77

| | |
|---|---|
| aaaacagcat ggtactggta ccaaaacaga gatatagacc aatggaacag aacagagccc | 60 |
| tcagaaataa taccacacat ctacaaccat ctgatctttg acaaacctga caaaaacaag | 120 |
| aaatggggaa aggattccct atttaacaaa tggtgctggg aaaactggct agccatatgt | 180 |
| agaaagctga aactggatcc cttccttaca c | 211 |

<210> SEQ ID NO 78
<211> LENGTH: 172
<212> TYPE: DNA
<213> ORGANISM: Homo sapiens

<400> SEQUENCE: 78

| | |
|---|---|
| caaatggaag aacattccat gctcatgggt aggaagaatc aatatcgtga aaatggccat | 60 |
| actgcccaag gtaatttaca gattcaatgc catccccatc aagctaccaa tgactttctt | 120 |
| cacagaattg gaaaaaacta ctttaaagtt catatggaac caaaaagag cc | 172 |

<210> SEQ ID NO 79
<211> LENGTH: 192
<212> TYPE: DNA
<213> ORGANISM: Homo sapiens

```
<400> SEQUENCE: 79
atttcgttga gcagtggttt gtagttctcc ttgaagaggt ccttcacatc ccttgtaagt    60
tggattccta ggtattttat tctctttgaa gcaattgtga atgggagttc actcatgatt   120
tggctctctg tctgttattg gtgtatagga atgcttgtga tttttgcaca ttgattttgt   180
tatcctgaga ct                                                      192

<210> SEQ ID NO 80
<211> LENGTH: 254
<212> TYPE: DNA
<213> ORGANISM: Homo sapiens

<400> SEQUENCE: 80
ggtaatttat agattcaatg ccatccccat caagctacca atgactttct tcacagaatt    60
ggaaaaaact actttaaagt tcatatggaa ccaaaaaaga gcccgcattg ccaagacaat   120
cctaagccaa agaacaaag ctggaggcat cacactacct gacttcaaac tatactacaa    180
ggctacagta accaaaacag catggtactg gtaccaaaac agagatatag accaatggaa   240
caggatagag ccct                                                    254

<210> SEQ ID NO 81
<211> LENGTH: 300
<212> TYPE: DNA
<213> ORGANISM: Homo sapiens

<400> SEQUENCE: 81
atcacaaaca agtttctgag aatgcttctg tctagttttt atgggaagat atttcctttt    60
tcatcatagg cctcaaagcg ctccaaatgt ccacttccag atagtgcaga aagagtgtct   120
caaacctggt atataaaagg gaacattcta ctctgtgact tgaatgaaaa catcacaaag   180
cagtttctga gaatgcttcc gtctagattt tatatgaaga tattcccgtt tccaacgaaa   240
ccttcaaagc tatccgaata tccacctgca gattctacaa aaagagtgtt tccaaaatgc   300

<210> SEQ ID NO 82
<211> LENGTH: 300
<212> TYPE: DNA
<213> ORGANISM: Homo sapiens

<400> SEQUENCE: 82
tcccgtttcc aacgaaatcc tcaaagctat ccaaatatcc actttcagat tccacaaaaa    60
gagtgtttca aaactgctct gtaaaaagaa aggttcatct ctgttagttg aatacacaca   120
tcacaaacaa gtttctgaga atgcttctgt ctagttttta tgggaagata tttcctttt    180 caacataggc tcaaagcgc tccaaatgtc cacttccagg tagtgcagaa agagtgtttc    240
aaacctgctc tataaaaggg aatattcaac tctgtgactt gaatgcaaac atcacaaagc   300

<210> SEQ ID NO 83
<211> LENGTH: 300
<212> TYPE: DNA
<213> ORGANISM: Homo sapiens

<400> SEQUENCE: 83
aaacctgctc tataaaaggg aatattcaac tctgtgactt gaatgcaaac atcacaaagc    60
actttctgag aatgcttccg tctagatttt atatgaagat attcccgttt ccaaggaaat   120
cttcctagct atctaaatat caacttgcag attctactaa aggtatgttt ccaaaatgct   180
gtatccacac aaaggttcaa ctctgttaat tgaggacata catcgcaaat aagtttctga   240
```

```
gaatgcttct gtctagattt tatatgaaga tattccgttt tcaccacagg cctgaaagcg      300
```

<210> SEQ ID NO 84
<211> LENGTH: 300
<212> TYPE: DNA
<213> ORGANISM: Homo sapiens

<400> SEQUENCE: 84

```
ttttctaccg ttggcctcaa agcgcttgaa gtctccccct gaaaattcca caaaaagtgt       60
ttccaatctg ctccgtctaa aggaagcttc aactctgtga gttgaatacc cacaacacaa      120
agaagttact gagaattctt ctgtctcgca ttatatgaag aaatcccgtt tccaactaag      180
gcctcaaata catccacata tccagttgct gactttacaa actgagtgtt tccaaactgc      240
tctatgaaaa gaaaggttaa acactgtgag ttgaacacac acgtaccaaa gtagtttctg      300
```

<210> SEQ ID NO 85
<211> LENGTH: 300
<212> TYPE: DNA
<213> ORGANISM: Homo sapiens

<400> SEQUENCE: 85

```
ggaagatatt tcctttttca tcataggcct caaagcgctc caaatgtcca cttccagata       60
gtgcagaaag agtgtctcaa acctggtata taaagggaa cattctactc tgtgacttga      120
atgaaaacat cacaaagcag tttctgagaa tgcttccgtc tagattttat atgaagatat      180
tcccgtttcc aacgaaacct tcaaagctat ccgaatatcc acctgcagat tctacaaaaa      240
gagtgtttcc aaaatgccgt atcaaaacaa aggttcaact ctgttagttg agaacacaca      300
```

<210> SEQ ID NO 86
<211> LENGTH: 300
<212> TYPE: DNA
<213> ORGANISM: Homo sapiens

<400> SEQUENCE: 86

```
gatatttcct tttctacatg tggcctaaat gtgcttgaaa tctccatctg caaatatcac       60
agaaagagtg tttcacatct gctctgtcta aggaatgtt caactctgtg agttgaatac      120
acacaacaca aagaagttac ggagaattat tctgtctggc attatatgaa gaaatcccgt      180
tccaacgaa ggactcaaag aggtccatat atccacttgc agaatttaca agagagtgt      240
ttccaaactg ctcaatcaaa agaaaggtta aactctgtga attgaacgca cacatcacaa      300
```

<210> SEQ ID NO 87
<211> LENGTH: 300
<212> TYPE: DNA
<213> ORGANISM: Homo sapiens

<400> SEQUENCE: 87

```
ccacttgcag attctacaaa aagagtgttt ccaaactgct gtatcaaaag aaaggttcaa       60
ctctgttagt tgaggacaca catcacaaat aagtttctga gaatccttct gtctagtttt      120
tatgggaaga tatttccttt ttcaccatga gcctgaaagc gctcgaaacg tccacttcca      180
gatactcag aaagagtgtt tcaaacctgc tctatgaatg cgaatgttca actctgtgac      240
ttaaaagcaa acatcacaaa gaagcttctg agaatgctgc tgtctacttt ttatatgtaa      300
```

<210> SEQ ID NO 88
<211> LENGTH: 300
<212> TYPE: DNA

<213> ORGANISM: Homo sapiens

<400> SEQUENCE: 88

| aagaagtttc tgtgaatgat gctgtctaga ttttataaga agatgtttcc ttttctacca | 60 |
| taggcctcaa agcgctagaa atctccagct gcaaattcca caaaaagtgt gtttaacatc | 120 |
| tgctctgtct aaagtaaagt tcagctctgt gagtagaata cacacagcac aaagaagtta | 180 |
| ctgagacttc ttctgtctaa cattatatga agaaatcccg tttccaacga aggcctcaaa | 240 |
| gaggtccaaa tatccacttg cagacttgtc agagtgtttc caaactgcac catcaaaaga | 300 |

<210> SEQ ID NO 89
<211> LENGTH: 300
<212> TYPE: DNA
<213> ORGANISM: Homo sapiens

<400> SEQUENCE: 89

| tatgaagaaa tcccgtttcc aacgaaggcc tcaagagggt ccaaatatcc acttgcagac | 60 |
| attaaaaaca gagtgtttcc aaactgctca gtcaaaagaa aggctaaaact cagtgagttg | 120 |
| aatgcacaca tcacaaagta cttctctgaga atgattctgt ttagtgttta acgaagata | 180 |
| tttcctttc tacacttggc ctaaaaacgc ttgaaatctc cacctgcaaa tttcacaaaa | 240 |
| agagtttttc aaatctgctc tgtctaaaga aaggttcaac tcactgagtt gaatacacac | 300 |

<210> SEQ ID NO 90
<211> LENGTH: 200
<212> TYPE: DNA
<213> ORGANISM: Homo sapiens

<400> SEQUENCE: 90

| agaaaggttc atctctgtta gttgaataca cacatcacaa acaagtttct gagaatgctt | 60 |
| ctgtctagtt tttatgggaa gatatttcct ttttcatcat aggcctcaaa gcgctccaaa | 120 |
| tgtccacttc cagatagtgc agaaagagtg tctcaaacct ggtatataaa agggaacatt | 180 |
| ctactctgtg acttgaatga | 200 |

<210> SEQ ID NO 91
<211> LENGTH: 200
<212> TYPE: DNA
<213> ORGANISM: Homo sapiens

<400> SEQUENCE: 91

| ccttttctac cgttggcctc aaagcgcttg aagtctcccc ctgaaaattc cacaaaaagt | 60 |
| gtttccaatc tgctccgtct aaaggaagct tcaactctgt gagttgaata cccacaacac | 120 |
| aaagaagtta ctgagaattc ttctgtctcg cattatatga agaaatcccg tttccaacta | 180 |
| aggcctcaaa tacatccaca | 200 |

<210> SEQ ID NO 92
<211> LENGTH: 200
<212> TYPE: DNA
<213> ORGANISM: Homo sapiens

<400> SEQUENCE: 92

| tcacaaagca gattctgata atgcttctgt ctaattttta tataaagata ttcctgtttc | 60 |
| caatgaaatc ctcaaagcta ttcaaatatc cacttgcaga ttatacaaaa accgtgtttc | 120 |
| aaaactacca aaataaatgt tcaactctgt tctttgagta cactcatcat aaacaagttt | 180 |
| ctgagaaggc ttctgtcaat | 200 |

<210> SEQ ID NO 93
<211> LENGTH: 200
<212> TYPE: DNA
<213> ORGANISM: Homo sapiens

<400> SEQUENCE: 93

```
gtttcaaaac tgctctatga aacgaatgtt caaccctgtg acgtgaatgc agacatcaca      60
aagcagtttc tgagaatgct tctgtctcga ttttacatga agatattccc gtttccaaag     120
aaatcttcaa agttatccaa atatccactt gcagattcta caaaaagagt gtttccaaac     180
tgctgtatca aaagaaaggt                                                 200
```

<210> SEQ ID NO 94
<211> LENGTH: 212
<212> TYPE: DNA
<213> ORGANISM: Homo sapiens

<400> SEQUENCE: 94

```
gcacacgtat gtttatcgca gcactactca caacaacaaa gacttggaac caacccaaat      60
gtccaccaat gatagactgg attaagaaaa tgtggcacat atacaccatg gaatactatg     120
cagccataaa aaatgatgag ttcatgtcct ttgtagggac atggatgaag ctggaaacca     180
tcattctcag caaactattg caaggacaaa aa                                   212
```

<210> SEQ ID NO 95
<211> LENGTH: 270
<212> TYPE: DNA
<213> ORGANISM: Homo sapiens

<400> SEQUENCE: 95

```
ttttttttg agacggagtc tcgctctgtc gcccaggctg gagtgcagtg gcgcaatctc       60
ggctcactgc aagctccgcc tcccgggttc aacgccattc tcctgcctca gcttcccaag     120
tagctgggac tacaggcgcc cgccactacg gccggctaat ttttttgtatt tttagtagag    180
acggggtttc accgttttag ccgggatggt ctcgatctcc tgacctcgtg atccgcccgc     240
ctcggcctcc caaagtgctg ggattatagg                                      270
```

<210> SEQ ID NO 96
<211> LENGTH: 135
<212> TYPE: DNA
<213> ORGANISM: Homo sapiens

<400> SEQUENCE: 96

```
catgtgtctt tatagcagca tgatttataa tcctttgggt atatacccag taatgggatg      60
gctgggtcaa atggtatttc tagttctaga tccttgagga attgccacac tgtcttccac     120
actggttgaa ctagt                                                      135
```

<210> SEQ ID NO 97
<211> LENGTH: 273
<212> TYPE: DNA
<213> ORGANISM: Homo sapiens

<400> SEQUENCE: 97

```
tgtgtccatg tgttctcatt gttcgattcc cacctatgag tgagaatatg tggtgtttgg      60
ttttttgtcc ttgtgatagt ttgctgagaa tgatggtttc cagcttcacc catgtcccta    120
caaaggacat gaactcatca ttttttatgg ctgcatagta ttccatggtg tatatgtgcc    180
```

```
acattttctt aatccagtct atcattgttg gacatttggg ttggttccaa gtctttgcta      240
tgtgaataat gccgcaataa acatacgtgt gca                                   273

<210> SEQ ID NO 98
<211> LENGTH: 164
<212> TYPE: DNA
<213> ORGANISM: Homo sapiens

<400> SEQUENCE: 98
tcccacagaa taataatggg agaatttgat acgccactgt caacattaga cagatcaacg       60
agacagaaag ttaacaagga tatccaggaa ttgaactcag cactgcacca agcagaccta      120
atagacatct acagaactct ccacaccaaa tcaacagaat atac                       164

<210> SEQ ID NO 99
<211> LENGTH: 102
<212> TYPE: DNA
<213> ORGANISM: Homo sapiens

<400> SEQUENCE: 99
tggctggtac cagttgttcc tttccatgtt tagtgcttcc ttcaggagct cttttagggc       60
aggcctggtg gtgacaaaat ctctcagcat ttgcttgtct gt                         102

<210> SEQ ID NO 100
<211> LENGTH: 232
<212> TYPE: DNA
<213> ORGANISM: Homo sapiens

<400> SEQUENCE: 100
tttttgttgc gatagtttac tgagaatgat ggtttccaat ttcatccatg tccctacaaa       60
ggacatgaac tcatcatttt ttatggctgc atagtattcc atggtgtata tgtgccacat      120
tttcttaatc cagtctatca ttgttggaca tttgggttgg ttccaagtct ttgctattgt      180
gaataatgcc gcaataaaca tacgtgtgca tgtgtcttta gagcagcatg at              232

<210> SEQ ID NO 101
<211> LENGTH: 133
<212> TYPE: DNA
<213> ORGANISM: Homo sapiens

<400> SEQUENCE: 101
ctctatactt cccttctcgc ttcatttcat tcatttcatc ttccattgct gatacccttt       60
cttccagttg atcgcatcgg ctcctgaggc ttctgcattc ttcacgtagt tctcgagcct      120
tggttttcag ctc                                                         133

<210> SEQ ID NO 102
<211> LENGTH: 286
<212> TYPE: DNA
<213> ORGANISM: Homo sapiens

<400> SEQUENCE: 102
atggtgtata tgtgccacat tttcttaatc cagtctatca ttgttggaca tttgggttgg       60
ttccaaatct ttgctattgt gaataatgcc gcaaaaaaca tacatgtgcg tgtgtcttta      120
tagcagcatg atttatattc ctttgggtat atacccagta atgggatggc tgggtcaaat      180
ggtatttcta gttctagatc cctgaggaat tgccacactg acttccacaa tggttgaact      240
agtttacagt cccaccaaca gtgtaaaagt gttcctattt ctccac                     286
```

```
<210> SEQ ID NO 103
<211> LENGTH: 231
<212> TYPE: DNA
<213> ORGANISM: Homo sapiens

<400> SEQUENCE: 103
aggcatgggc aaggatttca agactaaaac accaaaagca atggcaacaa aagctaatat      60
tgacaaatgg gatctaatta aactaaagag cttctgcaca gcaaaagaaa ctaccatcag     120
agtgaacagg caacctacag aatgggagaa aattttttgca atctactcat ctgacaaagg    180
gctaatatcc ggaatctaca atgaactcaa acaaatttac aaaaaaaaac c             231

<210> SEQ ID NO 104
<211> LENGTH: 270
<212> TYPE: DNA
<213> ORGANISM: Homo sapiens

<400> SEQUENCE: 104
gtttctgctg agggatctgc tcttagtcta atgggcttcc ctttgagggt aacccgacct      60
ttctctttgg ctgcccttaa cattttttcc ttcatttcaa cttggtgaa tctgacaatt      120 atgtgtcttg gagttgctct tctcgaggag tatctttgtg gcattctctg tattttctga    180
atctgaatgt tggcctgcct tgctagattg gggaagttct cctggataat atcctgcaga    240
gtgttttcca acttggttcc attctcccca                                      270

<210> SEQ ID NO 105
<211> LENGTH: 246
<212> TYPE: DNA
<213> ORGANISM: Homo sapiens

<400> SEQUENCE: 105
gatcacgagg tcaggagatt gagaccatcc tggctaacac ggtgaaaccc cgtctctact      60
aaaaatacaa aaaattagcc aggcgtggtg gcaggcgcct gtagtcccag ctactcggga    120
ggctgaggca ggagaatggc atgaacccag gaggcggagc ttgcagtgag ccaagatcgc    180
gccactgcat tccagcctga gcgacagact gagactccgt ctcaaaaaaa agaaaaagaa    240
aaaaaa                                                                246

<210> SEQ ID NO 106
<211> LENGTH: 241
<212> TYPE: DNA
<213> ORGANISM: Homo sapiens

<400> SEQUENCE: 106
tataaaacat gctgctataa aggcacatgc acatgtatgt ttattgcagc actattcaca      60
atagcaaaga cttggaacta acccaaatgt ccatcagtga tactggat taagaaaacg      120 tggcacatat acaccatgga atactatgca gccataaaaa atgatgagtt catgtccttt    180
gtagggacat ggatgaaatt ggaaatcatc attctcagta aactatcgca aggacaaaaa    240
a                                                                     241

<210> SEQ ID NO 107
<211> LENGTH: 233
<212> TYPE: DNA
<213> ORGANISM: Homo sapiens

<400> SEQUENCE: 107
tgtggtctga gagacagttt gttataattt ctgttctttt acatttcctg aggagtgctt      60
```

```
tacttccaac tatgtggtca attttggaat aggtgtggtg tggtgctgag aagaatgtat      120
attctgttga tttggggtgg agagttctgt agatgtctgt taggtccact tggtgcagag      180
ctgagttcaa gtcctggata tccttgttaa gcttctgtct catggatctg tct             233

<210> SEQ ID NO 108
<211> LENGTH: 244
<212> TYPE: DNA
<213> ORGANISM: Homo sapiens

<400> SEQUENCE: 108
aaacatacgt gtgcatgtgt ctttatagta gaatgattta taatcctttg ggtatatacc      60
cagtaatggg attgctgggt caaatggtat ttctggttcc agatccttga ggaatcaccc      120
actgtcttcc acaatggttg aactaattta cactcccacc aacagtgtaa aagcattcct      180
gtttctccac atcctctcca gcatctgttg ttttctgact ttttaatgat catcattcta      240
actg                                                                    244

<210> SEQ ID NO 109
<211> LENGTH: 238
<212> TYPE: DNA
<213> ORGANISM: Homo sapiens

<400> SEQUENCE: 109
attcaacata gtattggaag ttctggccag ggtaattagg caggagaagg aaataaaggg      60
tattcaattg ggaaaagagg aagtcaaatt gttcctgttt gcagatgaca tgattgtata      120
tctagaaaac cccattgtct cagcccaaaa tctccttaag ctgataagca acttcagcaa      180
agtctcagga tacaaaatca atgtacaaaa atcataagca ttcttataca ccaacaac       238

<210> SEQ ID NO 110
<211> LENGTH: 198
<212> TYPE: DNA
<213> ORGANISM: Homo sapiens

<400> SEQUENCE: 110
ggtcaggagt tcgagaccag cctggccaac atggtgaaac cccatctcta ctaaatatac      60
aaaaattacc cgggcatggg gacgggtgcc tgtaatccca gctgttcagg aggctgaggc      120
aggggaatcg cttgaacccg ggaggcggag gttgcagtga acagagatcg tgtcactgca      180
ctccagcctg ggtgatag                                                    198

<210> SEQ ID NO 111
<211> LENGTH: 111
<212> TYPE: DNA
<213> ORGANISM: Homo sapiens

<400> SEQUENCE: 111
gtgtctgtgt agaaagaagt agacatggga gacttttcat tttgttctgt actaagaaaa      60
attcttctgc ctgggatcc tgttgatctg tgaccttacc cccaaccctg t                111

<210> SEQ ID NO 112
<211> LENGTH: 160
<212> TYPE: DNA
<213> ORGANISM: Homo sapiens

<400> SEQUENCE: 112
tctttgaaac caacaagaac aaagacacaa cataccagaa tctctgggac acattcaaag      60
cagtgtgtag agggaaattt atagcactaa atgcccacaa gagaaagcag gaaagatcca      120
```

```
aaattgacac cctaacatca caattaaaag aactagaaaa                           160

<210> SEQ ID NO 113
<211> LENGTH: 288
<212> TYPE: DNA
<213> ORGANISM: Homo sapiens

<400> SEQUENCE: 113
tctctgtttg tctgttattg gtgtataaga atgcttgtga ttttttgcacg ttgattttgt    60 atcctgagac tttgctgaag ttgcctatca gcttaaggag attttgggct gagacaatgg   120
ggttttctag atatacaatc atgtcatctg caaacaggaa caatctgact tcctcttttc   180
ctaattgagt acccttttatt tccttctcct gcctgattgc cctggccaga acttccaaca   240
ctatgttgaa taggagtggt gagagagggc atcgctgtct tctgccag                 288

<210> SEQ ID NO 114
<211> LENGTH: 202
<212> TYPE: DNA
<213> ORGANISM: Homo sapiens

<400> SEQUENCE: 114 tttttttgttc ttgtgatagt ttgctgagaa tgatggtttc cagcttcatc catgtcccta   60
caaaggacat gaactcatca tttttatggc tgcatagtat tccatggtgt atatgtgcca   120
cattttctta atccagtcta tcattgttgg atatttgggt tggttccaag tctttgctat   180
tgtcagtaat gtctcaataa ac                                             202

<210> SEQ ID NO 115
<211> LENGTH: 256
<212> TYPE: DNA
<213> ORGANISM: Homo sapiens

<400> SEQUENCE: 115
atgctggcct cataaaataa gttagggagg attccctctt tttctactga ttggaatagt   60
ttcagaagga atggtatcag ctcctccttg tacctctggt aggatccggc tgtgaatcca   120
tctggtcctg gactttttttt ggttggtaag ctattaatta ttgcctcaat ttcagagtct   180
gttattggtc tattcagaga ttcaacttct tcctgattta gtcttgggag ggtgtatgtg   240
tcgaggaatt tatcca                                                    256

<210> SEQ ID NO 116
<211> LENGTH: 233
<212> TYPE: DNA
<213> ORGANISM: Homo sapiens

<400> SEQUENCE: 116
gagagatcca ctgttagtct gatgggcttc catttgtggg taacccgacc tttctctctg   60
gctgccctta acattatttc ctcatttcaa ctttgctgaa tctgacaatt atgtgtcttg   120
gagttgctct tctcgaggag tatctttgtg gcattctctg tatttcctga atttgattgt   180
tggcctgcct tgctagattg gggaagttct cctggataat atcctgcaga gtg           233

<210> SEQ ID NO 117
<211> LENGTH: 140
<212> TYPE: DNA
<213> ORGANISM: Homo sapiens

<400> SEQUENCE: 117
```

```
gtcttgctct gtcgcccagg ctggagtgca gtggcgcgat ctcggctcac tgcaagctcc    60
gcctcctggg ttcacgccat tctcctgcct cagcctcctg agtagctggg actacaggcg   120
tccaccacca cgcccagcta                                                140

<210> SEQ ID NO 118
<211> LENGTH: 285
<212> TYPE: DNA
<213> ORGANISM: Homo sapiens

<400> SEQUENCE: 118
gtttatattt gggatataaa cccaaaggat tataaatcat gcttctataa agacacatgc    60
acacatatgt ttattgtggc actattcacc atagcaaaga cttggaacca acccaaatgt   120
ccaacaatga tagactggat taagaaaatg tggcacatat acaccatgga atactatgca   180
gccataagaa atgatgagtt catgtccttt gtagggacat ggatgaaatt ggaaatcatc   240
attctcagta aagtattgca aggacaaaaa accaaccccca aacac                  285

<210> SEQ ID NO 119
<211> LENGTH: 292
<212> TYPE: DNA
<213> ORGANISM: Homo sapiens

<400> SEQUENCE: 119
agttatacat tcttctaaat ttttttcaaa gttttcaact tctttgcctt tggtttgaat    60
gtcctctcgt agctcagagt aatttgatcg tctgaagcct tcttctctca gctcgtcaaa   120
gtcattctcc atccagcttt gttctgttgc tggtgaggaa cttcgttcct ttggaggagg   180
agaggcgctc tgcgttttag agtttccagt ttttctgttc tgtttttttct ccatctttgt   240 ggtttatcta cttttggtct ttgatgatga tgatgtacag atgggttttt gg           292

<210> SEQ ID NO 120
<211> LENGTH: 243
<212> TYPE: DNA
<213> ORGANISM: Homo sapiens

<400> SEQUENCE: 120
gctaaaaact ctcaataaat taggtattga tgggatgtat ctcaaaataa taagagctat    60
ttatgacaaa cccacagcca atatcatact gaatgggcaa aaactggaag cattcccttt   120
gagaactggc acaagacagg gatgccactc ctattcaaca ctcaccactc ctattcaaca   180
tagtgttgta agttctggcc agggcaatca ggcaggagaa agaaataaag ggtattcaac   240
tag                                                                 243

<210> SEQ ID NO 121
<211> LENGTH: 259
<212> TYPE: DNA
<213> ORGANISM: Homo sapiens

<400> SEQUENCE: 121
ttgttattcc tgagttctag tttggttaca ctgtggtctg agagacagtt tgttataatt    60
tctgttcttt tacatttgct gaggagagct ttacttccaa ctatgtggtc agttttggaa   120
ctgtccctgt ttgcagatga catgattgta tatctagaaa accccattgt ctcagcccaa   180
aatctcctta agctgataag caacttcagc acagtctcag gatacaaaat caatgtacaa   240
aaatcacaag cattcttat                                                259
```

```
<210> SEQ ID NO 122
<211> LENGTH: 279
<212> TYPE: DNA
<213> ORGANISM: Homo sapiens

<400> SEQUENCE: 122
aattcggaac tggtaccatt ccttctgaaa ctattccaat taatagaaaa agagggaatc      60
ctccctaact cattttaaga ggccagcatc attctgatac caaagccggg cagagacaca     120
accaaaaaac agaattttag accaatatcc ttgatgaaca ttgatgcaaa aatcctcaat     180
aaaatactgg caaactgaat ccagcagcac atcaaaaagc ttatccacca tgatcaagtg     240
ggcttcatcc ctgggacgca aggctggttc aatatacgc                            279

<210> SEQ ID NO 123
<211> LENGTH: 272
<212> TYPE: DNA
<213> ORGANISM: Homo sapiens

<400> SEQUENCE: 123
accgctagca agactaataa agaaaaaaag agagaagaat caaatagacg caataaaaaa      60
tgataaaggg gataccacca ctgatcccac agaaatacaa actaccatca gagaatacta    120
caaacacctc tatgcaaata aactagaaaa tctagaagaa atggataaat ccttgacac     180 gtacatgctc ccaagactaa accaggaaga agttgaatct ctgaatagac caataacagg    240
agctgaaatt ggggcaataa tcaatagctt ac                                   272

<210> SEQ ID NO 124
<211> LENGTH: 241
<212> TYPE: DNA
<213> ORGANISM: Homo sapiens

<400> SEQUENCE: 124
tgacatgggt ctcctgaata cagcacactg atgggtcttg actctttatc caatttgcca     60
gtctgtgtct tttaattggg gcattcagcc catttacatt taaggttaat attgttatgt    120
gtgaatttga tcctgtcatt atgatgttag ctggttattt tgcttgttag ttgatgcagt    180
ttcttcctag catctatggt ctttacagtc tggcatattt tgcagtggct ggtactggtt    240
g                                                                     241

<210> SEQ ID NO 125
<211> LENGTH: 184
<212> TYPE: DNA
<213> ORGANISM: Homo sapiens

<400> SEQUENCE: 125
cctttgtgat gtgtgtgttc aactcacaga gtttaacacc cacacccaa acacacccaa      60 cacaaggag tttctgagaa tcattctgtc tagtttttct acgaagatat ttccttttct    120
actattgacc tcaaagcggc tgaaatctcc acttgcaaat tccacgaaaa gagtgtttca    180
agtc                                                                  184

<210> SEQ ID NO 126
<211> LENGTH: 278
<212> TYPE: DNA
<213> ORGANISM: Homo sapiens

<400> SEQUENCE: 126
cacccactcc agcatataaa cagaaccaaa gacaaaaacc acatgattat ctcaatggat      60
```

```
gcagaaaagg cctttgacaa aattcaacaa cccttcatgc taaaaactct caataagtta    120
ggtattgatg ggacatattt caaaataata agagctatct atgacaaacc cacagccaat    180
atcatactga atgggcaaaa actggaagca tttcctttga aaactggcac aagacaggga    240
tgtcctctct taccactctt attcaacata gtaatgga                            278

<210> SEQ ID NO 127
<211> LENGTH: 274
<212> TYPE: DNA
<213> ORGANISM: Homo sapiens

<400> SEQUENCE: 127
cctccaagct atccaaatat ccactttcag attccacaaa aagagtgctg ctctgtaata    60
agaaaggttc atccctgtta gttgaataca cacatcacaa acaagtttct gagaatgctt    120
ctgtctagtt tttatgggaa gatatttcct ttttcaacat aggcctcaaa gcgctccaaa    180
cgtccacttc caggtagtgc agaaagagtg tctcaaacct ggtatataac agggaacatt    240
ctattctgtg acttgaatga aaacatcaca aagc                                274

<210> SEQ ID NO 128
<211> LENGTH: 289
<212> TYPE: DNA
<213> ORGANISM: Homo sapiens

<400> SEQUENCE: 128 tacccttttct tccagttgat cgcatcggct cctgaggctt ctgcattctt cacgtagttc    60
tcgagccttg gttttcagct ccatcagctc ctttaagcac ttctctgcat tggttattct    120
agttataaat tcttctaaat ttttttcaaa gttttcaact tctttgcctt tggtttgaat    180
gtcctcccgt agctcagagt aatttgatcg tctgaagcct tcttctctca gctcgtcaaa    240
atcattctcc atccagcttt gttccgttgc tggtgaggaa ctgcgttcc                289

<210> SEQ ID NO 129
<211> LENGTH: 227
<212> TYPE: DNA
<213> ORGANISM: Homo sapiens

<400> SEQUENCE: 129
agttggcttc atccctggga tgcatggctg gttcaacata cacaaatcaa taaacgtaat    60
ccatcatata aacagaacca agacaaaaa ccacatgatt atctcaatag atgcagaaaa    120
ggcctttgac aaaattcaac aacccttcat gctaaaaact ctcaataaat taggtactga    180
tgggacgtgt ctcaaaataa taagagctat ctatgacaaa cccacac                227

<210> SEQ ID NO 130
<211> LENGTH: 283
<212> TYPE: DNA
<213> ORGANISM: Homo sapiens

<400> SEQUENCE: 130
gagtcagaga ggattccctc ttttctgtt gattggaata gtttcagaag gaatggtacc    60
agctcctcct tgtacctctg gtagaattcg gctgtgaatc catctggtcc tggactcttt    120
ttggttggta agctattgat tattgccaca atttcagatc ctgttattgg tctattcaga    180
gattcaactt cttcctggtt tagtcttgag agagtgtaca tgtctagaaa tttatccatt    240
tcttctagat tttctagttt atttgcatag aggtatttgt agt                    283
```

<210> SEQ ID NO 131
<211> LENGTH: 277
<212> TYPE: DNA
<213> ORGANISM: Homo sapiens

<400> SEQUENCE: 131

```
catttattga tttgcatata ttgaaccagc ctttcatccc agggatgaag cccacttgat        60
catggtggat aagcttttg atgtgctgct ggattcggtt tgccagtatt ttattgagga       120
tttttgcatc aatgttcatc agggatattg ttctaaaatt cttttttgttg tgtctctgcc     180
aggctttggt atcaggatga tgctggcctc ataaaatcag ttagggagga ttccctcttt     240
ttcagttgat tggaatagtt tcagaaggaa tggtacc                              277
```

<210> SEQ ID NO 132
<211> LENGTH: 246
<212> TYPE: DNA
<213> ORGANISM: Homo sapiens

<400> SEQUENCE: 132

```
tttggtttgt tttgttacag catttggaa accttcaaat ctatccaaat atccacctgc        60
agatcctaca aaagagtgt ttccaaaatg ctgtatcaaa acaaaggttc aactctgtta      120
gttgagaaca cacatcgcaa ataagtttct gagaatgctt ctgtctagtt tttatttgaa     180
gatatttccc ttttcaccac aggcctgaaa gcgcttgaaa cgtccgcttg cagatactac     240
aaaagg                                                                246
```

<210> SEQ ID NO 133
<211> LENGTH: 209
<212> TYPE: DNA
<213> ORGANISM: Homo sapiens

<400> SEQUENCE: 133

```
gtttggttg tttgtgcatt gattttgtat gctgagactt tgctgaagtt gcttatcagc        60
ttaaggagat tttggcatga agggttgttg aattttgtca aaggccttt ctgcatctat      120
tgagataatc atgtggtttt tgtctttggt tctgtttata tgctggatta catttattaa     180
tttgcatata ttgaaccagc cttgcatcc                                        209
```

<210> SEQ ID NO 134
<211> LENGTH: 285
<212> TYPE: DNA
<213> ORGANISM: Homo sapiens

<400> SEQUENCE: 134

```
aactatctct cagaccacag tgcaatcaaa ctagaactca ggattaagaa actcgctcaa        60
aaacgctcaa ctacatggaa actgaacaac ctgctcctga atgactactg ggtaaataat      120
gaaatgaagg cagaaataaa gattttctt gaaaccaacg agaacaaaga cacaacatac       180
cagaatctct gggacacatt caaagcagta tgtagagaga aatttataga actaaatgcc       240
cacaagagaa agcaggaaag atctaaaatt gacaccataa tatca                      285
```

<210> SEQ ID NO 135
<211> LENGTH: 234
<212> TYPE: DNA
<213> ORGANISM: Homo sapiens

<400> SEQUENCE: 135

```
ggttttttgg tttgaaagtc ctcctgtagc tcgaagtaat ttgatcttct gaagccttct        60
```

```
tctctcagct tgtcagtcat tctccgtcct gctttgttcc gttgctggtg aggaactgcg    120
ttcctttgga ggaggagagg tgctctgctt tttagagttt ccagttttc tgttctgttt     180 tttccccatc tttgtggttt tatgtacttt tggtctttga tgatggtgat gtac          234
```

```
<210> SEQ ID NO 136
<211> LENGTH: 270
<212> TYPE: DNA
<213> ORGANISM: Homo sapiens

<400> SEQUENCE: 136
cacacccaac acatcaaaaa gcttatccac catgatcaag tgggcttcat ccctgggatg    60
caaggctggt tcaatatacg caaatctata agtgtaatcc agcatacaaa cagaaccaaa    120
gacaaaaacc acatgattat ctcaatagat gcagaaaagg cctttgacaa aattcaacaa    180
cccttcatgc taaaaactct cagtaaatta ggtattgatg ggatgtatct caaaataata    240
agagctattt atgacaaacc cacaccaaac                                     270
```

```
<210> SEQ ID NO 137
<211> LENGTH: 264
<212> TYPE: DNA
<213> ORGANISM: Homo sapiens

<400> SEQUENCE: 137
cctcataagt tggattccta ggtattttgt tcttttttgaa gcaattgtga atgggagttt   60
actcatgatt tggctctctg tttgtctgtt attggtgtat aggaatgttt gttattttttg  120 cacattgatt ttgtatcctg agactttgct gaagttgctt atcagcttaa gaagattttg    180
ggctgagacg atggggtttt ctaaatatac aatcatgtca tctgcaaaca gggacaattt    240
gagttcctct tttcctaatt gaat                                            264
```

```
<210> SEQ ID NO 138
<211> LENGTH: 195
<212> TYPE: DNA
<213> ORGANISM: Homo sapiens

<400> SEQUENCE: 138
cataaaatga gttagggagg attccctctt tttctattga ttggaatagt ttcagaagga    60
atggtaccag ttccttctga aactattcca atcaatagaa aaagagggaa tcctccctaa    120
ctcattttat gaggccagca tcattctgat accaaagccg ggcagagaca caaccaaaaa    180
agagaatttt agacc                                                      195
```

```
<210> SEQ ID NO 139
<211> LENGTH: 205
<212> TYPE: DNA
<213> ORGANISM: Homo sapiens

<400> SEQUENCE: 139
ttggtttggt ttgccagtat tttatgaggc cagcatcatc ctgataccaa agcctggtag    60
agacacacca atatccctga tgaacatcaa tgcaaaaatc ctcaataaaa tactggcaaa    120
ccgaatccag cagcacatca aaaagcttat ccaccatgat caagtgggct tcatccctgg    180
gatgcaaggc tggttcaata tacgc                                           205
```

```
<210> SEQ ID NO 140
<211> LENGTH: 258
<212> TYPE: DNA
<213> ORGANISM: Homo sapiens
```

<400> SEQUENCE: 140

```
ctgtttacat gctggattac gtttattgat ttgcgtatgt tgaaccaaag acaaaaacca      60
catgattatc tcaatagatg cagaaaaggc ctttgacaaa tttcaacagc ccttcatgct     120
aaaaactctc aataaattag gtattgatgg gacgtatctc aaaataataa aagctatcta     180
tgacaaaccc acagccaata tcatactgaa tgggcaaaaa ctggaagcat tcccttttgaa    240
aactggcaca agaaaggg                                                   258
```

<210> SEQ ID NO 141
<211> LENGTH: 289
<212> TYPE: DNA
<213> ORGANISM: Homo sapiens

<400> SEQUENCE: 141

```
gctcggagta gtttgatcgt ctgaagcctt cctctctcag ctcgtcaaaa tcattcacca      60
tccagctttg ttccgttgct ggtgaggaac tgcgctcctt tggaggagga gaggcgctct     120
gcttttttaga gtttccagtt tttctgttct gttttttccc catctttgtg gttttatcta    180
cttttggtct ttgatgatgg tgatgtacag atgggttttt ggtgtggatg tccttttctgt    240
ttgttagttt tccttctaac agacaggacc ctcagctgca ggtctgtac                 289
```

<210> SEQ ID NO 142
<211> LENGTH: 202
<212> TYPE: DNA
<213> ORGANISM: Homo sapiens

<400> SEQUENCE: 142

```
tttttgttgt gtctctgcct ggctttggta tcagaatgat gctggcctca taaaatgagt      60
tagggaggac tccctctttt tctgttgatt ggaatagttt cagaaggaat ggtaccagct     120
cctccttgta cctctggtag aattcggctg tgaatccatc tggtcctgga ctctttttat    180
gaggccagca tcattctgat ac                                              202
```

<210> SEQ ID NO 143
<211> LENGTH: 104
<212> TYPE: DNA
<213> ORGANISM: Homo sapiens

<400> SEQUENCE: 143

```
ggtctggagt ggacctccaa aaagggtctg gagtggacct ccagcaaact ccaacagacc      60
tgcagctgag ggtcctgact gttagaagga aaactaacaa acag                      104
```

<210> SEQ ID NO 144
<211> LENGTH: 200
<212> TYPE: DNA
<213> ORGANISM: Homo sapiens

<400> SEQUENCE: 144

```
tacttagata accacagcct aagaattcat tagcttttaa aacaatcttg cttcacactt      60
gacttacatt gccttcacaa tcaacaaaag tcttttggtt taaatgattt ttcaagtcct     120
tttcaatgct gtgatattat tgttatctcc tccacgttct ttgtttaaac tattggtctg    180
ccgggcgcgg tggctcacac                                                 200
```

<210> SEQ ID NO 145
<211> LENGTH: 200
<212> TYPE: DNA

<213> ORGANISM: Homo sapiens

<400> SEQUENCE: 145

| ggatggaatg cccaacaaat acttagattt atgggtttgg aacccaggag atagatctca | 60 |
| gtaaatgata aagagttgag agtcattggc ctgtagattc attcatctac tcattcagta | 120 |
| aatattcact tactaacgtg ctttgtctca ggcattaagt atacagtggt aaattaaaac | 180 |
| attattttag ttttcacaaa | 200 |

<210> SEQ ID NO 146
<211> LENGTH: 150
<212> TYPE: DNA
<213> ORGANISM: Homo sapiens

<400> SEQUENCE: 146

| gcagcctcta ctattcctta ctttattata cccacccatt ttcctcactt ctatcatttg | 60 |
| cctggtccat gtaggccatc tgagtttaag atctctggca tacagtttat ctgggaagat | 120 |
| aagctacaca taccacacac tccacatatc | 150 |

<210> SEQ ID NO 147
<211> LENGTH: 200
<212> TYPE: DNA
<213> ORGANISM: Homo sapiens

<400> SEQUENCE: 147

| tctgcgcttc aaatgccact ttgtttactc gctgtggtca tccttttctg taaatactgt | 60 |
| gtcagcatta acagcctcct ctatggctac ctagcaggtc acttagtaaa ctatctttta | 120 |
| gtaacaacta catagaatga atactcagga gccttaattc aatttacctg cataaagaaa | 180 |
| ctattcacta ttacaacaca | 200 |

<210> SEQ ID NO 148
<211> LENGTH: 200
<212> TYPE: DNA
<213> ORGANISM: Homo sapiens

<400> SEQUENCE: 148

| cagtcctaaa gagggagaca ttattacttt ccccattcgt agaatgagta aactgagttt | 60 |
| taagtaggtt aaatggtttg tacaggatta cagaattaga gaatgaaaga accacatggc | 120 |
| aaacccatgt agtttgtgcc aaatttatac tcttctgtgt catagcggtc cttgattgtg | 180 |
| aggttcattc aaagccagca | 200 |

<210> SEQ ID NO 149
<211> LENGTH: 230
<212> TYPE: DNA
<213> ORGANISM: Homo sapiens

<400> SEQUENCE: 149

| ctaactctct ttgtaggtca ctaaggacag cttatccacc atgatcaagt gggcttcatc | 60 |
| actgggatgc aaggctggtt caacatacaa aaatcaataa atgtaatcca gcatataaac | 120 |
| agaaccaaag acaaaaacca catgattacc tcaatagatg cagaaaaggc ctttgacaaa | 180 |
| attcaacaac ccttcatgct aaaaactctc aataaattag gtattgatgg | 230 |

<210> SEQ ID NO 150
<211> LENGTH: 266
<212> TYPE: DNA
<213> ORGANISM: Homo sapiens

<400> SEQUENCE: 150

```
gatattggct gtgggtttgt catagatagc tcttattatt ttgagatatg tcccatcaat      60
acctaattta ttgagagttt ttagcatgaa gggttgttga attttgtcaa aggcttttc     120
tgcatctatt gagataatca tgtggttttt gtctttggct ctgtttatat gctggattac    180
atttattgac ttgtgtatat tgaaccagcc ttgcatccca gggatgcaag gctggttcaa    240
tatacacaag tcaataaatg taatcc                                         266
```

<210> SEQ ID NO 151
<211> LENGTH: 172
<212> TYPE: DNA
<213> ORGANISM: Homo sapiens

<400> SEQUENCE: 151

```
gtttggttgt tgttgaacc agccttgcag cacatcaaaa agcttatcca ccatgatcaa      60
gtgggcttca tccctgagat gcaaggctgg ttcaatatac gcaaatcaat aaatgtaatc    120
cagcatataa acagagccaa agacaaaaac cacatgatta tctcaatcga tg           172
```

<210> SEQ ID NO 152
<211> LENGTH: 234
<212> TYPE: DNA
<213> ORGANISM: Homo sapiens

<400> SEQUENCE: 152

```
cctcaacaca taccctctcc caagactaaa ccaggaagaa gttgaatctc tgaatagacc      60
aataacagga tctgaaattg tggcaataat caatagctta ccaaccaaaa agagtccagg    120
accagatgga ttcacagccg aattctacca gaggtacaag gaggaactgg taccatttct    180
tctgaaacta ttccaatcaa atagacgcaa tcaaaccacc gatcccacaa aaac          234
```

<210> SEQ ID NO 153
<211> LENGTH: 214
<212> TYPE: DNA
<213> ORGANISM: Homo sapiens

<400> SEQUENCE: 153

```
atattgttat gtgtgaattt gatcctgtca ttatgatgtt agctggtgat tctcccaaga      60
ctaaaccagg aagaagttga atctctgaat agaccaataa caggctctga aattgtggca    120
ataatcaata gtttaccaac caaaagagt ccaggaccag atggattcac agccgaattc     180
taccagaggt acaaggagga actggtacca ttcc                                214
```

<210> SEQ ID NO 154
<211> LENGTH: 228
<212> TYPE: DNA
<213> ORGANISM: Homo sapiens

<400> SEQUENCE: 154

```
gcatataaac agaaccaaag acaaaaacca catgattatc tcaatagagg cagaaaaggc      60
ctttgacaaa attcaacaac ccttcatgct aaaaactctc aataaattag gtattgatgg    120
gacgtatctc aaaataataa gagctatgca tgacacaccc acagccaata tcatactgaa    180
tgggcaaaaa ctggaagcat tccctttgaa aactggcaca acccaacc                 228
```

<210> SEQ ID NO 155
<211> LENGTH: 283
<212> TYPE: DNA

<213> ORGANISM: Homo sapiens

<400> SEQUENCE: 155

| gtatgatgct ggcctcataa aatgagtcag ggagaatttc ctcttttct attgattgga | 60 |
| atagtttcag agggaatggt accaattcct ctttgtacct ctggtagaat tcagctgtga | 120 |
| atccatctgg tcctggactc ttttggttg gtaagctatt gattattgcc acaatttcag | 180 |
| ctcctgttat tggtctattc agagattcaa cttcttcctg gtttagtctt gggagagtgt | 240 |
| atgtgtcgag gaatttatcc atttcttcta gattttctag ttt | 283 |

<210> SEQ ID NO 156
<211> LENGTH: 255
<212> TYPE: DNA
<213> ORGANISM: Homo sapiens

<400> SEQUENCE: 156

| ctatttattg gaatagtttc agaaggaatg gtaccagttc ctccttgtac ctctggtaga | 60 |
| attcggctgt gaatccatct ggtcctggac tcttttggt tggtaaacta ttgattattg | 120 |
| ccacaatttc agctcctgtt attggtctat tcagagattc aactaaactc agattcctgg | 180 |
| tttagtcttg ggagagtgta tgtgtcgagg aatttatcca tttcttctag attttctagt | 240 |
| ttatttgcgt agagg | 255 |

<210> SEQ ID NO 157
<211> LENGTH: 281
<212> TYPE: DNA
<213> ORGANISM: Homo sapiens

<400> SEQUENCE: 157

| atacacaaat caataaatgt aatccagcat ataaacagag ccaaagacaa aaccacatg | 60 |
| attatctcaa tagatgcaga aaggcctttg acaaaattca caacccttc atgctaaaaa | 120 |
| ctctcaataa attaggtatt gatgggacgt atttcaaaat aataagagct atctatgaca | 180 |
| aacccacagc caatatcata ctgaatgggc aaaaactgga agcattccct ttgaaaactg | 240 |
| gcacaagaca gggatgccct ctctcaacac atattcaaaa t | 281 |

<210> SEQ ID NO 158
<211> LENGTH: 221
<212> TYPE: DNA
<213> ORGANISM: Homo sapiens

<400> SEQUENCE: 158

| gatacatccc atcaatacct aatttattga gagttttag catgaagggc tgttgaattt | 60 |
| tgtcaaaggc cttttctgca tctattgaga taatcatgtg gttttgtct ttggttctgt | 120 |
| ttatatgctg gattacgttt attgatttgc gtatgttgaa ccaggcttgc atcccaggga | 180 |
| tgaagcctgg ttcaacatac gcaaatcaat aaacgtaatc c | 221 |

<210> SEQ ID NO 159
<211> LENGTH: 250
<212> TYPE: DNA
<213> ORGANISM: Homo sapiens

<400> SEQUENCE: 159

| gccttacaag agctcctgaa ggaagcacta acatggaaa ggaacaaccg gtaccagccg | 60 |
| ctgtaaaatc atgccaaaat gtaaagacca tcgagactag gaagaaactg catcaactaa | 120 |
| cgagcaaaat aaccagctaa catcataatg acaggatcaa attcacacat aacaatttaa | 180 |

```
atgtaaatgg actaaatgct ccaattaaaa gacacagact ggcaaattgg ataaagagtc    240
aagacctatc                                                          250

<210> SEQ ID NO 160
<211> LENGTH: 272
<212> TYPE: DNA
<213> ORGANISM: Homo sapiens

<400> SEQUENCE: 160 gtccctttt  tcaaagggaa tgcttccagt ttttgcccat tcagtatgat attggctgtg    60
ggtttgtcat agatagttct tattattttg aaatacgtcc catcaatacc taatttattg   120
agagttttta gcatgaaggg ttgttgaatt ttgtcaaagg cttttctgc atctattgag    180 ataatcatgt ggttttgtc tttggctctg tttatatgct ggattacatt tattgatttg    240
catatattga accagagaca aaaaccacaa cc                                 272

<210> SEQ ID NO 161
<211> LENGTH: 269
<212> TYPE: DNA
<213> ORGANISM: Homo sapiens

<400> SEQUENCE: 161
actacaaaca cctctacgca aataaactag aaaatctaga agaaatggat acatacactc    60
tcccaagact aaaccaggaa gaagttgaat ctctgaatag accaataaca ggctctgaaa   120
ttgaggcaat aattaatagc ttaccaacca aaaaagtcc aggaccagat ggattcacag     180
ccgaattcta ccagaggcac aaggaggagc tggtaccatt ccttctgaaa ctattccaat   240
caatagaaaa agagggaatc ctccttaac                                    269

<210> SEQ ID NO 162
<211> LENGTH: 229
<212> TYPE: DNA
<213> ORGANISM: Homo sapiens

<400> SEQUENCE: 162
gggtttgttg gtaacctgac cttttttaaag gcagccagag aaaaaggtca ggttacccac    60
aaaaggaagc ccatcagact aactgctgat ctctcggcag aaactctaca agccagaaga   120
gagtaggggc caatattcaa cattcttaaa gaaaagaatt ttcaacccag aatttcatat   180
ccagccaaac taagcttcat aagtgaagga gaaataaaat actttacag               229

<210> SEQ ID NO 163
<211> LENGTH: 275
<212> TYPE: DNA
<213> ORGANISM: Homo sapiens

<400> SEQUENCE: 163
ggtcaaaatg aaaaaaaaaa tgttaatggc agccagagag aaaggtcggg ttaccctcaa     60
agggaagccc atcagactaa cagtggatct cttggcagaa accctacaag ccagaagaga   120
gtgggggcca atattcaaca ttcttaaaga caagaatttt caacccagaa tttcatatcc    180
agccaaacta agcttcataa gtgaaggaga aataaaatcc tttacagaca agcaaatgct   240
gagagatttt gtcaccacca ggcctgccct aaaag                             275

<210> SEQ ID NO 164
<211> LENGTH: 292
<212> TYPE: DNA
```

<213> ORGANISM: Homo sapiens

<400> SEQUENCE: 164

| | |
|---|---|
| gagcaactct tctcctccaa aggaacgcag ctcctcacca gcaacagaac aaagctggac | 60 |
| ggagaatgac tttgacgagc tgagagaaga aggcttcaga cgatcgaatt actctgagct | 120 |
| acgggaggac attcaaacca aaggcagaga agttgaaaac tttgaaaaaa atttagaaga | 180 |
| atgtataact agaataacca atacagaaa gtgcttaaag gagctgatgg agctgaaaac | 240 |
| caaggctcaa gaactacgtg aagaatgcag aagcctcagg agccgatgcg at | 292 |

<210> SEQ ID NO 165
<211> LENGTH: 225
<212> TYPE: DNA
<213> ORGANISM: Homo sapiens

<400> SEQUENCE: 165

| | |
|---|---|
| gctttgtctt gtgggcattt agtgctataa atttccctct acacactgct ttgaatgcgt | 60 |
| cccagagatt ctggtatgtt gtgtctctgt tgtaattgtc cctgtttgca gacgacatga | 120 |
| ttgtttatct agaaaacccc atcgtctcag cccaaaatct ccttaagctg ataagcaact | 180 |
| tcagcaaagt ctcaggatac aaaatcaatg tacaaaaatc acaag | 225 |

<210> SEQ ID NO 166
<211> LENGTH: 239
<212> TYPE: DNA
<213> ORGANISM: Homo sapiens

<400> SEQUENCE: 166

| | |
|---|---|
| cagcttatct ctcagcagaa acactacaag ccagaagaga gtaggggcca atattcaaca | 60 |
| ttcttaatga aaagaatttt caacccagaa tttcatatcc agccaaacta agcttcataa | 120 |
| gtgaaggaga aataaaatcc tttacagaca agcaaatgct gagagatttt gtcaccacca | 180 |
| ggcctgccct aaaagagctc ctgaaggaag cactaaacat agaaaggaac aactggtac | 239 |

<210> SEQ ID NO 167
<211> LENGTH: 255
<212> TYPE: DNA
<213> ORGANISM: Homo sapiens

<400> SEQUENCE: 167

| | |
|---|---|
| acttccccaa tctagcaagg caggccaaca ttcagattca ggaagtacag agaacgccac | 60 |
| aaagatactc ctcgagaaga gcaactccaa gacacataat tgtcagattc accaaagttg | 120 |
| aaatgaagga aaaaatgtta agggcagcca gagacaaagg tcggattacc cacaaaaaga | 180 |
| agcccatcag actaacagcg gatctcttgg cagaaactct acaagccaga agagagtggg | 240 |
| gaccaatact caaca | 255 |

<210> SEQ ID NO 168
<211> LENGTH: 244
<212> TYPE: DNA
<213> ORGANISM: Homo sapiens

<400> SEQUENCE: 168

| | |
|---|---|
| atacatccca tcaataccta atttattgag agttttttagc atgaagggtt gttgaatttt | 60 |
| gtcaaaggcc ttttctgcat ctattgagat aatcatgtgg ttttttgtctt tggttctgtt | 120 |
| tatatgctgg attacatttta ttgatttgtg aatattgaac cagccttgca tcccagggat | 180 |
| gaagcccacc tgatcatggt ggacaagctt tttgatgtgc tgctggattc agtcccacac | 240 |

```
aaac                                                                  244

<210> SEQ ID NO 169
<211> LENGTH: 255
<212> TYPE: DNA
<213> ORGANISM: Homo sapiens

<400> SEQUENCE: 169
atgtaatcca gcatataaac agaaccaaag acaaaaacca catgattatc tcaatagatg     60
cagaaaaggc ctttgacaaa attcaacaac ccttcatgct aaaaactctc aataaattag    120
gtattgatgg gacgtatctc aaaatactaa gagctaccta tgacaaaccc acagccaata    180
tcacactgaa tgggcaaaaa ctggtagcat tctctttgaa aactggcatg tgacagggat    240
gccctctctc accac                                                     255

<210> SEQ ID NO 170
<211> LENGTH: 292
<212> TYPE: DNA
<213> ORGANISM: Homo sapiens

<400> SEQUENCE: 170
ttctcacaga gggggatttg gcagggtcat aggacaatag tggagggaag gtcagcagat     60
aaacaagtga acaaaggtct ctggtttttcc taggcagagg accctgcggc cttccgcagt   120
gtttgtgtcc ctggatactt gagattaggg agtggtgatg actcttaacg agcatgctgc    180
cttcaagcat ctgtttaaca agcacatct tgcaccgccc ttaatccatt taaccctgag     240
tggacacagc acatgtttca gagagcatag ggctgggggc aaggtcatag at            292

<210> SEQ ID NO 171
<211> LENGTH: 253
<212> TYPE: DNA
<213> ORGANISM: Homo sapiens

<400> SEQUENCE: 171
tgatcgttct ggccagaact tccaacacta tgtggaatag gagtggtgag agagggcatc     60
cctgtcttgt gccagttttc aaagggaatg cttccagttt ttgcccattc agtatgatat    120
tggctgtggg tttgtcatag atagctctta ttattttgag atacgtccca tcaataccta    180
atttattgag agttttttagc atgaaatgtt gttgaatttt gtcaaaggcc ttttctgcgt   240
ctattgagag tca                                                       253

<210> SEQ ID NO 172
<211> LENGTH: 208
<212> TYPE: DNA
<213> ORGANISM: Homo sapiens

<400> SEQUENCE: 172 ccctctttt ctattgattg gaatagtttc agaaggaatg gtaccagttc ctccttgtac      60
ctctggtaga attcggctgt gaatccatct ggtcctggac tcttttttggt tggtaagcta   120 ttattgccac aatttcagat cctgttattg gtcgacatga ttgtatatct agaaaacccc    180
attgtctcag cccaaagtct ccttaagc                                       208

<210> SEQ ID NO 173
<211> LENGTH: 247
<212> TYPE: DNA
<213> ORGANISM: Homo sapiens
```

<400> SEQUENCE: 173

```
ggttttgttt ttctagttcc tttaattgtg atgttagggt gtcaattttg gatctttcct      60
gcttaaccag gaagaagttg aatctctgaa tagaccaata acaggctctg aaattgtggc     120
aataatcaat agcttaccaa ccaaaaagag tccaggacca gatggattca cagccgaatt     180
ctaccagagg tacaaggagg aactggtacc attccttctg aaactattcc aatcaataga    240
taaagag                                                              247
```

<210> SEQ ID NO 174
<211> LENGTH: 200
<212> TYPE: DNA
<213> ORGANISM: Homo sapiens

<400> SEQUENCE: 174

```
ctttacacag agcagatttg aaacactctt tttgtggaat ttgcaagtgg agatttcaag      60
cgatttgatg ccaacagtag aaaaggaaat atcttcaaat aaaaactaga cagaatcatt     120
ctcagaaact actttgtgat gtgtgccttc aactcacaga gtttaacctt tcttttctta    180
caaacagtgt gtttctaaac                                                200
```

<210> SEQ ID NO 175
<211> LENGTH: 201
<212> TYPE: DNA
<213> ORGANISM: Homo sapiens

<400> SEQUENCE: 175

```
ggtctccggt tttcctaggc agaggaccct gcggccttcc ggccttccgc agtgtttgtg      60
tccctgggta cttgagatta gggagtggtg atgactctta acgagcatgc tgccttcaag    120
catctgttta acaaagcaca tcttgcaccg cccttaatcc atttaaccct gagtggacac    180
agcacatgat tcagagagca c                                              201
```

<210> SEQ ID NO 176
<211> LENGTH: 268
<212> TYPE: DNA
<213> ORGANISM: Homo sapiens

<400> SEQUENCE: 176

```
ctgtaggttg cctgttcact ctgatggtaa cttcttttgc tgtgcagaag ctctttagtt      60
taattagatc ccatttgtca attttggctt ttgttgccat tgcttttggt gttttagtca    120
tgaagccctt gcccatgcct atgtcctgaa tggtattgcc taggttttct tctaggtttt    180
aggtttaaca tttaagtctt taatccatct tgaattaatt tttgtataag gtgtaaggaa    240
gggatccagt ttcagctttc tacatatg                                       268
```

<210> SEQ ID NO 177
<211> LENGTH: 188
<212> TYPE: DNA
<213> ORGANISM: Homo sapiens

<400> SEQUENCE: 177

```
ataaagggat ggaggaagat ctaccaagca aatggaaaac aaaaaaaggc aggggttgca      60
atcctagtct ctgataaaac agactttaaa ccaacaaaaa ccaaacacac ccaacacagg    120
agcaccaaga ttcataaagc aagtcctgag tgacctataa agagacttag actcccacac    180
aataataa                                                             188
```

<210> SEQ ID NO 178
<211> LENGTH: 251
<212> TYPE: DNA
<213> ORGANISM: Homo sapiens

<400> SEQUENCE: 178

| | | | | |
|---|---|---|---|---|
| gccatatgta gaaagctgaa actggatccc ttccttacac cttatacaaa aatcaattca | | | | 60 |
| agatggatta aagacttaaa cgttagacct aaaatcataa aaaccctaga agaaaaccta | | | | 120 |
| ggctaattta ccattcagga cataggcatg ggcaaggact tcatgtccaa aacaccaaaa | | | | 180 |
| gcaatggcaa caaaagacaa aattgacaaa tgggatctaa ttaaactcaa gagcttctgc | | | | 240 |
| acaaaaaaac c | | | | 251 |

<210> SEQ ID NO 179
<211> LENGTH: 189
<212> TYPE: DNA
<213> ORGANISM: Homo sapiens

<400> SEQUENCE: 179

| | | | | |
|---|---|---|---|---|
| tttggtttgt gtgtgatttt tgcacattga ttttgtatcc tgagactttg ctgaagttgc | | | | 60 |
| ctatcagctt aaagagattt tgggccgaga cgatggggtt tcctagatat acaatcatgt | | | | 120 |
| catctgcaaa cagggacaat ttgacttcct cttttcctaa ttgaataccc tttatttcct | | | | 180 |
| tctcctgcc | | | | 189 |

<210> SEQ ID NO 180
<211> LENGTH: 200
<212> TYPE: DNA
<213> ORGANISM: Homo sapiens

<400> SEQUENCE: 180

| | | | | |
|---|---|---|---|---|
| tccatgtccc tacaaaggac atgaactcat cattttttat ggctgcatag tattccatgg | | | | 60 |
| tgtatatgtg ccacattttc ttaatccagt ctatcattgt tggacatttg ggttggttcc | | | | 120 |
| aagtctttgc tattgtgaat agtgccgcaa taaacatatg tgtgcatgtg tctttatagc | | | | 180 |
| agcatgattt atagtccttt | | | | 200 |

<210> SEQ ID NO 181
<211> LENGTH: 200
<212> TYPE: DNA
<213> ORGANISM: Homo sapiens

<400> SEQUENCE: 181

| | | | | |
|---|---|---|---|---|
| gcatcaactg aacgcaaatc agccacttta attaagctaa gcccttacta gaccaatggg | | | | 60 |
| acttaaaccc acaaacactt agttaacagc taagcaccct aatcaactgg cttcaatcta | | | | 120 |
| cttctcccgc cgccgggaaa aaaggcggga gaagccccgg caggtttgaa gctgcttctt | | | | 180 |
| cgaatttgca attcaatatg | | | | 200 |

<210> SEQ ID NO 182
<211> LENGTH: 151
<212> TYPE: DNA
<213> ORGANISM: Homo sapiens

<400> SEQUENCE: 182

| | | | | |
|---|---|---|---|---|
| gtgtgtgtgt gtgtgtgtgt gtgtgtgtat ctatgtatgt acgtatgtat gtatgtatgt | | | | 60 |
| gagtgagatg ggtttcgggg ttctatcatg ttgcccacgc tggtctcgaa ctcctgtcct | | | | 120 |
| caagcaatcc gcctgcctgc ctcggccgcc c | | | | 151 |

```
<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
aaacgtccgc ttgcagatac                                              20

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
agtatgctgc tgtgtacgtt t                                            21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tttgaggctt tcgttggaaa c                                            21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tcagctaaca gaggtggatc t                                            21

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
cttgtggcct tcgttggaaa                                              20

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gatagctgtg aagatttcgt tgg                                          23
```

```
<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
tcagctaaca gaggtggatc t                                              21

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gtggagaaca cacatcacaa tc                                             22

<210> SEQ ID NO 191
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ccctacaagc tagaaagaag ca                                             22

<210> SEQ ID NO 192
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
atgacgtatg cactcaccta ac                                             22

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
ttgtatctgg atgtggacat ttg                                            23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gacagaatca ttcccacaaa ctg                                            23

<210> SEQ ID NO 195
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gaattctcag tagcttcttt gtgt                                           24

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
attcccgttt ccaacgaagg                                                20

<210> SEQ ID NO 197
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
cctttcttat gatacagcag tttgg                                          25

<210> SEQ ID NO 198
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
tctgtctagc atagtatgaa gaaatcc                                        27

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
gtaaagtctg caagtggatg tt                                             22

<210> SEQ ID NO 200
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ctccaccata gccctcaaa                                                 19

<210> SEQ ID NO 201
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
tgagaatgct tctgtctaga gtt                                           23

<210> SEQ ID NO 202
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ggaatgttca actctgtgac tt                                            22

<210> SEQ ID NO 203
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ccctgtcttg tgccagttt                                                19

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
aaagagacaa agaaggccat tac                                           23

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
aaagacacag actggcaaat                                               20

<210> SEQ ID NO 206
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
cagtagagga tataactgcc cataaa                                        26

<210> SEQ ID NO 207
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 207
tgtgtaaagg atcgttcaac tct                                             23

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tctcttgcca ctgccaatta                                                 20

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
gaataatgcc gcaataaaca tacg                                            24

<210> SEQ ID NO 210
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
tctgcaagtg gatattcaga cc                                              22

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
cccattatta acgtgtggga gt                                              22

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tggaaacact ctgtctgtaa agt                                             23

<210> SEQ ID NO 213
<211> LENGTH: 18
<212> TYPE: DNA
<213> ORGANISM: Artificial Sequence
```

<220> FEATURE:
<223> OTHER INFORMATION: Description of Artificial Sequence: Synthetic primer

<400> SEQUENCE: 213
tctgcgatgt gtgcgttc                                    18

<210> SEQ ID NO 214
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 214
gtctctttgt aggtcactca gg                               22

<210> SEQ ID NO 215
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 215
ccattattat tgtttgggcg tctaag                           26

<210> SEQ ID NO 216
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 216
tggtgtgtgc gttcaact                                    18

<210> SEQ ID NO 217
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 217
tttatgaatc tgggtgctcc tg                               22

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 218
tttgtctagc tttgaggatt tcg                              23

<210> SEQ ID NO 219
<211> LENGTH: 24
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 219
gggaattctt ctgtctagcc ttat                                            24

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
gttcaaccat tgtggaagac ag                                              22

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
gacttcaaag cggctgaaat                                                 20

<210> SEQ ID NO 222
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
cccattatta ttgtgtggga gtcta                                           25

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gatgattcca ttcgggtcca                                                 20

<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
gagttgaata cacacaacac aagg                                            24

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 225
cgtttctgag aatgcttctg tc                                             22

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
tcgaatggac tcgaatggaa taa                                            23

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
acattccgtt tcagagagca g                                              21

<210> SEQ ID NO 228
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
caacaactct tcatgctata aactctc                                        27

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
tccatccgat gatgattcca t                                              21

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
atgattctgt ctggtttctt cct                                            23

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 231
tcaacaccac cttcttcgac                                                    20

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
gtggatattc ggacctcttt ga                                                 22

<210> SEQ ID NO 233
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
atttggatac ataggtatgg tctgag                                             26

<210> SEQ ID NO 234
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
acagaacagg ctcctcta                                                      18

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
ccaacggaac aagttaccct a                                                  21

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
gttacaatcg gcatcaacca ac                                                 22

<210> SEQ ID NO 237
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 237
gtagatgtgg tttgactatt tctgtatg                                28

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
attgccacaa ctaacctcct c                                       21

<210> SEQ ID NO 239
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
agccaggcaa ccttcta                                            17

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
gctgtgaaga tttcgttgga aac                                     23

<210> SEQ ID NO 241
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
cctttgtact gacagagcag tt                                      22

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
gcacacatca caaagcagtt                                         20

<210> SEQ ID NO 243
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
ctatgagttg aatggaaata tccgaaag                                        28

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
attgaactca aagcggctga a                                               21

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
agcgtttcaa acctctctag g                                               21

<210> SEQ ID NO 246
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
ttctgagaat gcttctgtct agatt                                           25

<210> SEQ ID NO 247
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
gtagaatctg caagtggata tttgg                                           25

<210> SEQ ID NO 248
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
aaaggcaatg ttcaactctg tg                                              22

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
gatattcccg tttccaacga aatc                                              24

<210> SEQ ID NO 250
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
gtctagagtt tatatgaaga caatccc                                           27

<210> SEQ ID NO 251
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
gtgtaaagga tcgttcagct ct                                                22

<210> SEQ ID NO 252
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gttgaacgca cacatcaca                                                    19

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
tgtgttcgtt caactcacag ag                                                22

<210> SEQ ID NO 254
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
cctccaagct atccaaatat cctc                                              24

<210> SEQ ID NO 255
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
ctcagaaact tctttgtgat gtgtg                                             25

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
tttctactat tgacctcaaa gcg                                          23

<210> SEQ ID NO 257
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
acaattggat aattggaacc ct                                           22

<210> SEQ ID NO 258
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
tcttagaatc ctatttgtga tgtgc                                        25

<210> SEQ ID NO 259
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
acttgtttgt gatgtgtgaa ct                                           22

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
ggccagaact tccaacacta t                                            21

<210> SEQ ID NO 261
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
tttacgtctg attgtgtgtt cc                                           22

<210> SEQ ID NO 262
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 262
ttaggatagt tagctcttct tgttg                                          25

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 263
aggttctgag aatgcttctc ttt                                            23

<210> SEQ ID NO 264
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 264
ctttgaggat ttcgtgggaa ac                                             22

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 265
aatctgggtg ctcctgtatt g                                              21

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 266
tggttccaag tctttgctat tg                                             22

<210> SEQ ID NO 267
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 267
ggatcgttca actctgtcag tt                                             22

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
aaatgtctgt ctgggcatga t                                              21

<210> SEQ ID NO 269
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ctccacttgc aaattccaca aa                                             22

<210> SEQ ID NO 270
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
tctgtctagc agaatatgaa gaaatcc                                        27

<210> SEQ ID NO 271
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
ggatagagtc aagacccatc ag                                             22

<210> SEQ ID NO 272
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ggttgcaatc ctagtctctg ataaa                                          25

<210> SEQ ID NO 273
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
tctgcaagtg gatattcaga cc                                             22

<210> SEQ ID NO 274

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
cctggccagc aacaaaga                                                 18

<210> SEQ ID NO 275
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
gaagatattt cctttctcac catagac                                       27

<210> SEQ ID NO 276
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
agagcagtta ggaaacactc tg                                            22

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
ccagtctatt attgatgggc attt                                          24

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
cctttgtgat gtgtgcgttc                                               20

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
aatctgggtg ctcctgtatt g                                             21

<210> SEQ ID NO 280
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
tggaatcaac atcaaacgga aa                                            22

<210> SEQ ID NO 281
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
tcttcataga gcagtttgga aaga                                          24

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
ctctcaaagg gaatgttcaa ctc                                           23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
tcgatgatga tcacactgga ttt                                           23

<210> SEQ ID NO 284
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
tctgtgatgt ctgcattcaa gt                                            22

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
ggccagaact tccaacacta t                                             21

<210> SEQ ID NO 286
<211> LENGTH: 23
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 286
ggaataatcc atggactcga atg         23

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 287
acaaacagag tgtttccaaa ctg         23

<210> SEQ ID NO 288
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 288
ttgatatcat agctcagacc atacc         25

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 289
gcgcttgaaa tctccacttg         20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 290
tattgcttcc gtggagtgtg         20

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
acccaaactg ggattagata c         21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 292
ctggattact ccggtctgaa c                                              21

<210> SEQ ID NO 293
<211> LENGTH: 19
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 293
ggtgagggag gttgaagtg                                                 19

<210> SEQ ID NO 294
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 294
ggctaggagg gtgttgatta tt                                             22

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 295
ggtgtgcctt gtggtaagaa                                                20

<210> SEQ ID NO 296
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 296
agaagcttat gttgtttatg cg                                             22

<210> SEQ ID NO 297
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 297
gggtggagag ttctgtagat gt                                             22

<210> SEQ ID NO 298
<211> LENGTH: 25
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 298
tccaattctg tgaagaaagt cattg                                           25

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
acctaggaat ccaacttaca agg                                             23

<210> SEQ ID NO 300
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
accttgggca gtatggc                                                    17

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
acataatgtt ggaagttcta gcca                                            24

<210> SEQ ID NO 302
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
tccaattctg tgaagaaagt cattg                                           25

<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
gttcttccat ttgtttgtct cctc                                            24

<210> SEQ ID NO 304
<211> LENGTH: 28
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 304
cacaataata atgggagact ttaacacc                                              28

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
atctgagagc ctgtttgtta tga                                                   23

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
cccatcaagc taccaatgac t                                                     21

<210> SEQ ID NO 307
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tggtatcagt accatgctgt tt                                                    22

<210> SEQ ID NO 308
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
tgtagccttg tagtatagtt tgaagtc                                               27

<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
aatggaagaa cattccatac tcgt                                                  24

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
tctctcacca ctcccattca                                              20

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
agcaacttca gcaaagtctc a                                            21

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
ggtacaagta ccatgctgtt                                              20

<210> SEQ ID NO 313
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
ttgtatcctg agactttgct gaa                                          23

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
tgattgcact gtggtctgag                                              20

<210> SEQ ID NO 315
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
cactgtcaac attagacaga tcaac                                        25

<210> SEQ ID NO 316
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 316
acagagatat agaccaatgg aacag                                          25

<210> SEQ ID NO 317
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
aatggaagaa cattccatgc tca                                            23

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
atttcgttga gcagtggttt g                                              21

<210> SEQ ID NO 319
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
ggtaatttat agattcaatg ccatccc                                        27

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
agtttctgag aatgcttctg tcta                                           24

<210> SEQ ID NO 321
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
caacgaaatc ctcaaagcta tcc                                            23

<210> SEQ ID NO 322
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
```
agggaatatt caactctgtg act                                          23

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
ttctaccgtt ggcctcaaag                                              20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
tcatcatagg cctcaaagcg                                              20

<210> SEQ ID NO 325
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
tttctacatg tggcctaaat gtgct                                        25

<210> SEQ ID NO 326
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
aaagagtgtt tccaaactgc tg                                           22

<210> SEQ ID NO 327
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
gaagtttctg tgaatgatgc tgtc                                         24

<210> SEQ ID NO 328
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
gaaatcccgt tccaacgaa g                                                    21

<210> SEQ ID NO 329
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
ggttcatctc tgttagttga atacac                                              26

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
tttctaccgt tggcctcaaa                                                     20

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
tcacaaagca gattctgata atgc                                                24

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
ctgctctatg aaacgaatgt tcaa                                                24

<210> SEQ ID NO 333
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
caggagcacc cagattcata aag                                                 23

<210> SEQ ID NO 334
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
aaatacctag gaatccacct tacaa                                               25

<210> SEQ ID NO 335
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 335
tccaattctg tgaagaaagt cattg                                          25

<210> SEQ ID NO 336
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 336
gcattcttat acaccaacaa caga                                           24

<210> SEQ ID NO 337
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 337
ttgtatcctg agactttgct gaag                                           24

<210> SEQ ID NO 338
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 338
ctcccattca caattgctac aaa                                            23

<210> SEQ ID NO 339
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 339
atcacaagca ttcttataca ccaac                                          25

<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 340
tttgcaatag gtgtggtgat g                                              21

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
tcaacattag acagatcaac gaga                                          24

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
ggtaccagta ccatgctgtt t                                             21

<210> SEQ ID NO 343
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
gctaccaatg actttcttca cag                                           23

<210> SEQ ID NO 344
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
atggaagaac attccatgct ca                                            22

<210> SEQ ID NO 345
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
tccaattctg tgaagaaagt cattg                                         25

<210> SEQ ID NO 346
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
ttgtatcctg agactttgct gaag                                          24

-continued

<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
cttgaagagg tccttcacgt c                                                  21

<210> SEQ ID NO 348
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
gctcatggat aggaagaatc aa                                                 22

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
aagcattccc tttgaaagct g                                                  21

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
agacagatca acgagacaga aag                                                23

<210> SEQ ID NO 351
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
ctgagttcta gtttgattgc actg                                               24

<210> SEQ ID NO 352
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
gtgtaaggaa gggatccagt tt                                                 22

<210> SEQ ID NO 353

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
tccaattctg tgaagaaagt cattg                                          25

<210> SEQ ID NO 354
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
tcacaagcat tcctatacac ca                                             22

<210> SEQ ID NO 355
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
gctctatcct gttccattgg tc                                             22

<210> SEQ ID NO 356
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
tttgtagaat ctgcaggtgg at                                             22

<210> SEQ ID NO 357
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
ctttgtgatg tttgcattca agtc                                           24

<210> SEQ ID NO 358
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
ttcaggcctg tggtgaaa                                                  18

<210> SEQ ID NO 359
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
actactttgg tacgtgtgtg tt                                              22

<210> SEQ ID NO 360
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
tgtgtgttct caactaacag agt                                             23

<210> SEQ ID NO 361
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
ttgtgatgtg tgcgttcaat tc                                              22

<210> SEQ ID NO 362
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
aagtagacag cagcattctc ag                                              22

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
gatggtgcag tttggaaaca c                                               21

<210> SEQ ID NO 364
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
ctcagtgagt tgaacctttc tttag                                           25

<210> SEQ ID NO 365
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 365
gtcacagagt agaatgttcc ctt                                          23

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
tgaggcctta gttggaaacg                                              20

<210> SEQ ID NO 367
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
atgatgagtg tactcaaaga acaga                                        25

<210> SEQ ID NO 368
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
ttgatacagc agtttggaaa cac                                          23

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
gcacacgtat gtttatcgca                                              20

<210> SEQ ID NO 370
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
agacggagtc tcgctctg                                                18

<210> SEQ ID NO 371
<211> LENGTH: 25
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 371
catgtgtctt tatagcagca tgatt                                           25

<210> SEQ ID NO 372
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
gtgtccatgt gttctcattg ttc                                             23

<210> SEQ ID NO 373
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
tcccacagaa taataatggg agaat                                           25

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
tggtaccagt tgttcctttc c                                               21

<210> SEQ ID NO 375
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
ttgttgcgat agtttactga gaatg                                           25

<210> SEQ ID NO 376
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
ctctatactt cccttctcgc ttc                                             23

<210> SEQ ID NO 377
<211> LENGTH: 25
<212> TYPE: DNA
<213> ORGANISM: Artificial Sequence
<220> FEATURE:

<223> OTHER INFORMATION: Description of Artificial Sequence: Synthetic
    primer

<400> SEQUENCE: 377
atccagtcta tcattgttgg acatt                                    25

<210> SEQ ID NO 378
<211> LENGTH: 18
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 378
aggcatgggc aaggattt                                            18

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 379
tgctgaggga tctgctctta                                          20

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 380
gatcacgagg tcaggagatt g                                        21

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 381
ctgctataaa ggcacatgca c                                        21

<210> SEQ ID NO 382
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 382
gtggtctgag agacagtttg tt                                       22

<210> SEQ ID NO 383
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 383
acatacgtgt gcatgtgtct t                                         21

<210> SEQ ID NO 384
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
tcaacatagt attggaagtt ctgg                                      24

<210> SEQ ID NO 385
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
ggtcaggagt tcgagacca                                            19

<210> SEQ ID NO 386
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
gtgtctgtgt agaaagaagt aga                                       23

<210> SEQ ID NO 387
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
gaaaccaaca agaacaaaga cac                                       23

<210> SEQ ID NO 388
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
ctctgtttgt ctgttattgg tgtataag                                  28

<210> SEQ ID NO 389
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 389
ttgttcttgt gatagtttgc tgag                                            24

<210> SEQ ID NO 390
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
ataagttagg gaggattccc tctt                                            24

<210> SEQ ID NO 391
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
gagagatcca ctgttagtct gatgg                                           25

<210> SEQ ID NO 392
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
caggctggag tgcagtg                                                    17

<210> SEQ ID NO 393
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
ttgggatata aacccaaagg at                                              22

<210> SEQ ID NO 394
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
tcaacttctt tgcctttggt tt                                              22

<210> SEQ ID NO 395
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 395
aggtattgat gggatgtatc tcaaa                                           25

<210> SEQ ID NO 396
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
attcctgagt tctagtttgg ttaca                                           25

<210> SEQ ID NO 397
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
ctggtaccat tccttctgaa acta                                            24

<210> SEQ ID NO 398
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
accgctagca agactaataa ag                                              22

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
tgacatgggt ctcctgaata c                                               21

<210> SEQ ID NO 400
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
cctttgtgat gtgtgtgttc aa                                              22

<210> SEQ ID NO 401
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
cacccactcc agcatataaa ca                                              22

<210> SEQ ID NO 402
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
cctccaagct atccaaatat cca                                             23

<210> SEQ ID NO 403
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403 tacccttttct tccagttgat cg                                             22

<210> SEQ ID NO 404
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
ggatgcatgg ctggttcaa                                                  19

<210> SEQ ID NO 405
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
tgttgattgg aatagtttca gaagg                                           25

<210> SEQ ID NO 406
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
tgcatatatt gaaccagcct ttc                                             23

<210> SEQ ID NO 407
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407

```
ggaaaccttc aaatctatcc aaatatcc                                         28

<210> SEQ ID NO 408
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
tgggttgttt gtgcattgat tt                                               22

<210> SEQ ID NO 409
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
ctctcagacc acagtgcaat c                                                21

<210> SEQ ID NO 410
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
tggtttgaaa gtcctcctgt ag                                               22

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
ccatgatcaa gtgggcttca                                                  20

<210> SEQ ID NO 412
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
gaagcaattg tgaatgggag ttt                                              23

<210> SEQ ID NO 413
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
gagttaggga ggattccctc tt                                               22
```

<210> SEQ ID NO 414
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
ttggtttggt ttgccagtat tt                                              22

<210> SEQ ID NO 415
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
ctgtttacat gctggattac gttta                                           25

<210> SEQ ID NO 416
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
ctcggagtag tttgatcgtc tg                                              22

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
ctctgcctgg ctttggtatc                                                 20

<210> SEQ ID NO 418
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
ctggagtgga cctccaaa                                                   18

<210> SEQ ID NO 419
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
acttagataa ccacagccta agaa                                            24

<210> SEQ ID NO 420
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 420
ggatggaatg cccaacaaat ac                                               22

<210> SEQ ID NO 421
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 421
gcagcctcta ctattcctta cttt                                             24

<210> SEQ ID NO 422
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 422
gcttcaaatg ccactttgtt tac                                              23

<210> SEQ ID NO 423
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 423
cagtcctaaa gagggagaca ttatt                                            25

<210> SEQ ID NO 424
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 424
ttgtccttgc aatagtttgc t                                                21

<210> SEQ ID NO 425
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 425
cctataatcc cagcactttg gg                                               22

<210> SEQ ID NO 426
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 426
tagttcaacc agtgtggaag ac                                    22

<210> SEQ ID NO 427
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 427
cacgtatgtt tattgcggca t                                     21

<210> SEQ ID NO 428
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 428
tctgttgatt tggtgtggag ag                                    22

<210> SEQ ID NO 429
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 429
agacaagcaa atgctgagag a                                     21

<210> SEQ ID NO 430
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 430
tgctgctcta aagacacatg c                                     21

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 431
aaccaaggct cgagaactac                                       20

<210> SEQ ID NO 432

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
tttacactgt tggtgggact g                                           21

<210> SEQ ID NO 433
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
ttgtttgagt tcattgtaga ttccg                                       25

<210> SEQ ID NO 434
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
ggagaatgga accaagttgg aa                                          22

<210> SEQ ID NO 435
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
acggagtctc agtctgtcg                                              19

<210> SEQ ID NO 436
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
gtccttgcga tagtttactg aga                                         23

<210> SEQ ID NO 437
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
gacagatcca tgagacagaa gc                                          22

<210> SEQ ID NO 438
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
aaacaacaga tgctggagag g                                            21

<210> SEQ ID NO 439
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
gtatcctgag actttgctga ag                                           22

<210> SEQ ID NO 440
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
caggctggag tgcagtg                                                 17

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
gggtaaggtc acagatcaac                                              20

<210> SEQ ID NO 442
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
aattgtgatg ttagggtgtc aa                                           22

<210> SEQ ID NO 443
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 443
ctggcagaag acagcgat                                                18

<210> SEQ ID NO 444
<211> LENGTH: 26
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 444
gagacattac tgacaatagc aaagac                                          26

<210> SEQ ID NO 445
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
tggataaatt cctcgacaca tacac                                           25

<210> SEQ ID NO 446
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
caatctagca aggcaggcca a                                               21

<210> SEQ ID NO 447
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
tggtggacgc ctgtagt                                                    17

<210> SEQ ID NO 448
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
tttgtccttg caatacttta ctgag                                           25

<210> SEQ ID NO 449
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
aacccatctg tacatcatca tca                                             23

<210> SEQ ID NO 450
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 450 ccctttatttctttctcctgcct                                             23

<210> SEQ ID NO 451
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
gtatcctgag actgtgctga ag                                            22

<210> SEQ ID NO 452
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
gcgtatattg aaccagcctt g                                             21

<210> SEQ ID NO 453
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
cccaatttca gctcctgtt                                                19

<210> SEQ ID NO 454
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
agtaccagcc actgcaaa                                                 18

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
cgtggaattt gcaagtggag                                               20

<210> SEQ ID NO 456
<211> LENGTH: 26
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 456
gaataagagt ggtaagagag gacatc                                        26

<210> SEQ ID NO 457
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
tcacagaata gaatgttccc tgtta                                         25

<210> SEQ ID NO 458
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
aacgcagttc ctcaccag                                                 18

<210> SEQ ID NO 459
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
gtgtgggttt gtcatagata gctc                                          24

<210> SEQ ID NO 460
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
ctagacatgt acactctctc aagac                                         25

<210> SEQ ID NO 461
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
ggtaccattc cttctgaaac tattc                                         25

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 462
tatctgcaag cggacgtttc                                              20

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
ggatgcaagg ctggttcaat a                                            21

<210> SEQ ID NO 464
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
ttagatcttt cctgctttct cttgt                                        25

<210> SEQ ID NO 465
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
catcaccatc atcaaagacc aaa                                          23

<210> SEQ ID NO 466
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
tttggtgtgg gtttgtcata aatag                                        25

<210> SEQ ID NO 467
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 467
aggaactcaa attgtccctg tt                                           22

<210> SEQ ID NO 468
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 468
gtctctgccc ggctttg                                                  17

<210> SEQ ID NO 469
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 469
gtatattgaa ccagccttgc atc                                           23

<210> SEQ ID NO 470
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 470
ccctttcttg tgccagttt                                                19

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 471
tgagggtcct gtctgttaga                                               20

<210> SEQ ID NO 472
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
agaatgatgc tggcctcata aa                                            22

<210> SEQ ID NO 473
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 473
taacagtcag gaccctcag                                                19

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 474
cccggcagac caatagttta                                              20

<210> SEQ ID NO 475
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 475
accactgtat acttaatgcc tgag                                         24

<210> SEQ ID NO 476
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 476
gtggagtgtg tggtatgtgt ag                                           22

<210> SEQ ID NO 477
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 477
aggtaaattg aattaaggct cctg                                         24

<210> SEQ ID NO 478
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 478
tcacaatcaa ggaccgctat g                                            21
```

METHODS FOR TREATING AND DETECTING SEPSIS IN HUMANS

RELATED APPLICATIONS

This application claims priority of U.S. Provisional Application No. 62/711,970 filed Jul. 30, 2018, the entirety of which is incorporated herein by reference for all purposes.

SEQUENCE LISTING

The instant application contains a Sequence Listing which has been submitted electronically in ASCII format and is hereby incorporated by reference in its entirety. Said ASCII copy, created on Jul. 25, 2019, is named 176395-010601_SL.txt and is 185,649 bytes in size.

FIELD OF INVENTION

Polynucleotides relating to circulating nucleic acids (CNAs) indicative of sepsis are described herein, as are probes, methods, and kits for detecting and diagnosing sepsis in humans. Also encompassed herein are probes, methods, and kits for detecting CNAs described herein in samples. In a particular embodiment, the CNAs are detected in samples isolated from humans.

BACKGROUND

Sepsis, also known as systemic inflammatory response syndrome, is a leading cause of mortality in mammals and is characterized by symptoms that include fever, elevated heart and breathing rate, and organ failure. Even under the best of care, sepsis can lead to septic shock which is frequently fatal. Sepsis is linked to immune responses to infection and more particularly to an excessive inflammatory immune response. Bacterial infections are the most common infection associated with sepsis, but fungal, viral, and parasitic infections can also lead to sepsis. Sepsis arises from a complicated interactive network of the causative agent (e.g., a bacterial infection) and the host immune system response to the agent. The genetic background of the host and the status of the host immune system contribute to the potential for developing sepsis and severity of the condition once developed. Early phases of sepsis are typically associated with high levels of inflammation due to the release of inflammatory cytokines, such as high mobility group box 1 protein (HMGB1) and tumor necrosis factor-alpha (TNF-α), interleukin-1 (IL-1), and interleukin-6 (IL-6). The dramatic release of such inflammatory cytokines, wherein a positive feedback loop is established between the cytokines and white blood cells, is referred to as a cytokine storm (also known hypercytokinemia or cytokine cascade). Later phases of sepsis are somewhat paradoxically associated with prolonged periods of reduced immune system activity.

SUMMARY

Methods, reagents, and kits described herein relate to predicting and/or diagnosing sepsis in a human in advance of the appearance of sepsis symptoms in the human. In accordance with the present experimental findings, methods, reagents, and kits described herein can be used to predict/diagnose sepsis in a human subject in advance of symptomatic presentation as well as in later stages of the disease progress. Indeed, results presented herein demonstrate that methods, reagents, and kits described herein can diagnose sepsis in a human subject at least three days in advance of clinical presentation. In light of results presented in the examples, over-representation or under-representation of at least one polynucleotide relative to an internal reference region in a biological sample or body fluid sample (e.g., serum), wherein the at least one polynucleotide comprises any one of SEQ ID NOs: 1-57 or 94-148, is a positive indicator that a human subject from which the sample was isolated is developing sepsis. Accordingly, the methods, reagents, and kits described herein provide for diagnosis of sepsis at early, pre-symptomatic stages of the disease, as well as later stages of the disease. Methods for determining over-representation or under-representation of at least one polynucleotide (CNA) relative to an internal reference region, wherein the at least one polynucleotide comprises any one of SEQ ID NOs: 1-57 or 94-148, in body fluids are also disclosed, as are kits for such purposes, methods for screening the diagnostic target, and detection tests for screening. In a particular embodiment, the internal reference regions is at least one of SEQ ID NOs: 59, 61, or 68.

In a particular aspect, a method is presented comprising administering to a human identified as having sepsis a therapeutically effective amount of at least one agent used to treat sepsis, wherein the human is identified as having sepsis by analyzing a biological sample isolated from the human for over-representation or under-representation of at least one polynucleotide relative to an internal reference region, wherein the at least one polynucleotide comprises any one of SEQ ID NOs: 1-57 or 94-148 and wherein the over-representation or under-representation of the at least one polynucleotide in the biological sample is indicative of sepsis, thereby identifying the human as having sepsis.

In another particular aspect, a method is presented comprising administering to a human identified as having over-representation or under-representation of at least one polynucleotide relative to an internal reference region a therapeutically effective amount of at least one agent used to treat sepsis, wherein the human is identified as having over-representation or under-representation of at least one polynucleotide relative to an internal reference region by analyzing a biological sample isolated from the human for over-representation or under-representation of at least one polynucleotide relative to an internal reference region, wherein the at least one polynucleotide comprises any one of SEQ ID NOs: 1-57 or 94-148 and wherein the over-representation or under-representation of the at least one polynucleotide in the biological sample is a positive indicator that the human is in need of the administering.

In another particular aspect, a method is presented for detecting sepsis in a human, comprising
(a) analyzing a biological sample isolated from the human for over-representation or under-representation of at least one polynucleotide relative to an internal reference region, wherein the at least one polynucleotide comprises any one of SEQ ID NOs: 1-57 or 94-148, by contacting the biological sample with at least one synthetic probe specific for a polynucleotide comprising any one of SEQ ID NOs: 1-57 or 94-148, wherein the contacting generates complexes of synthetic probes bound to specific polynucleotides when at least one polynucleotide comprising any one of 1-57 or 94-148 is present in the biological sample, (b) detecting the complexes of synthetic probes bound to specific polynucleotides, and detecting the internal reference region in the biological sample, and (c) comparing the at least one polynucleotide comprising any one of SEQ ID NOs: 1-57 or 94-148 detected in the biological sample to the internal reference region detected in the biological sample to determine relative over-representation and under-representation of the at least one polynucleotide in the biological sample, wherein detection of the over-representation and under-representation of the at least one polynucleotide serves as a positive indicator of sepsis in the human.

In another particular aspect, a method is presented for detecting sepsis in a human, comprising analyzing a biological sample isolated from the human for over-representation or under-representation of at least one polynucleotide comprising any one of SEQ ID NOs: 1-57 or 94-148 relative to an internal reference region, wherein detection of over-representation or under-representation of the at least one said polynucleotide relative to the internal reference region in the biological sample is a positive indicator of sepsis in the human.

In another particular aspect, a method is presented for detecting sepsis in a human, comprising detecting at least one polynucleotide comprising any one of SEQ ID NOs: 1-57 or 94-148 in a biological sample obtained from the human wherein over-representation and under-representation of the at least one polynucleotide relative to an internal reference region in the biological sample is a positive indicator of sepsis in the human. The method may further comprising use of a therapeutically effective amount of at least one agent used to treat sepsis for treatment of the human.

In another particular aspect, a method is presented for evaluating representation of at least one polynucleotide comprising any one of SEQ ID NOs: 1-57 or 94-148 in a biological sample of a human, the method comprising: analyzing the biological sample of the human for over-representation or under-representation of at least one polynucleotide relative to an internal reference region, wherein the at least one polynucleotide comprises any one of SEQ ID NOs: 1-57 or 94-148, and wherein the over-representation or the under-representation of the at least one polynucleotide in the biological sample is determined by detecting the at least one polynucleotide comprising any one of SEQ ID NOs: 1-57 or 94-148 in the biological sample, wherein the detecting is achieved by contacting the biological sample with at least one reagent that specifically binds to any one of SEQ ID NOs: 1-57 or 94-148, detecting the internal reference region in the biological sample, and comparing the at least one polynucleotide comprising any one of SEQ ID NOs: 1-57 or 94-148 detected in the biological sample to the internal reference region detected in the biological sample to determine relative over-representation and under-representation of the at least one polynucleotide in the biological sample.

In a particular embodiment of any of the above methods, wherein the at least one polynucleotide comprises any one of SEQ ID NOs: 1-57 or 94-148 over-represented or under-represented relative to the internal reference region, the at least one is at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, or at least twenty-four of the polynucleotides comprising any one of SEQ ID NOs: 1-57 or 94-148.

In a particular embodiment of any of the above methods, the biological sample is blood, a product derived from blood, or a fraction derived from blood. In a more particular embodiment, the product derived from blood is plasma or serum.

In a particular embodiment of any of the above methods, the internal reference region comprises at least one polynucleotide comprising any one of SEQ ID NOs: 59, 61, or 68.

In a particular embodiment of any of the above methods, detecting the over-representation or under-representation of the at least one polynucleotide relative to an internal reference region comprises at least one of a polymerase chain reaction (PCR)-based detection method, a hybridization-based method, enzyme-linked immunosorbent assay (ELISA), radioimmunoassay (RIA), solid-phase enzyme immunoassay (EIA), mass spectrometry, or microarray analysis. In a more particular embodiment, the PCR-based detection method is performed using at least one primer pair, wherein each primer pair of the at least one primer pair is specific for any one of SEQ ID NOs: 1-57 or 94-148, and a primer pair specific for at least one of SEQ ID NOs: 59, 61, or 68. In a more particular embodiment, the primer pair specific for any one of SEQ ID NOs: 1-57 or 94-148 and the primer pair specific for at least one of SEQ ID NOs: 59, 61, or 68 is any one of the primer pairs presented in Tables 1-3. In another particular embodiment, the method further comprises sequencing amplification products corresponding to any one of SEQ ID NOs: 1-57 or 94-148 or at least one of SEQ ID NOs: 59, 61, or 68 generated by the PCR-based detection method. In another particular embodiment, the SEQ ID NOs: (nucleic acid sequences) comprise circulating nucleic acid. In another particular embodiment, the at least one agent used to treat sepsis comprises at least one of an antibiotic, anti-fungal agent, anti-viral agent, anti-parasitic agent, or fluids suitable for intravenous administration. In another particular embodiment, the human is monitored for sepsis. In another particular embodiment, the over-representation or under-representation of the at least one polynucleotide relative to an internal reference region is determined using reagents comprising an antibody or a nucleic acid probe specific for any one of SEQ ID NOs: 1-57 or 94-148 and at least one of SEQ ID NOs: 59, 61, or 68. In another particular embodiment, the nucleic acid probe specific for any one of SEQ ID NOs: 1-57 or 94-148 and at least one of SEQ ID NOs: 59, 61, or 68 is labeled with a detectable label.

In another aspect, a probe comprising a manmade nucleotide sequence that binds specifically to a polynucleotide comprising any one of SEQ ID NOs: 1-57 or 94-148 and at least one manmade tag conjugated thereto and at least one of SEQ ID NOs: 59, 61, or 68 and at least one manmade tag conjugated thereto, wherein the manmade nucleotide sequence is complementary to the polynucleotide comprising any one of SEQ ID NOs: 1-57 or 94-148 and at least one of SEQ ID NOs: 59, 61, or 68. In a particular embodiment, the manmade nucleotide sequence that binds specifically to a polynucleotide comprising any one of SEQ ID NOs: 1-57 or 94-148 and at least one of SEQ ID NOs: 59, 61, or 68 exhibits at least 90%, at least 91%, at least 92%, at least 93%, at least 94%, or at least 95%, at least 96%, at least 97%, at least 98%, or at least 99% complementarity to any one of SEQ ID NOs: 1-57 or 94-148 and at least one of SEQ ID NOs: 59, 61, or 68. In a particular embodiment, the manmade tag is a detectable marker. In a more particular embodiment, the detectable marker comprises a radioactive marker or fluorescent marker. In another embodiment, an array comprising at least one probe that binds specifically to any one of SEQ ID NOs: 1-57 or 94-148 and at least one of SEQ ID NOs: 59, 61, or 68 is presented, wherein the at least one probe is bound to a solid surface. In a particular embodiment, the array is used for diagnosing sepsis. In another embodiment, a kit comprising at least one probe that binds specifically to any one of SEQ ID NOs: 1-57 or 94-148 and at least one of SEQ ID NOs: 59, 61, or 68 is presented, wherein the kit further optionally comprises instructions for use thereof. In a particular embodiment, the kit is used for diagnosing sepsis. In another particular embodiment, the kit is used for detecting the indicated SEQ ID NOs: In embodiments thereof, the array or kit comprises comprising at least four, five, or ten different probes comprising a manmade nucleotide sequence that binds specifically to a polynucleotide comprising any one of the SEQ ID NOs: listed in Table 4 and at least one manmade tag conjugated thereto, wherein the manmade nucleotide sequence is complementary to the polynucleotide comprising any one of the SEQ ID NOs: listed in Table 4. In a particular embodiment, the array comprises a microarray, gene chip, DNA chip, or a FIL-MARRAY®.

In another aspect, a primer comprising, consisting essentially of, or consisting of a manmade nucleotide sequence that binds specifically to a polynucleotide comprising any one of the SEQ ID NOs: listed in Table 4 and at least one manmade tag conjugated thereto is presented, wherein the manmade nucleotide sequence is any one of the polynucleotide primer sequences or a primer pair listed in Tables 1-3 or a variant thereof. In a more particular embodiment, the variant of any one of the polynucleotide primer sequences listed in Tables 1-3 is at least 90%, at least 91%, at least 92%, at least 93%, at least 94%, or at least 95%, at least 96%, at least 97%, at least 98%, or at least 99% identical to any one of the polynucleotide sequences listed in Table 4. In another particular embodiment, the manmade tag is a detectable marker (e.g., a radioactive marker or fluorescent marker.

In another aspect, a kit for detecting sepsis in a human is presented comprising at least one primer pair for amplifying a polynucleotide comprising any one of the SEQ ID NOs: listed in Table 4, wherein the at least one primer pair is listed in Tables 1-3 and optionally, instructions for use thereof. In a particular embodiment, the at least one primer pair is four primer pairs and wherein each primer pair of the four primer pairs specifically amplifies a different polynucleotide comprising any one of the SEQ ID NOs: listed in Table 4. In another particular embodiment, the at least one primer pair is five primer pairs and wherein each primer pair of the five primer pairs specifically amplifies a different polynucleotide comprising any one of the SEQ ID NOs: listed in Table 4. In another particular embodiment, the at least one primer pair is ten primer pairs and wherein each primer pair of the ten primer pairs specifically amplifies a different polynucleotide comprising any one of the SEQ ID NOs: listed in Table 4.

In another aspect, use of a polynucleotide sequence comprising any one of the SEQ ID NOs: listed in Table 4 as a biomarker for the detection of sepsis in a human is encompassed herein. In a particular embodiment, the biomarker is a biomarker in a sample obtained from the human, wherein the sample is a sample of blood, a product derived from blood or a fraction derived from blood (e.g. plasma or serum)

In an aspect, a method for treating a human suspected of having sepsis is presented, the method comprising treating the human identified as having sepsis with a therapeutically effective amount of at least one agent used to treat sepsis, wherein the human is identifiable as having sepsis by analyzing a biological sample isolated from the human for over-representation or under-representation of at least one polynucleotide, wherein the at least one polynucleotide comprises any one of SEQ ID NOs: 1-57 or 94-148 and wherein the over-representation or under-representation of the at least one polynucleotide in the biological sample is a positive indicator of sepsis. In a particular embodiment thereof, the over-representation or the under-representation of the at least one polynucleotide is determined relative to an internal reference region. In a particular embodiment, the internal reference regions is at least one of SEQ ID NOs: 59, 61, or 68.

Also encompassed herein is a therapeutically effective amount of at least one agent used to treat sepsis or a composition thereof for use in a method of treating sepsis in a human identified as having sepsis, wherein the human is identified as having sepsis by analyzing a biological sample isolated from the human for over-representation or under-representation of at least one polynucleotide, wherein the at least one polynucleotide comprises any one of SEQ ID NOs: 1-57 or 94-148 and wherein the over-representation or under-representation of the at least one polynucleotide in the biological sample is a positive indicator of sepsis. The human may exhibit symptoms of sepsis or may be asymptomatic. In a particular embodiment thereof, the over-representation or the under-representation of the at least one polynucleotide is determined relative to an internal reference region. In a particular embodiment, the internal reference regions is at least one of SEQ ID NOs: 59, 61, or 68.

In another aspect, a method for treating a human identified as exhibiting over-representation or under-representation of at least one polynucleotide is presented, wherein the at least one polynucleotide comprises any one of SEQ ID NOs: 1-57 or 94-148 and wherein the over-representation or the under-representation of the at least one polynucleotide in the biological sample is a positive indicator of sepsis, the method comprising treating the human identified as exhibiting the over-representation or the under-representation of the at least one polynucleotide with a therapeutically effective amount of at least one agent used to treat sepsis. In a particular embodiment thereof, the over-representation or the under-representation of the at least one polynucleotide is determined relative to an internal reference region. In another particular embodiment, the human is identifiable as having sepsis by analysis of a biological sample isolated from the human for the over-representation or the under-representation of the at least one polynucleotide, wherein the over-representation or the under-representation of the at least one polynucleotide may optionally be determined relative to an internal reference region. In a particular embodiment, the internal reference regions is at least one of SEQ ID NOs: 59, 61, or 68.

In yet another aspect, a method for treating a human with early stage sepsis (e.g., pre-symptomatic sepsis) is presented, the method comprising treating the human with early stage sepsis with a therapeutically effective amount of at least one agent used to treat sepsis, wherein the human is identifiable as having early stage sepsis by analyzing a biological sample isolated from the human for over-representation or under-representation of at least one polynucleotide, wherein the at least one polynucleotide comprises any one of SEQ ID NOs: 1-57 or 94-148 and wherein the over-representation or under-representation of the at least one polynucleotide in the biological sample is a positive indicator of sepsis. In a particular embodiment thereof, the over-representation or the under-representation of the at least one polynucleotide is determined relative to an internal reference region. In a particular embodiment, the internal reference regions is at least one of SEQ ID NOs: 59, 61, or 68.

Also encompassed herein is a therapeutically effective amount of at least one agent used to treat sepsis or a composition thereof for use in a method of treating sepsis in a human identified with early stage sepsis, wherein the human is identified as having early stage sepsis by analyzing a biological sample isolated from the human for over-representation or under-representation of at least one polynucleotide, wherein the at least one polynucleotide comprises any one of SEQ ID NOs: 1-57 or 94-148 and wherein the over-representation or under-representation of the at least one polynucleotide in the biological sample is a positive indicator of sepsis. The human may exhibit symptoms of sepsis or may be asymptomatic. In a particular embodiment thereof, the over-representation or the under-representation of the at least one polynucleotide is determined relative to an internal reference region.

Methods described herein comprise embodiments wherein the at least one polynucleotide comprising any one of SEQ ID NOs: 1-57 or 94-148 over-represented or under-represented is at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty of the polynucleotides comprising SEQ ID NOs: 1-57 or 94-148. In a particular embodiment thereof, the over-representation or the under-representation of the at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty of the polynucleotides comprising SEQ ID NOs: 1-57 or 94-148 is determined relative to an internal reference region. In a particular embodiment, the internal reference regions is at least one of SEQ ID NOs: 59, 61, or 68.

In a further aspect, a method for evaluating representation of at least one polynucleotide comprising any one of SEQ ID NOs: 1-57 or 94-148 in a biological sample of a human is presented, the method comprising:

analyzing the biological sample of the human for over-representation or under-representation of at least one polynucleotide, wherein the at least one polynucleotide comprises any one of SEQ ID NOs: 1-57 or 94-148, and wherein the over-representation or the under-representation of the at least one polynucleotide in the biological sample is determined by detecting the at least one polynucleotide comprising any one of SEQ ID NOs: 1-57 or 94-148 in the biological sample, wherein the detecting is achieved by contacting the biological sample with at least one reagent that specifically binds to any one of SEQ ID NOs: 1-57 or 94-148, to determine relative over-representation and under-representation of the at least one polynucleotide in the biological sample. In a particular embodiment thereof, the over-representation or the under-representation of the at least one polynucleotide in the biological sample, when compared to an internal reference is determined; for example by quantitative real time polymerase chain reaction (RT-PCR). In accordance with methods described herein, amplification of regions of the CNAs represented by SEQ ID NOs: 1-57 or 94-148 involves a determination of how many amplification cycles are called for to reach a desired detection limit. In another particular embodiment, the over-representation or the under-representation of the at least one polynucleotide in the biological sample is determined by detecting the at least one polynucleotide comprising any one of SEQ ID NOs: 1-57 or 94-148 in the biological sample, wherein the detecting is achieved by contacting the biological sample with at least one reagent that specifically binds to any one of SEQ ID NOs: 1-57 or 94-148, and detecting the internal reference region in the biological sample, and comparing the at least one polynucleotide comprising any one of SEQ ID NOs: 1-57 or 94-148 detected in the biological sample to the internal reference region detected in the biological sample to determine relative over-representation and under-representation of the at least one polynucleotide in the biological sample. The over-representation or under-representation of the at least one polynucleotide may also be referred to herein as a deviation of the level of the at least one polynucleotide in the biological sample of an infected subject relative to the level of the at least one polynucleotide in a biological sample of a healthy subject.

Detection of the at least one polynucleotide may be achieved using RT-PCR as detailed herein as well as amplification free detection methods.

Methods described herein comprise embodiments wherein the biological sample is a bodily fluid, such as, without limitation, whole blood, a blood fraction, saliva, urine, sputum, cerebrospinal fluid, tears, sweat, milk, or interstitial fluid. In a particular embodiment, the biological sample is blood, a product derived from blood, or a fraction derived from blood. In a particular embodiment, the product derived from blood is plasma or serum.

Methods described herein comprise embodiments wherein detecting the over-representation or under-representation of the at least one polynucleotide comprises at least one of a PCR-based detection method (e.g., RT-PCR), a hybridization-based method, enzyme-linked immunosorbent assay (ELISA), radioimmunoassay (MA), solid-phase enzyme immunoassay (EIA), mass spectrometry, and microarray analysis. In a particular embodiment thereof, detecting the over-representation or under-representation of the at least one polynucleotide is determined relative to an internal reference region. In a particular embodiment, the internal reference regions is at least one of SEQ ID NOs: 59, 61, or 68.

In embodiments comprising a PCR-based detection method, the PCR-based detection method comprises amplifying nucleic acid sequences in the biological sample using primers that are specific for and capable of amplifying any one of SEQ ID NOs: 1-57 or 94-148, wherein the amplifying generates amplification products corresponding to any one of SEQ ID NOs: 1-57 or 94-148 when the biological sample comprises any one of SEQ ID NOs: 1-57 or 94-148. In embodiments comprising a PCR-based detection method, the PCR-based detection method is performed using at least one primer pair, wherein each primer pair of the at least one primer pair is specific for any one of SEQ ID NOs: 1-57 or 94-148. In a more particular embodiment thereof, the primer pair specific for any one of SEQ ID NOs: 1-57 or 94-148 is any one of the primer pairs presented in Table 1 or Table 3. In an even more particular embodiment thereof, the PCR-based detection method further comprises sequencing the amplification products corresponding to any one of SEQ ID NOs: 1-57 or 94-148. In a particular embodiment, the internal reference regions is at least one of SEQ ID NOs: 59, 61, or 68 and primer pairs therefor are presented in Table 2.

Methods described herein comprise embodiments wherein nucleic acid sequences comprise circulating nucleic acids.

Methods described herein comprise embodiments wherein the at least one agent used to treat sepsis comprises at least one of an antibiotic, anti-fungal agent, anti-viral agent, anti-parasitic agent, or fluids suitable for intravenous administration.

Methods described herein comprise embodiments wherein the human is monitored for sepsis.

Methods described herein comprise embodiments wherein the over-representation or under-representation of the at least one polynucleotide is determined using reagents comprising an antibody or a nucleic acid probe specific for any one of SEQ ID NOs: 1-57 or 94-148. In a particular embodiment thereof, the over-representation or under-representation of the at least one polynucleotide is determined relative to an internal reference region. In a more particular embodiment, the antibody is a monoclonal or a polyclonal antibody. In a still more particular embodiment, the antibody is obtained from mice, rats, rabbits, goats, chicken, donkey, horses or guinea pigs.

Methods described herein comprise embodiments wherein a nucleic acid probe specific for any one of SEQ ID NOs: 1-57 or 94-148 is labeled with a detectable label.

In another aspect, a probe comprising a manmade nucleotide sequence capable of binding specifically to a polynucleotide comprising any one of SEQ ID NOs: 1-57 or 94-148 and at least one manmade tag conjugated thereto is presented, wherein the manmade nucleotide sequence is complementary to the polynucleotide comprising any one of SEQ ID NOs: 1-57 or 94-148. In a particular embodiment thereof, the manmade nucleotide sequence capable of binding specifically to a polynucleotide comprising any one of SEQ ID NOs: 1-57 or 94-148 exhibits at least 90%, at least 91%, at least 92%, at least 93%, at least 94%, or at least 95%, at least 96%, at least 97%, at least 98%, or at least 99% complementarity to any one of SEQ ID NOs: 1-57 or 94-148. In another particular embodiment, the manmade tag is a detectable marker. In a still more particular embodiment, the detectable marker comprises a radioactive marker or fluorescent marker.

Also encompassed herein is an array comprising at least one probe described herein, wherein the at least one probe is bound to a solid surface. Such arrays may comprise a microarray, gene chip, DNA chip, a FILMARRAY®, or a similar array.

Kits comprising at least one probe described herein and instructions for use thereof are also encompassed.

In a particular embodiment, the array or kit described herein comprises at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty different probes comprising a manmade nucleotide sequence capable of binding specifically to corresponding polynucleotides comprising any one of SEQ ID NOs: 1-57 or 94-148 and at least one manmade tag conjugated thereto, wherein the manmade nucleotide sequence is complementary to the polynucleotide comprising any one of SEQ ID NOs: 1-57 or 94-148. In a particular embodiment, the array or kit described herein comprises at least four different probes comprising a manmade nucleotide sequence capable of binding specifically to a polynucleotide comprising any one of SEQ ID NOs: 1-57 or 94-148 and at least one manmade tag conjugated thereto, wherein the manmade nucleotide sequence is complementary to the polynucleotide comprising any one of SEQ ID NOs: 1-57 or 94-148. In a more particular embodiment, the array or kit described herein comprises at least eight different probes comprising a manmade nucleotide sequence capable of binding specifically to a polynucleotide comprising any one of SEQ ID NOs: 1-57 or 94-148 and at least one manmade tag conjugated thereto, wherein the manmade nucleotide sequence is complementary to the polynucleotide comprising any one of SEQ ID NOs: 1-57 or 94-148.

Also encompassed herein is a primer comprising a manmade nucleotide sequence capable of binding specifically to a polynucleotide comprising any one of SEQ ID NOs: 1-57 or 94-148 and at least one manmade tag conjugated thereto, wherein the manmade nucleotide sequence is any one of the polynucleotide sequences listed in Table 1 or Table 3 as a forward primer or a variant thereof or as a reverse primer or a variant thereof. In an embodiment thereof, the variant of any one of the primer sequences listed in Table 1 or Table 3 is at least 90%, at least 91%, at least 92%, at least 93%, at least 94%, or at least 95%, at least 96%, at least 97%, at least 98%, or at least 99% identical to any one of the primer sequences listed in Table 1 or Table 3. In a particular embodiment, a variant of a primer comprises different nucleotides at the 5' end of the primer, which positions are more tolerant of variations thereto. In a particular embodiment, the manmade tag is a detectable marker (e.g., a radioactive marker, fluorescent dye), a tag that is specifically recognized (e.g., bound) by a labeled reagent (e.g., a labeled antibody), a tag that is specifically bound by a magnetic bead, or any other marker comprising detectable label.

Also encompassed herein are primers and probes for use in detecting the at least one polynucleotide described herein, wherein when using a TaqMan system, the detection of a particular polynucleotide sequence requires two specific primers (a forward and reverse primer pair specific for the polynucleotide sequence) and a probe (labeled oligonucleotide specific for the polynucleotide sequence). A labeled probe may, for example, be a TaqMan probe comprising a fluorescent label at a first terminus and a quencher at a second terminus whereby upon probe displacement during quantitative PCR (qPCR), the probe is cleaved, thus releasing the fluorescent label from the vicinity and effects of the quencher. Upon release from the vicinity/effects of the quencher, a higher fluorescence is emitted from the fluorescent label, which can be detected and quantitated to reflect the level/amount of the particular polynucleotide sequence present in a sample.

Also encompassed herein are methods for amplification-free detection of the at least one polynucleotide described herein, wherein such methods comprise a pair of oligonucleotide probes which are specific for the particular polynucleotide and are differentially labeled such that when each is bound to the polynucleotide and therefore in close proximity, the signal emitted from the probes changes. With respect to oligonucleotide probes that are labeled with fluorescent tags, close proximity of the fluorescent tags when bound to the polynucleotide is detected by an increase in fluorescence emissions.

Also encompassed herein is a primer consisting essentially of or consisting of a manmade nucleotide sequence capable of binding specifically to a polynucleotide comprising any one of SEQ ID NOs: 1-57 or 94-148 and at least one manmade tag conjugated thereto, wherein the manmade nucleotide sequence is any one of the polynucleotide sequences listed in Table 1 or Table 3 or a variant thereof. In an embodiment thereof, the variant of any one of the polynucleotide sequences listed in Table 1 or Table 3 is at least 90%, at least 91%, at least 92%, at least 93%, at least 94%, or at least 95%, at least 96%, at least 97%, at least 98%, or at least 99% identical to any one of the polynucleotide sequences listed in Table 1 or Table 3. In a particular embodiment, the manmade tag is a detectable marker (e.g., a radioactive marker or fluorescent marker).

Primer pairs complementary to SEQ ID NOs: 1-57 or 94-148 and suitable for PCR amplification are readily determined based on the sequences of SEQ ID NOs: 1-57 or 94-148 (5' to 3' strands) and reverse strands thereof (3' to 5' strands). Such primers are typically 8-20 nucleotides in length and are complementary (e.g., exhibit perfect complementarity or may be variants thereof that maintain a degree of complementarity sufficient to bind and act as primers in a PCR amplification) to any one of SEQ ID NOs: 1-57 or 94-148 or a reverse strand thereof. Choices regarding primer pairs suitable for PCR amplification are also determined based on the guanine/cytosine content of a potential primer sequence and the distance between the primers in a pair when bound to the target polynucleotide, with the understanding that PCR amplification products must be of a detectable size.

In another embodiment, therapeutic efficacy of a treatment regimen may be evaluated based on a change in the over-representation or under-representation of at least one of SEQ ID NOs: 1-57 or 94-148 following onset of the treatment regimen. In a particular embodiment, a decrease in representation of a CNA that is over-represented in sepsis (e.g., SEQ ID NOs: 94-148) is indicative that the treatment regimen is therapeutically effective. In another particular embodiment, an increase in representation of a CNA that is under-represented in sepsis (e.g., SEQ ID NOs: 1-57) is indicative that the treatment regimen is therapeutically effective.

Also encompassed herein is an array comprising at least one primer listed in Table 1 or Table 3, wherein the at least one primer is bound to a solid surface.

A kit for detecting sepsis in a human is also described, wherein the kit comprises at least one primer pair for amplifying a polynucleotide comprising any one of SEQ ID NOs: 1-57 or 94-148, wherein the at least one primer pair is listed in Table 1 or Table 3 or a functional variant thereof or a primer that may be determined based on any one of the sequences designated herein as SEQ ID NOs: 1-57 or 94-148 and instructions for use thereof. In a particular embodiment, the at least one primer pair is four primer pairs and each primer pair of the four primer pairs specifically amplifies a different polynucleotide comprising any one of SEQ ID NOs: 1-57 or 94-148. In another particular embodiment, the at least one primer pair is eight primer pairs and each primer pair of the eight primer pairs specifically amplifies a different polynucleotide comprising any one of SEQ ID NOs: 1-57 or 94-148.

Additional aspects of the present invention will be apparent in view of the description which follows.

Additional aspects of the present invention will be apparent in view of the description which follows.

BRIEF DESCRIPTION OF THE FIGURES AND TABLES

The invention will now be described in relation to the drawings and tables.

FIGS. 1A-H presents Table 1, wherein each of the sequences corresponds to a CNA and is designated SEQ ID NO: 1-57 in consecutive order. SEQ ID NOs: 1-57 are positive indicators of sepsis that are more highly represented in healthy controls and thus, a decrease in copy number is observed during infection. Accordingly, a decrease in copy number of any one of SEQ ID NOs: 1-57 is a positive indicator of sepsis. Forward and reverse primers suitable for PCR amplification of each of SEQ ID NOs: 1-57 are presented in the same row as the CNA for which they are specific.

Figure 2D:
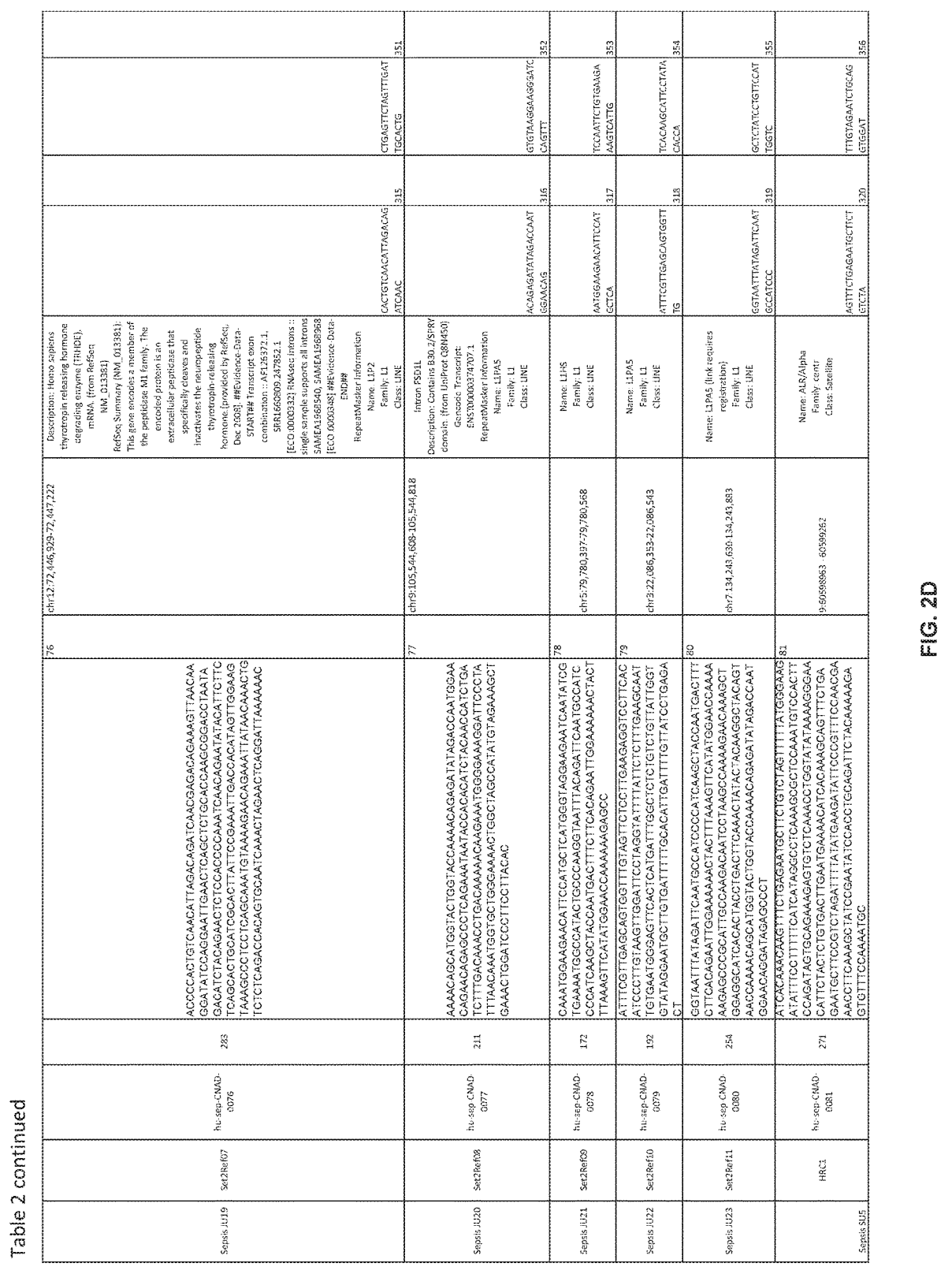
Figure 2E:
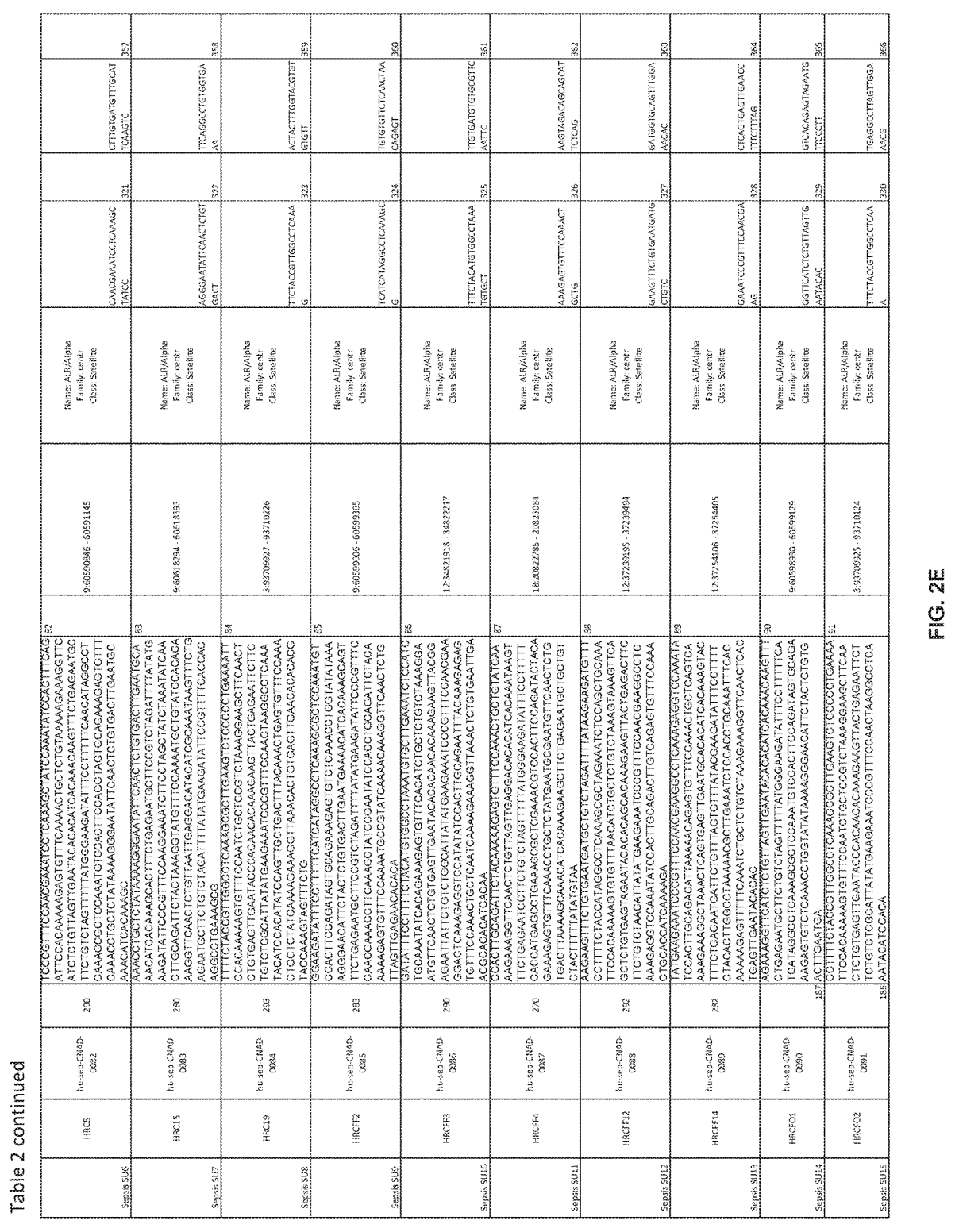

FIGS. 2A-F presents Table 2, wherein each of the Sequences corresponds to a CNA and is designated SEQ ID NO: 58-93 in consecutive order. SEQ ID NOs: 58-93 are equally represented in copy number in healthy controls and subjects afflicted with sepsis. Forward and reverse primers suitable for PCR amplification of each of SEQ ID NOs: 58-93 are presented in the same row as the CNA for which they are specific.

FIGS. 3A-I presents Table 3, wherein each of the Sequences corresponds to a CNA and is designated SEQ ID NO: 94-148 in consecutive order. SEQ ID NOs: 94-148 are positive indicators of sepsis that increase in copy number during infection. Forward and reverse primers suitable for PCR amplification of each of SEQ ID NOs: 94-148 are presented in the same row as the CNA for which they are specific.

DETAILED DESCRIPTION OF THE INVENTION

Various embodiments will be described in detail with reference to the drawings and tables. Reference to various embodiments does not limit the scope of the claims attached hereto. Additionally, any examples set forth in this specification are not intended to be limiting and merely set forth some of the many possible embodiments.

Methods, reagents, and kits described herein relate to detection and analysis of cell-free DNA available in the blood following active secretion, cell death or apoptosis. The present inventors have demonstrated that cell-free DNA indicative of sepsis can be detected in blood up to 2-3 days prior to clinical diagnosis of sepsis according to Sepsis-3-definition (defined below in accordance with current medical standards). Traditional biomarkers such as lactate, procalcitonin and others are measured only after clinical sepsis is evident from the patient's vital signs or labs. In high-risk patients, this may be too late to prevent the body's cascade of cytokine release, the harbinger of development for sepsis sequelae.

Accordingly, the lead-time provided by the present methods, reagents, and kits identifies subjects requiring heightened attention and monitoring. In particular embodiments, the present methods, reagents, and kits provide information on which basis a medical practitioner may initiate appropriate therapy and identify the site of infection, which may require source control, before the onset of irreversible organ dysfunction and widespread cellular hypoxia that occurs during the later stages of sepsis in septic patients.

Further to the above, methods described herein are based on the analysis of circulating nucleic acids, which are present in, for example, serum and plasma of humans. The composition and relative abundance of circulating nucleic acids varies depending on disease state. The present inventors identified particular genomic regions that do not change in relative abundance of specific regions of cirulating nucleic acids between sepsis patients and controls (non-sepsis), which genomic regions are designated internal reference regions. Genomic regions that significantly vary in abundance between sepsis patients and controls were also identified and designated disease motifs. Relative abundance for disease motifs can be examined using Real-Time Polymerase Chain Reaction (RT-PCR) to determine if an "unknown" sample can be identified as exhibiting features characteristic of sepsis or features characteristic of non-sepsis. In a particular embodiment, identifying a sample as exhibiting features characteristic of sepsis may be used to predict onset of sepsis or diagnose sepsis.

It is to be understood that combinations of primers binding to genomic regions that significantly vary in coverage and abundance between sepsis patients can be optimized. The RT-PCR assay can be designed based at least in part on primers used and such an assay can be used to identify early features of sepsis.

Probes, methods, and kits described herein can analyze cell free DNA (cfDNA) collected at a preclinical stage of sepsis and accurately determine which patients will go on to develop sepsis. This preclinical phase includes patients that already have molecular evidence of an infection but have not yet manifested traditional criteria including vital sign abnormalities, fever and laboratory changes (according to the Sepsis-3-definition).

Early identification of sepsis, formerly known as septicaemia, is clinically valuable because sepsis has a high morbidity and mortality rate in mammals in general and, even under the best of care, in humans. Sepsis is characterized as a systemic, excessive inflammatory response, which is frequently triggered by infection and proceeds unchecked by normal regulatory controls. Sepsis is most often associated with bacterial infections in humans. Severe trauma can also lead to systemic responses that adversely affect adaptive and innate immune responses, leading to excessive inflammation having pathological consequences. Severe trauma patients, such as burn and accident victims, may subsequently be afflicted with infections, some of which lead to sepsis. Clinical symptoms of sepsis in humans include lethargy, fever/hyperthermia in early stages of sepsis, confusion, and/or hypothermia in end-stage sepsis (e.g., septic shock).

Sepsis is a leading cause of hospitalization in the United States and is one of the most expensive conditions to treat because it typically requires a stay in the Intensive Care Unit (ICU) to achieve patient recovery. It has been estimated that 19 million patients will develop sepsis worldwide each year and this estimate likely substantially underestimates the problem. Indeed, sepsis is a leading cause of death, morbidity, and medical expense. Sepsis contributes to one-third of deaths of hospitalized patients. The mortality rate is estimated to be between 20% and 80%, depending on the cause of the sepsis and progression of sepsis. Onset of sepsis in patients following a hospital stay is frequent and particularly challenging, at least in part, because such patients are likely still in a state of recovery and therefore, physiologically weakened. Such patients may be in early, pre-clinical stages of sepsis upon release, but absent the present discoveries, sepsis cannot be detected at pre-clinical stages of the disease. Re-admittance to hospitals is a significant problem as it is costly and typically not covered in full by medical insurance policies. Indeed, people with sepsis are two to three times more likely to be readmitted to the hospital as people released from the hospital who were diagnosed with a variety of conditions, including heart failure, pneumonia, and chronic obstructive pulmonary disease. It is also noteworthy that a bout of sepsis can have lifelong ramifications for patients who are successfully treated and survive. As the number of sepsis survivors grows, it has become increasingly apparent that sepsis frequently leads to long-lasting physical and cognitive impairment.

Indeed, the growing number of patients who survive the acute phase of sepsis has revealed that the danger associated with the disease extends long after discharge from the hospital. Long-term mortality following a bout of sepsis is approximately 50% in the first year and rises to >81% over five years post-discharge. Sepsis survivors are also more prone to exhibit diminished physical and/or cognitive function following the bout of sepsis than age-matched controls hospitalized for unrelated indications. As a consequence of these diminished functions, many sepsis survivors are unable to return to the workforce.

The standard of care for treatment of bacterial sepsis in humans calls for aggressive use of antimicrobial therapy (e.g., antibiotics, anti-fungal agent, anti-viral agent), anti-parasitic agent therapy, and/or intravenous fluid therapy, which may be administered in conjunction with anti-inflammatory therapy. The choice of antibiotic used for treating a septic patient depends on the type of bacteria that infected the subject, which infection subsequently led to sepsis in the subject. Methods for culturing and identifying bacteria in samples isolated from a subject are known in the art. Broad-spectrum antibiotics are recommended within one hour after sepsis recognition/diagnosis. Beta-lactam antibiotics having broad coverage administered in combination with fluoroquinolones, macrolides, or aminoglycosides are recommended for severe cases of sepsis. An exemplary inflammatory therapy involves administration of non-steroidal anti-inflammatory agents to a human afflicted with bacterial sepsis.

Fungal infections are treated with anti-fungal medications specific to the particular fungus that caused the infection. These may be used in a cream or ointment, suppository, or pill form. *Candida* species are the predominant agent of fungal sepsis and account for about 5% of all cases of severe sepsis and septic shock in the United States. The antifungal armamentarium has expanded considerably with the advent of lipid formulations of amphotericin B, the newest triazoles and the echinocandins. Clinical trials have shown that the triazoles and echinocandins are efficacious and well tolerated antifungal therapies.

Prospective treatments for specific viruses implicated in sepsis are being developed. Pleconaril is an antiviral against enteroviral infection which inhibits viral attachment to the hosts cell receptors and prevents uncoating of the viral nucleic acids. Examples of ativiral agents that may be beneficial in presentations of sepsis in certain situations include acyclovir, which has been proven effective in HSV infections, amantadine, rimantadine, oseltamivir, and zanamivir for influenza, and more broad-spectrum antiviral drugs like ribavirin and favipiravir.

Parasite infections can lead to sepsis. For Giardia infections, a medication like metronidazole (Flagyl), tinidazole (Tindamax) or nitazoxanide (Alinia) may be used. For Chagas disease, antiparasitic medications such as benznidazole and nifurtimox may be used. For tapeworm, the most commonly used medications are praziquantel (Biltricide), albendazole (Albenza), and nitazoxanide (Alinia). However, if the infection has progressed and become more invasive, you may need treatment with anti-inflammatory medications, anti-seizure medications, a shunt to drain fluid from your brain, or surgery to remove cysts caused by the tapeworm. For roundworm, the most commonly used medications include medendazole (Vermox), albdendazole (Albenza) and ivermectin (Stromectol). Surgery could be required to remove the worm if there is a bowel obstruction.

The following guidelines provide the standard of care for sepsis patients as established by the American Medical Association:

Managing Infection:
Antibiotics: Administer broad-spectrum intravenous antimicrobials for all likely pathogens within 1 hour after sepsis recognition (strong recommendation; moderate quality of evidence [QOE]).

Source control: Obtain anatomic source control as rapidly as is practical (best practice statement [BPS]).

Antibiotic stewardship: Assess patients daily for de-escalation of antimicrobials; narrow therapy based on cultures and/or clinical improvement (BPS).

Managing resuscitation:

Fluids: For patients with sepsis-induced hypoperfusion, provide 30 mL/kg of intravenous crystalloid within 3 hours (strong recommendation; low QOE) with additional fluid based on frequent reassessment (BPS), preferentially using dynamic variables to assess fluid responsiveness (weak recommendation; low QOE).

Resuscitation targets: For patients with septic shock requiring vasopressors, target a mean arterial pressure (MAP) of 65 mm Hg (strong recommendation; moderate QOE).

Vasopressors: Use norepinephrine as a first-choice vasopressor (strong recommendation; moderate QOE).

Mechanical Ventilation in Patients with Sepsis-Related Acute Respiratory Distress Syndrome (ARDS):

Target a tidal volume of 6 mL/kg of predicted body weight (strong recommendation; high QOE) and a plateau pressure of ≤30 cm H$_2$O (strong recommendation; moderate QOE). See, for example, Howell and Davis (2017, JAMA 317:847).

As indicated hereinabove, sepsis is associated with multiple organ failure and high mortality. Commonly used markers for diagnosis of sepsis include: elevated leukocyte counts and elevated cytokine levels such as IL-6, IL-8 and IL-18, C-reactive protein, and procalcitonin. The latter two proteins are expressed at higher levels after trauma. With respect to procalcitonin, determination of procalcitonin levels is viewed as a helpful diagnostic marker, but is not viewed as a definitive marker of sepsis. Soluble urokinase-type plasminogen activator receptor (SuPAR) is considered to be a nonspecific marker of inflammation, but has prognostic value in the context of sepsis because higher SuPAR levels are associated with higher mortality in sepsis patients.

None of these markers provides a predictive indicator of sepsis, but rather collectively serve as indicators only upon onset of sepsis. Indeed, in advance of the present findings, a reliable method to predict risk for or diagnose sepsis in advance of the onset of clinical symptoms did not exist. As detailed herein, the methods, reagents, and kits described herein make it possible to diagnose patients with sepsis at pre-clinical stages and thus, make it possible to treat such patients in advance of the onset of clinical symptoms and at the least reduce the severity of acute sepsis in the patient should the patient progress toward disease despite early intervention.

Exemplary Target Patient Populations

Adult patients admitted to, for example, a hospital who are at high-risk for developing sepsis include the following:

Victims of trauma with either an Injury Severity Score of ≥15 or a Glasgow Coma Score of ≤8 on hospital presentation;

Any patient undergoing high-risk surgical procedures including any emergency surgery, high risk elective surgery procedures involving the thorax, esophagus, stomach, small bowel, large bowel; or Any patient being admitted to any intensive care unit (ICU) setting for any reason with no current evidence or suspicion of active infection as determined by primary team of attending medical practitioners.

Methods, reagents, and kits described herein relate to predicting and/or diagnosing sepsis in a human in advance of the appearance of symptoms of sepsis in the human. In accordance with the experimental findings presented herein, methods, reagents, and kits described are useful for diagnosing sepsis in a human subject in advance of symptomatic presentation. Indeed, results presented herein demonstrate that methods, reagents, and kits described herein can diagnose sepsis in a human subject at least three days in advance of clinical presentation. In light of results presented in the Examples, detection of over-representation or under-representation of at least one polynucleotide relative to an internal reference region in a body fluid sample (e.g., serum) isolated from a human subject, wherein the at least one polynucleotide comprises any one of SEQ ID NOs: 1-57 or 94-148, is a positive indicator that the human subject will develop sepsis symptoms. Accordingly, the methods, reagents, and kits described herein provide for diagnosis of sepsis at pre-clinical stages of the disease. Also encompassed herein are methods to assess over-representation or under-representation of at least one polynucleotide relative to an internal reference region, wherein the at least one polynucleotide comprises any one of SEQ ID NOs: 1-57 or 94-148, in body fluids and kits for such purposes.

In addition to plasma or serum, over-representation or under-representation of at least one polynucleotide (at least one of SEQ ID NOs: 1-57 or 94-148) relative to an internal reference region may be determined in other body fluids isolated from a human subject including: whole blood, a product derived from blood, or any fraction derived from blood (in addition to plasma or serum.

Any known method may be used for the determination of over-representation or under-representation of at least one polynucleotide (at least one of SEQ ID NOs: 1-57 or 94-148) relative to an internal reference region in body fluids. Methods encompassed for such determinations include: polymerase chain reaction (PCR) amplification with sequence specific primer pairs, a hybridization-based method, enzyme-linked immunosorbent assay (ELISA), radioimmunoassay (RIA), solid-phase enzyme immunoassay (EIA), mass spectrometry, microarray analysis, and any combination thereof. Such methods when used for determining risk for developing sepsis or predicting onset of sepsis are encompassed herein.

In a particular method for determining over-representation or under-representation of any one of SEQ ID NOs: 1-57 or 94-148 relative to an internal reference region in human body fluids, e.g. serum, the method calls for PCR amplification with sequence specific primer pairs. In an embodiment thereof, the PCR amplification is performed with at least one primer pair specific for any one of SEQ ID NOs: 1-57 or 94-148. Exemplary primer pairs for amplifying any one of SEQ ID NOs: 1-57 or 94-148 are presented in Table 1 or Table 3. Conditions for performing PCR amplifications are known in the art and presented in the Examples herein below. Such conditions may be determined based in part on the composition of a primer and/or primer pair and considerations relating to same are known in the art.

In another particular method for determining over-representation or under-representation of any one of SEQ ID NOs: 1-57 or 94-148 relative to an internal reference region in human body fluids, e.g. serum, the method calls for an ELISA. In one embodiment, the ELISA for at least one of SEQ ID NOs: 1-57 or 94-148 involves a sandwich array. In such an embodiment, PCR amplification of at least one of SEQ ID NOs: 1-57 or 94-148 may be performed as an initial step. Conventional microtiter plates may be coated with a first antibody, e.g. a guinea pig polyclonal antibody, directed against any one of SEQ ID NOs: 1-57 or 94-148. The plates are then blocked and the sample or reference is loaded. After incubation with, e.g., at least one of SEQ ID NOs: 1-57 or 94-148, a second antibody against any one of SEQ ID NOs: 1-57 or 94-148 is applied, e.g. a polyclonal rabbit antibody. A third antibody that detects the second antibody, e.g. an anti-rabbit antibody, conjugated to a suitable label, e.g. an enzyme for chromogenic detection, is then added. The plate is then developed with a substrate for the label in order to detect and quantify the label, which in turn serves as a measure of any one of SEQ ID NOs: 1-57 or 94-148 in the body fluid. This determination may then be compared to that of an internal reference region measured by similar methodology. If the label is an enzyme for chromogenic detection, the substrate is a color-generating substrate of the conjugated enzyme and the color reaction is subsequently detected in a microplate reader and compared to standards.

Suitable pairs of antibodies that may be used as first and second antibodies are any combination of, e.g., guinea pig, rat, mouse, rabbit, goat, chicken, donkey or horse antibodies. In a particular embodiment, the antibodies are polyclonal antibodies. In another particular embodiment, the antibodies are monoclonal antibodies or antibody fragments. Suitable labels include: chromogenic labels (enzymes that can be used to convert a substrate to a detectable colored or fluorescent compound), spectroscopic labels (e.g., fluorescent labels), and affinity labels which may be developed by an additional compound specific for the label, thereby facilitating detection and quantification, or any other label used in standard ELISA.

Other preferred methods for detection of any one of SEQ ID NOs: 1-57 or 94-148 include radioimmunoassay or competitive immunoassay using a single antibody and chemiluminescence detection on automated commercial analytical robots. Microparticle enhanced fluorescence, fluorescence polarized methodologies, or mass spectrometry may also be used. Detection devices, e.g. microarrays, are also useful components as readout systems for any one of SEQ ID NOs: 1-57 or 94-148.

Also encompassed herein are kits for assessing over-representation or under-representation of any one of SEQ ID NOs: 1-57 or 94-148 relative to an internal reference region for determining risk for developing sepsis, which kits may comprise apparatus and reagents for detecting at least one of SEQ ID NOs: 1-57 or 94-148. Apparatus and reagents considered for PCR amplification include: suitable PCR primer pairs specific for each of SEQ ID NOs: 1-57 or 94-148, amplification reagents, and thermocycling devices. With respect to ELISA, microtiter plates for ELISA, pre-coated ELISA plates, and plate covers are encompassed. Reagents useful for ELISA include those antibodies and solutions developed and designed for detecting each of SEQ ID NOs: 1-57 or 94-148. Standard solutions comprising each of SEQ ID NOs: 1-57 or 94-148 as positive controls may be included in such kits. Kits may further comprise hardware, such as pipettes, solutions such as buffers, blocking solutions and the like, filters, and directions for use thereof.

The following definitions are presented as an aid to understand the invention.

The term "DNA" means a polymer composed of deoxyriboucleotides.

The terms "sample", "biological sample", "diagnostic sample", and the like refer to a material known or suspected of containing one or more polynucleotide or polypeptide markers. The diagnostic sample may be any tissue ((e.g., blood, and fractions thereof, including serum, etc.).

The terms "polynucleotide" and "nucleic acid", used interchangeably herein, describe a polymer of any length, e.g., greater than about 10 bases, greater than about 100 bases, greater than about 500 bases, greater than 1000 bases, usually up to about 10,000 or more bases composed of nucleotides, such as deoxyribonucleotides or ribonucleotides, or compounds produced synthetically which can hybridize with naturally occurring nucleic acids in a sequence specific manner analogous to that of two naturally occurring nucleic acids in Watson-Crick base pairing interactions. Polynucleotide and nucleic acid include polynucleotides that encode a native-sequence polypeptide, a polypeptide variant, a portion of a polypeptide, a chimeric polypeptide, or an isoform, precursor, complex, modified form, or derivative of any of the foregoing, and any precursors thereof. Polynucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may be modified after synthesis (e.g., by conjugation with a label, such as a radioactive, chemiluminescent, chemiflourescent, or fluorescent label, and the like). Other types of modifications to polynucleotides known to a person skilled in the art include substitution of one or more naturally-occurring nucleotides with an analog, internucleotide modifications (e.g., uncharged linkages, charged linkages), and the like.

Polynucleotides can also include circulating nucleic acids ("CNA"). The term "circulating nucleic acid" or "CNA" refers to free nucleic acid, including RNA and DNA, circulating in any form in the blood. CNA can include gene transcripts, transcription factors or other polynucleotide sequences. CNA can be obtained from any applicable biological sample, including blood, plasma, serum, and the like.

"Variants" of the sequences described herein are sequences wherein at least one nucleotide differs from that of the native or wild-type sequence (or the complement thereof), by virtue of an insertion, deletion, modification and/or substitution of one or more nucleotides within the native sequence. Such variants generally have less than 100% sequence identity relative to a native sequence or its complement. Accordingly, a sequence variant may have a nucleotide sequence with at least about 70%, 75%, 80%, 85%, 90%, 95%, 96%, 97%, 98%, or 99% sequence identity relative to the native or wild-type sequence or complement thereof. Variants, furthermore, may include fragments of any length that retain a biological activity of the corresponding native sequence. Variants also include sequences wherein one or more nucleotides are added to the 5' or 3' end of, or within, a native sequence or its complement.

"Percent sequence identity" is defined herein as the percentage of nucleotides or amino acid residues in the candidate sequence that are identical to the nucleotides or residues in the sequence of interest after aligning the sequences and introducing gaps, if necessary, to achieve the maximum percent sequence identity, and not considering any conservative substitutions as part of the sequence identity. Methods and computer programs for the alignment of sequences are well known in the art, including, for example, "BLAST" algorithms.

"Oligonucleotides" include short, single-stranded polynucleotides that are at least seven nucleotides in length and less than about 250 nucleotides in length. The term "polynucleotides" includes oligonucleotides.

"Label" refers to a detectable compound or composition and "labelling" refers to the conjugation, fusion, or attachment of a detectable compound or composition to another. In some aspects described herein, the label is conjugated or fused directly or indirectly to a reagent, such as a polynucleotide probe or an antibody, and assists with the detection of the reagent to which it is conjugated or fused. The label itself can also be detectable (such as radioisotope labels or fluorescent labels and the like). In some aspects described herein, the label is an enzymatic label which catalyzes chemical alteration of a substrate compound or composition and results in a detectable product.

The term "diagnosis", as used herein, refers to the identification or classification of a molecular or pathological state, disease, or condition (e.g., sepsis). In a particular embodiment, sepsis is diagnosed in a subject (e.g., a human subject) in advance of onset of sepsis symptoms.

In a particular embodiment, a human subject is characterized as being "at risk for developing sepsis" because they have recently experienced an accident (e.g., vehicular, bicycle), physical trauma (e.g., due to burns resulting from exposure to, e.g., fire or chemicals; knife or gunshot wounds; blunt force trauma; explosion), surgery, and/or infection (e.g., a bacterial, fungal, or viral infection). Human subjects at risk for developing sepsis also include: subjects with weakened immune systems (e.g., immunocompromised subjects); subjects with pre-existing infections or medical conditions (e.g., type 2 diabetes, kidney disease, and asthma), obese subjects, and very young and very old subjects, and subjects injured in contaminated environments. Assays to evaluate risk for developing sepsis may also be implemented on all patients admitted to the hospital and/or released from the hospital as a matter of routine.

In a particular embodiment thereof, each patient released after a hospital stay comprising at least one overnight stay is assayed using methods described herein to evaluate whether the patient has early stage sepsis or is at risk for developing sepsis post-release. In that the expense involved in re-admittance to the hospital is substantial and insurance coverage is not commensurate with such expenses, screening all patients released after at least one overnight stay, would be a cost-effective way in which to provide better healthcare to the patient and minimize expenditures involved with same.

Further to the above, exemplary indications for use include:
At hospital admission where the best option today is to observe symptoms and run a series of blood cultures which normally takes over 24 hours for results and have high error rates;
On high risk patient groups in hospitals where early identification and treatment of sepsis could have an impact to a patient's survival;
On discharge where ruling out sepsis could lead to early discharge;
In long term care facilities where the frequency of sepsis is high and early diagnosis and appropriate monitoring and/or treatment thereafter could potentially reduce costly re-admissions and/or admissions to hospitals; and
Monitoring neonates for neonatal sepsis Sepsis-3 Definitions Sepsis is life-threatening organ dysfunction due to a dysregulated host response to infection Sepsis clinical criteria: organ dysfunction is defined as an increase of 2 points or more in the Sequential Organ Failure Assessment (SOFA) score
for patients with infections, an increase of 2 SOFA points gives an overall mortality rate of 10%
Patients with suspected infection who are likely to have a prolonged ICU stay or to die in the hospital can be promptly identified at the bedside with qSOFA ("HAT"); i.e. 2 or more of:
Hypotension: SBP less than or equal to 100 mmHg
Altered mental status (any GCS less than 15)
Tachypnoea: RR greater than or equal to 22.
Septic shock is a subset of sepsis in which underlying circulatory and cellular/metabolic abnormalities are profound enough to substantially increase mortality.
Septic shock clinical criteria: Sepsis and (despite adequate volume resuscitation) both of:
Persistent hypotension requiring vasopressors to maintain MAP greater than or equal to 65 mm Hg, and
Lactate greater than or equal to 2 mmol/i,
With these criteria, hospital mortality is in excess of 40%.

"Primer" refers to a polynucleotide capable of acting as a point of initiation of synthesis along a complementary strand when conditions are suitable for synthesis of a primer extension product. The synthesizing conditions include the presence of four different nucleotide bases (adenosine, cytidine, guanosine, thymidine/uridine) and at least one polymerization-inducing agent such as a reverse transcriptase or a DNA polymerase. The primers are present in a suitable buffer, which may include constituents which are co-factors or affect conditions such as pH and the like at various suitable temperatures. Primer includes single-stranded polynucleotide that is capable of hybridizing to nucleic acid and allowing the polymerization of a complementary nucleic acid, generally by providing a free 3'-OH group. Double stranded sequences can also be utilized. Primers are typically at least about 15 nucleotides. In some embodiments, primers can have a length of from about 15 to about 30, about 15 to about 50, about 15 to about 75, about 15 to about 100, or about 15 to about 500 nucleotides.

Exemplary primer pairs specific for each of SEQ ID NOs: 1-57 or 94-148 are presented herein in Table 1 or Table 3. Exemplary primer pairs specific for each of SEQ ID NOs: 58-93 are presented herein in Table 2. Such primer pairs are selected based on their specificity for a particular polynucleotide and may be optimized for use in connection with, e.g., PCR amplification. Polynucleotide-specific primer pairs may comprise primers that include variations within their sequence such that the primer is no longer 100% complementary to the polynucleotide for which it is specific. Primers comprising such variations are encompassed herein as long as the variations do not alter the ability of the primer to amplify the polynucleotide with specificity. Such variations may also include nucleotides and/or tags at the 5' and 3' ends of the primer that are not complementary the polynucleotide for which the primer is specific. It is also understood that a primer or primer pair may be complementary to sequences that flank any one of SEQ ID NOs: 1-148 in the human genome and thus, may be used to amplify one of SEQ ID NOs: 1-148 in keeping with methods described herein. Design of such primers and primer pairs is well within the capabilities of one of ordinary skill in the art having read the present specification.

In a particular embodiment, multiplex PCR based on the TaqMan approach is utilized to detect CNAs of interest. Such embodiments call for a primer pair, wherein each of the primers is specific for the particular CNA (polynucleotide)

of interest and one labeled probe which is specific for the particular CNA (polynucleotide) of interest and labeled at each terminus with a different moiety. In a particular embodiment, the different moiety can be a fluorophore at the first terminus and a quencher at the second terminus. Such fluorophore-quencher pairs comprise, for example, FAM-BHQ1, HEX-BHQ1, LC610-BHQ2, CY5-BHQ-2, and CY5.5-BBQ650. Other pairs useful for this embodiment are known in the art.

A "motif" or "sequence motif" refers to a nucleotide sequence pattern that is generally conserved across multiple species. Polynucleotides can be derived from the motif. The polynucleotides can correspond to the entire sequence of the motif or a portion or portions of the motif.

"Marker" or "biomarker" refers to an indicator which can be detected in a sample, and includes predictive, diagnostic, and prognostic indicators and the like. The marker can be an indicator of a particular disease or disorder (e.g., sepsis) having certain molecular, pathological, histological, and/or clinical features. Exemplary biomarkers include, without limitation, polynucleotides, polypeptides, polypeptide and polynucleotide modifications (such as post-translational modifications and the like), carbohydrates, and/or glycolipid-based molecular markers. The "presence", "amount", or "level" of a marker associated with an increased clinical benefit to an individual is a detectable level of the marker in a sample. The presence, amount, or level of a marker can be measured by methods known to a person skilled in the art. The presence, amount, or level of a marker may be measured prior to treatment, during treatment, after treatment, or a combination of any of the foregoing.

"Internal reference region" refers to a nucleic acid fragment circulating in a bodily fluid (e.g., blood or a fraction thereof such as serum) that is present in the same amount in both control subjects (those subjects who do not have sepsis, those subjects who are not at risk for developing sepsis, and/or those subjects who do not develop sepsis in three days) and subjects who have sepsis, as determined, for example, by RT-PCR experiments. Internal reference regions provide a nucleic acid fragment which is represented in the bodily fluid at a particular level, against which representation of other nucleic acid sequences (e.g., any one of SEQ ID NOs: 1-57 or 94-148), which differ in control subjects and sepsis patients and are therefore discriminatory, can be evaluated in a relative manner. An internal reference system can be at least one region but can also be a composition of a few regions.

"Over-representation" refers to a fold increase (relative quantity RQ) relative to the internal reference region calculated as at least $2^{-delta\text{-}delta\ Cq}$ of 2.

"Under-representation" refers to a fold decrease (relative quantity RQ) relative to the internal reference region calculated as at most $2^{-delta\text{-}delta\ Cq}$ of 0.5.

The ΔCq method normalizes disease-specific motifs within a sample by subtracting the Cq value of the internal reference region (reference motif) from the Cq value of the disease specific motifs.

The 2–ΔΔCq method calculates relative quantity (RQ) of normalized disease specific motifs between two sample types (i.e., healthy and diseased). Information from multiple reference motifs can be combined to improve accuracy.

In a PCR reaction, the Cq (Cycle Quantification) value is the PCR cycle number at which the sample's reaction curve intersects the threshold line. This value tells how many cycles it took for the PCR machine to detect a real signal from the sample. Therefore, lower Cq values indicate higher amounts of target nucleic acid fragments, whereas higher Cq values indicate lower amounts of target nucleic acid fragments.

Exemplary CNAs identified herein, which are markers of sepsis, include SEQ ID NOs: 1-57 and 94-148. See Tables 1 and 3 (FIGS. 1 and 3). Exemplary primer pairs for amplifying each of SEQ ID NOs: 1-57 and 94-148 are also presented in Tables 1 and 3 (FIGS. 1 and 3). Reference is made to the chromosomal locations to which each of these CNAs can be found in the human genome. Accordingly, longer polynucleotides comprising each of SEQ ID NOs: 1-57 and 94-148, respectively, can readily be determined via access to publicly available databases. Additional primers for amplifying each of SEQ ID NOs: 1-57 and 94-148, respectively, can be designed based on the availability of such additional sequence information.

Exemplary subsets of SEQ ID NOs: 1-57 and 94-148 comprise at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, or at least twenty-four of the polynucleotides. Exemplary subsets and primers for amplification of each of the markers offer reagents for detecting CNAs comprising the indicated SEQ ID NOs: See Tables 1-3. In a particular embodiment, detecting CNAs comprising the indicated SEQ ID NOs: is indicative of sepsis.

An exemplary subset may be provided in a kit for detecting at least one of SEQ ID NOs: 1-148 and subsets thereof (see, e.g., Table 4).

Table 4 presents an exemplary subset comprising, consisting essentially of, and/or consisting of the indicated SEQ ID NOs: 1-2, 4-6, 30-31, 38, 44, 46, 50, 53, 55, 59, 61, 68, 100, 108-110, 112, 114, 116, and 129. Primers for amplification of each of the markers listed in Table 4 can be found in the corresponding Tables 1, 2, or 3. Also encompassed herein are kits comprising the 24 exemplary markers presented in Table 4 and subsets thereof.

TABLE 4

List of 24 Exemplary Markers

| Listed in | Final motif ID | SEQ ID NO: | Patent ID |
|---|---|---|---|
| Table 1 | Sepsis JC1 | 1 | hu-sep-CNAD-0001 |
| Table 1 | Sepsis JC2 | 2 | hu-sep-CNAD-0002 |
| Table 1 | Sepsis JC4 | 4 | hu-sep-CNAD-0004 |
| Table 1 | Sepsis JC5 | 5 | hu-sep-CNAD-0005 |
| Table 1 | Sepsis JC6 | 6 | hu-sep-CNAD-0006 |
| Table 1 | Sepsis JC34 | 30 | hu-sep-CNAD-0030 |
| Table 1 | Sepsis JC35 | 31 | hu-sep-CNAD-0031 |
| Table 1 | Sepsis JC42 | 38 | hu-sep-CNAD-0038 |
| Table 1 | Sepsis JC48 | 44 | hu-sep-CNAD-0044 |
| Table 1 | Sepsis JC50 | 46 | hu-sep-CNAD-0046 |
| Table 1 | Sepsis SC2 | 50 | hu-sep-CNAD-0050 |
| Table 1 | Sepsis SC5 | 53 | hu-sep-CNAD-0053 |
| Table 1 | Sepsis SC7 | 55 | hu-sep-CNAD-0055 |
| Table 2 | Sepsis JU2 | 59 | hu-sep-CNAD-0059 |
| Table 2 | Sepsis JU4 | 61 | hu-sep-CNAD-0061 |
| Table 2 | Sepsis JU11 | 68 | hu-sep-CNAD-0068 |
| Table 3 | Sepsis J7 | 100 | hu-sep-CNAD-0100 |
| Table 3 | Sepsis J15 | 108 | hu-sep-CNAD-0108 |
| Table 3 | Sepsis J16 | 109 | hu-sep-CNAD-0109 |
| Table 3 | Sepsis J17 | 110 | hu-sep-CNAD-0110 |
| Table 3 | Sepsis J19 | 112 | hu-sep-CNAD-0112 |
| Table 3 | Sepsis J21 | 114 | hu-sep-CNAD-0114 |
| Table 3 | Sepsis J23 | 116 | hu-sep-CNAD-0116 |
| Table 3 | Sepsis J36 | 129 | hu-sep-CNAD-0129 |

Exemplary CNAs identified herein, which are internal reference regions, include SEQ ID NOs: 58-93. See Table 2 (FIG. 2). Exemplary primer pairs for amplifying each of SEQ ID NOs: 58-93 are also presented in Tables 1-3 (FIG. 1-3). Reference is made to the chromosomal locations to which each of these CNAs can be found in the human genome. Accordingly, larger polynucleotides comprising each of SEQ ID NOs: 58-93, respectively, can readily be determined via access to publicly available databases. Additional primers for amplifying each of SEQ ID NOs: 58-93, respectively, can be designed based on the availability of such additional sequence information.

Candidate internal reference regions (Table 2: SEQ ID NOs: 58-93) were evaluated to identify the ones that were most consistently represented across a set of sepsis and control samples. Given a candidate reference region, the differences in median Cq values of the regions between sepsis samples and control samples were calculated. The lesser the difference in the median Cq values, the higher the consistency of the region across sepsis and non-sepsis conditions, and therefore the more suitable the region as an internal reference region.

The three most consistent regions were selected as exemplary internal reference regions (SEQ ID NOs: 59, 61 and 68). Their sequences and primers used for amplification are listed in Table 2 in the corresponding rows of the regions.

An exemplary subset of SEQ ID NOs: set forth in Table 4 comprises SEQ ID NOs: 1, 6, 46, 50, 53, 55, 100, 109, 110, 114, and at least one of SEQ ID NOs: 59, 61, or 68. Primers for amplifying SEQ ID NOs: 1, 6, 46, 50, 53, 55, 59, 61, 68, 100, 109, 110, and 114 are presented in Tables 1-3.

An exemplary subset of SEQ ID NOs: set forth in Table 4 comprises SEQ ID NOs: 1, 2, 6, 30, 53, 55, 110, 112, 114, 116, and at least one of SEQ ID NOs: 59, 61, or 68. Primers for amplifying SEQ ID NOs: 1, 2, 6, 30, 53, 55, 59, 61, 68, 110, 112, 114, and 116 are presented in Tables 1-3.

An exemplary subset of SEQ ID NOs: set forth in Table 4 comprises SEQ ID NOs: 30, 31, 38, 44, 46, 50, 53, 55, 100, 129, and at least one of SEQ ID NOs: 59, 61, or 68. Primers for amplifying SEQ ID NOs: 30, 31, 38, 44, 46, 50, 53, 55, 59, 61, 68, 100, and 129 are presented in Tables 1-3.

An exemplary subset of SEQ ID NOs: set forth in Table 4 comprises SEQ ID NOs: 4, 5, 30, 31, 100, 108, 109, 110, 116, 129, and at least one of SEQ ID NOs: 59, 61, or 68. Primers for amplifying SEQ ID NOs: 4, 5, 30, 31, 59, 61, 68, 100, 108, 109, 110, 116, and 129 are presented in Tables 1-3.

An exemplary subset of SEQ ID NOs: set forth in Table 4 comprises SEQ ID NOs: 53, 55, 100, 108, 109, 110, 112, 114, 116, 129, and at least one of SEQ ID NOs: 59, 61, or 68. Primers for amplifying SEQ ID NOs: 53, 55, 59, 61, 68, 100, 108, 109, 110, 112, 114, 116, and 129 are presented in Tables 1-3.

An exemplary subset of SEQ ID NOs: set forth in Table 4 comprises SEQ ID NOs: 30, 31, 46, 55, 108, 110, 112, 114, 116, 129, and at least one of SEQ ID NOs: 59, 61, or 68. Primers for amplifying SEQ ID NOs: 30, 31, 46, 55, 59, 61, 68, 108, 110, 112, 114, 116, and 129 are presented in Tables 1-3.

An exemplary subset of SEQ ID NOs: set forth in Table 4 comprises SEQ ID NOs: 1, 2, 5, 46, 53, 100, 112, 114, 116, 129, and at least one of SEQ ID NOs: 59, 61, or 68. Primers for amplifying SEQ ID NOs: 1, 2, 5, 46, 53, 59, 61, 68, 100, 112, 114, 116, and 129 are presented in Tables 1-3.

An exemplary subset of SEQ ID NOs: set forth in Table 4 comprises SEQ ID NOs: 2, 4, 6, 31, 44, 100, 109, 110, 116, 129 and at least one of SEQ ID NOs: 59, 61, or 68. Primers for amplifying SEQ ID NOs: 2, 4, 6, 31, 44, 59, 61, 68, 100, 109, 110, 116, and 129 are presented in Tables 1-3.

An exemplary subset of SEQ ID NOs: set forth in Table 4 comprises SEQ ID NOs: 5, 6, 30, 31, 44, 50, 55, 100, 110, 112, and at least one of SEQ ID NOs: 59, 61, or 68. Primers for amplifying SEQ ID NOs: 5, 6, 30, 31, 44, 50, 55, 59, 61, 68, 100, 110, and 112 are presented in Tables 1-3.

An exemplary subset of SEQ ID NOs: set forth in Table 4 comprises SEQ ID NOs: 2, 31, 38, 44, 46, 55, 109, 110, 112, 129, and at least one of SEQ ID NOs: 59, 61, or 68. Primers for amplifying SEQ ID NOs: 2, 31, 38, 44, 46, 55, 59, 61, 68, 109, 110, 112, and 129 are presented in Tables 1-3.

An exemplary subset of SEQ ID NOs: set forth in Table 4 comprises SEQ ID NOs: 4, 5, 6, 30, 38, 44, 53, 55, 108, 109, and at least one of SEQ ID NOs: 59, 61, or 68. Primers for amplifying SEQ ID NOs: 4, 5, 6, 30, 38, 44, 53, 55, 59, 61, 68, 108, and 109 are presented in Tables 1-3.

An exemplary subset of SEQ ID NOs: set forth in Table 4 comprises SEQ ID NOs: 31, 46, 55, 108, 114, and at least one of SEQ ID NOs: 59, 61, or 68. Primers for amplifying SEQ ID NOs: 31, 46, 55, 59, 61, 68, 108, and 114 are presented in Tables 1-3.

An exemplary subset of SEQ ID NOs: set forth in Table 4 comprises SEQ ID NOs: 100, 109, 112, 114, 116, and at least one of SEQ ID NOs: 59, 61, or 68. Primers for amplifying SEQ ID NOs: 59, 61, 68, 100, 109, 112, 114, and 116 are presented in Tables 1-3.

An exemplary subset of SEQ ID NOs: set forth in Table 4 comprises SEQ ID NOs: 31, 38, 44, 100, 108, and at least one of SEQ ID NOs: 59, 61, or 68. Primers for amplifying SEQ ID NOs: 31, 38, 44, 59, 61, 68, 100, and 108 are presented in Tables 1-3.

An exemplary subset of SEQ ID NOs: set forth in Table 4 comprises SEQ ID NOs: 1, 4, 5, 110, 112, and at least one of SEQ ID NOs: 59, 61, or 68. Primers for amplifying SEQ ID NOs: 1, 4, 5, 59, 61, 68, 110, and 112 are presented in Tables 1-3.

An exemplary subset of SEQ ID NOs: set forth in Table 4 comprises SEQ ID NOs: 5, 6, 44, 55, 109, and at least one of SEQ ID NOs: 59, 61, or 68. Primers for amplifying SEQ ID NOs: 5, 6, 44, 55, 59, 61, 68, and 109 are presented in Tables 1-3.

An exemplary subset of SEQ ID NOs: set forth in Table 4 comprises SEQ ID NOs: 1, 2, 5, 50, 53, and at least one of SEQ ID NOs: 59, 61, or 68. Primers for amplifying SEQ ID NOs: 1, 2, 5, 50, 53, 59, 61, and 68 are presented in Tables 1-3.

An exemplary subset of SEQ ID NOs: set forth in Table 4 comprises SEQ ID NOs: 4, 5, 6, 31, 38, and at least one of SEQ ID NOs: 59, 61, or 68. Primers for amplifying SEQ ID NOs: 4, 5, 6, 31, 38, 59, 61, and 68 are presented in Tables 1-3.

An exemplary subset of SEQ ID NOs: set forth in Table 4 comprises SEQ ID NOs: 1, 53, 100, 114, 116, and at least one of SEQ ID NOs: 59, 61, or 68. Primers for amplifying SEQ ID NOs: 1, 53, 59, 61, 68, 100, 114 and 116 are presented in Tables 1-3.

An exemplary subset of SEQ ID NOs: set forth in Table 4 comprises SEQ ID NOs: 5, 6, 30, 31, 38, and at least one of SEQ ID NOs: 59, 61, or 68. Primers for amplifying SEQ ID NOs: 5, 6, 30, 31, 38, 59, 61 and 68 are presented in Tables 1-3.

An exemplary subset of SEQ ID NOs: set forth in Table 4 comprises SEQ ID NOs: 44, 46, 50, 53, 55, and at least one of SEQ ID NOs: 59, 61, or 68. Primers for amplifying SEQ ID NOs: 44, 46, 50, 53, 55, 59, 61, and 68 are presented in Tables 1-3.

An exemplary subset of SEQ ID NOs: set forth in Table 4 comprises SEQ ID NOs: 109, 110, 112, 114, 116, and at least one of SEQ ID NOs: 59, 61, or 68. Primers for amplifying SEQ ID NOs: 59, 61, 68, 109, 110, 112, 114, and 116 are presented in Tables 1-3.

An exemplary subset of SEQ ID NOs: set forth in Table 4 comprises SEQ ID NOs: 4, 5, 114, 116, 119 and at least one of SEQ ID NOs: 59, 61, or 68. Primers for amplifying SEQ ID NOs: 4, 5, 59, 61, 68, 114, 116, and 119 are presented in Tables 1-3.

An exemplary subset of SEQ ID NOs: set forth in Table 4 comprises SEQ ID NOs: 4, 6, 30, 100, 108 and at least one of SEQ ID NOs: 59, 61, or 68. Primers for amplifying SEQ ID NOs: 4, 6, 30, 59, 61, 68, 100, and 108 are presented in Tables 1-3.

An exemplary subset of SEQ ID NOs: set forth in Table 4 comprises SEQ ID NOs: 38, 44, 109, 110, 112 and at least one of SEQ ID NOs: 59, 61, or 68. Primers for amplifying SEQ ID NOs: 38, 44, 59, 61, 68, 109, 110, and 112 are presented in Tables 1-3.

An exemplary subset of SEQ ID NOs: set forth in Table 4 comprises SEQ ID NOs: 1, 2, 4, 5, and at least one of SEQ ID NOs: 59, 61, or 68. Primers for amplifying SEQ ID NOs: 1, 2, 4, 5, 59, 61, and 68 are presented in Tables 1-3.

An exemplary subset of SEQ ID NOs: set forth in Table 4 comprises SEQ ID NOs: 30, 53, 108, 109, and at least one of SEQ ID NOs: 59, 61, or 68. Primers for amplifying SEQ ID NOs: 30, 53, 59, 61, 68, 108, and 109 are presented in Tables 1-3.

An exemplary subset of SEQ ID NOs: set forth in Table 4 comprises SEQ ID NOs: 2, 109, 110, 116, and at least one of SEQ ID NOs: 59, 61, or 68. Primers for amplifying SEQ ID NOs: 2, 59, 61, 68, 109, 110, and 116 are presented in Tables 1-3.

An exemplary subset of SEQ ID NOs: set forth in Table 4 comprises SEQ ID NOs: 5, 6, 50, 53, and at least one of SEQ ID NOs: 59, 61, or 68. Primers for amplifying SEQ ID NOs: 5, 6, 50, 53, 59, 61, and 68 are presented in Tables 1-3.

An exemplary subset of SEQ ID NOs: set forth in Table 4 comprises SEQ ID NOs: 1, 31, 55, 108, and at least one of SEQ ID NOs: 59, 61, or 68. Primers for amplifying SEQ ID NOs: 1, 31, 55, 59, 61, 68, and 108 are presented in Tables 1-3.

An exemplary subset of SEQ ID NOs: set forth in Table 4 comprises SEQ ID NOs: 30, 38, 55, 100, and at least one of SEQ ID NOs: 59, 61, or 68. Primers for amplifying SEQ ID NOs: 30, 38, 55, 59, 61, 68, and 100 are presented in Tables 1-3.

An exemplary subset of SEQ ID NOs: set forth in Table 4 comprises SEQ ID NOs: 2, 4, 112, 114, and at least one of SEQ ID NOs: 59, 61, or 68. Primers for amplifying SEQ ID NOs: 2, 4, 59, 61, 68, 112, and 114 are presented in Tables 1-3.

An exemplary subset of SEQ ID NOs: set forth in Table 4 comprises SEQ ID NOs: 31, 110, 112, 114, and at least one of SEQ ID NOs: 59, 61, or 68. Primers for amplifying SEQ ID NOs: 31, 59, 61, 68, 110, 112, and 114 are presented in Tables 1-3.

An exemplary subset of SEQ ID NOs: set forth in Table 4 comprises SEQ ID NOs: 5, 31, 116, 129, and at least one of SEQ ID NOs: 59, 61, or 68. Primers for amplifying SEQ ID NOs: 5, 31, 59, 61, 68, 116, and 129 are presented in Tables 1-3.

An exemplary subset of SEQ ID NOs: set forth in Table 4 comprises SEQ ID NOs: 2, 4, 5, 6, and at least one of SEQ ID NOs: 59, 61, or 68. Primers for amplifying SEQ ID NOs: 2, 4, 5, 6, 59, 61, and 68 are presented in Tables 1-3.

Machine learning classification systems, such as, e.g., a support vector or neural network are utilized herein. The system utilized herein creates a multidimensional 'map' comprising basically all the markers (both sepsis and non-sepsis) and then when a sample is tested, it's position on the map it marked. After this, the system looks at the closest points and if they are sepsis, it will call the sample 'sepsis'. If the closest points are not sepsis, it will call the sample 'not sepsis'. In a particular embodiment, the system looks for a certain small number of neighboring samples (not the single closest one) in this virtual multidimensional space, where each sample is represented by a group of marker values on the sample. The assignment of the sample to sepsis/non-sepsis is accomplished by a majority vote of the known labels of the closest neighbors (e.g., 5 of them). If there are more sepsis samples in the neighborhood, the incoming sample is assigned to "sepsis". If there are more non-sepsis samples in the neighborhood, the new sample is assigned to "non-sepsis".

"Encode" refers to a polynucleotide "encoding" a polypeptide if, in its native state or when manipulated by methods well known to those skilled in the art, it can be transcribed and/or translated to produce the mRNA for the polypeptide and/or the polypeptide (or a fragment thereof). The anti-sense strand is the complement of such a nucleic acid, and the encoding sequence can be deduced therefrom.

"Array" or "microarray" refers to an ordered arrangement of hybridizable array elements on a substrate, such as a solid substrate (e.g., glass slide and the like) or a semi-solid substrate (e.g., nitrocellulose membrane and the like). In some embodiments, the array elements may be polynucleotide probes (e.g. oligonucleotide). Arrays may include DNA microarrays (including cDNA microarrays, oligonucleotide microarrays, SNP microarrays, etc.), protein microarrays, peptide microarrays, antibody microarrays, and the like.

"Amplification" or "amplifying" refers to the production of one or more copies of a reference nucleic acid sequence or its complement. Amplification may be linear or exponential (e.g., in a polymerase chain reaction (PCR)). A nucleic acid copy produced from amplification may not have perfect sequence complementarity or identity relative to the reference sequence. In some embodiments, the copies can include nucleotide analogs, including deoxyinosine, intentional sequence alterations (such as alterations introduced through a primer that is hybridizable, but not fully complementary, to the template), and/or sequence errors that occur during the amplification process.

The terms "expression" and "expression level", in general, are used interchangeably and generally refer to the amount of a marker in a sample. "Expression" generally refers to the process by which information (e.g., gene-encoded and/or epigenetic) is converted into the structures present and operating in the cell. Therefore, as used herein, "expression" can refer to transcription into a polynucleotide (such as mRNA and the like), translation into a polypeptide, or even polynucleotide and/or polypeptide modifications (e.g., post-translational modification of a polypeptide and the like). Fragments of the transcribed polynucleotide, the translated polypeptide, or polynucleotide and/or polypeptide modifications (such as post-translational modification of a polypeptide and the like) will also be regarded as expressed whether they originate from a transcript generated by alternative splicing or a degraded transcript, or from a post-translational processing of the polypeptide (e.g., by proteolysis). "Expressed genes" include those that are transcribed into a polynucleotide as mRNA and then translated into a polypeptide, and also those that are transcribed into RNA but not translated into a polypeptide (such as transfer and ribosomal RNAs and the like).

An "isolated" nucleic acid refers to a nucleic acid molecule that has been separated from a component of its natural environment. An isolated nucleic acid includes a nucleic acid molecule contained in cells that ordinarily contain the nucleic acid molecule. The nucleic acid molecule may be present extrachromosomally or at a chromosomal location that is different from its natural location.

The term "sequencing" and its variants include obtaining sequence information from a strand of a nucleic acid molecule, typically by determining the identity of at least some nucleotides (including their nucleic acid components) within the nucleic acid molecule. The term sequencing may also refer to determining the order of nucleotides (base sequences) in a nucleic acid sample (e.g. DNA or RNA). Many techniques are available and known to a person skilled in the art, such as Sanger sequencing, high-throughput sequencing technologies (such as the GS FLX platform formerly offered by Roche Applied Science, Penzberg, Germany, based on pyro sequencing, or Illumina sequencing platforms, as offered by Illumina Inc., 5200 Illumina Way, San Diego, Calif. 92122, USA), and the like. High-throughput sequencing technologies refer to sequencing technologies having increased throughput as compared to traditional Sanger- and capillary-electrophoresis-based approaches (e.g., with the ability to generate hundreds of thousands or millions of relatively small sequence reads at a time). High throughput sequencing technologies include, but are not limited to, sequencing by synthesis, sequencing by ligation, pyrosequencing, sequencing by hybridization, and/or the like.

As used herein, "reactive" means the agent has affinity for, binds to, or is directed against a specific CNA. As further used herein, an "agent" includes a protein, polypeptide, peptide, nucleic acid (including DNA or RNA), antibody, Fab fragment, F(ab')2 fragment, molecule, compound, antibiotic, drug, and any combinations thereof. A Fab fragment is a univalent antigen-binding fragment of an antibody, which is produced by papain digestion. A F(ab')2 fragment is a divalent antigen-binding fragment of an antibody, which is produced by pepsin digestion. By way of example, the agent of the present invention can be labeled with a detectable marker. Agents that are reactive with CNAs can be identified by contacting the CNA with an agent of interest and assessing the ability of the agent to bind to the CNA.

In one embodiment of the present invention, the agent reactive with a sepsis biomarker is an antibody. Antibodies for use herein can be labeled with a detectable marker. Labeling of an antibody can be accomplished using one of a variety of labeling techniques, including peroxidase, chemiluminescent labels known in the art, and radioactive labels known in the art. The detectable marker of the present invention can be, for example, a nonradioactive or fluorescent marker, such as biotin, fluorescein (FITC), acridine, cholesterol, or carboxy-X-rhodamine (ROX), which can be detected using fluorescence and other imaging techniques readily known in the art. Alternatively, the detectable marker can be a radioactive marker, including, for example, a radioisotope. The radioisotope can be any isotope that emits detectable radiation, such as $^{35}S$, $^{32}P$, or $^{3}H$. Radioactivity emitted by the radioisotope can be detected by techniques well known in the art. For example, gamma emission from the radioisotope can be detected using gamma imaging techniques, particularly scintigraphic imaging. By way of example, the agent of the present invention is a high-affinity antibody labeled with a detectable marker.

Where the agent of the present invention is an antibody reactive with a sepsis biomarker, a biological sample taken from a mammal (e.g., a human) can be purified by passage through an affinity column which contains the antibody having affinity to the sepsis biomarker as a ligand attached to a solid support, such as an insoluble organic polymer in the form of a bead, gel, or plate. The antibody attached to the solid support can be used in the form of a column. Examples of suitable solid supports include, without limitation, agarose, cellulose, dextran, polyacrylamide, polystyrene, sepharose, and other insoluble organic polymers. The antibody can be further attached to the solid support through a spacer molecule, if desired. Appropriate binding conditions (e.g., temperature, pH, and salt concentration) can be readily determined by the skilled artisan. By way of example, the antibody can be attached to a sepharose column, such as Sepharose 4B.

Alternatively, a biological sample from a mammal (e.g., a human) can be assayed using hybridization analysis of nucleic acid extracted from the biological sample taken from the mammal (e.g., a human) to determine the presence of a sepsis biomarker, such as a CNA. This method also can be conducted by performing a Southern blot analysis of DNA using at least one nucleic acid probe which hybridizes to CNAs (including amplified CNAs). The nucleic acid probes described herein can be prepared by a variety of techniques known to those skilled in the art, including, without limitation, the following: restriction enzyme digestion of nucleic acid; and automated synthesis of oligonucleotides having sequences which correspond to selected portions of the nucleotide sequence of the sepsis biomarker, using commercially-available oligonucleotide synthesizers.

The nucleic acid probes used herein can be DNA or RNA, and can vary in length from about 5-20 nucleotides or 10-20 nucleotides to the entire length of the nucleic acid encoding for a sepsis biomarker. In some embodiments, the nucleic acid probes are oligonucleotides. The nucleic acid used in the probes can be derived from mammalian polynucleotide sequence complementary to the sepsis biomarker. In addition, the nucleic acid probes of the present invention can be labeled with one or more detectable markers. Labeling of the nucleic acid probes can be accomplished using one of a number of methods known in the art (e.g., nick translation, end labeling, fill-in end labeling, polynucleotide kinase exchange reaction, random priming, SP6 polymerase (for riboprobe preparation)) along with one of a variety of labels (e.g., radioactive labels, such as $^{35}S$, $^{32}P$, or $^{3}H$, or nonradioactive labels, such as biotin, fluorescein (FITC), acridine, cholesterol, or carboxy-X-rhodamine (ROX)). In some embodiments, these nucleic acid probes are used in an array or microarray.

In addition, the present invention provides a method of determining whether a human has sepsis, but is asymptomatic, or has already developed sepsis and has symptoms thereof. The method includes analyzing a biological sample of the human for the presence of at least one sepsis biomarker, and optionally, further recommending a corroborative test for sepsis if the at least one sepsis biomarker is present in the biological sample. In some embodiments, the corroborative test includes ELISA, immunohistochemistry, and Western Blot/immunoblot or a combination of more than one of any of the foregoing.

In the methods described herein, the step of analyzing a biological sample may optionally include obtaining the sample from the human; isolating nucleic acid from the sample; amplifying the isolated nucleic acid using primers that are specific for or capable of amplifying a sequence corresponding to a sepsis CNA biomarker; and sequencing the amplified nucleic acid. In some embodiments, the isolated nucleic acid includes genomic DNA, mRNA, and/or cDNA obtained from mRNA. In some embodiments, the step of determining representation of the at least one sepsis CNA marker includes use of at least one of a PCR-based detection method and a hybridization-based method. In some embodiments, the step of determining representation of the at least sepsis CNA marker includes an immunohistochemical analysis. In some embodiments, an array or a microarray is used for identifying the sepsis biomarker.

The biological sample can be assayed for expression of sepsis biomarkers in vitro or in vivo. In addition, the biological sample can be assayed for expression of sepsis biomarkers using all of the various assays and methods of detection and quantification described above.

The discovery that certain CNAs constitute sepsis biomarkers provides compositions and methods for identifying a human having early stage sepsis (e.g., pre-symptomatic sepsis), and presents the potential for commercial application in the form of a test for the diagnosis of sepsis and kits including same. The development of such a test or kit would provide general screening procedures; these procedures could assist in the early detection and diagnosis of sepsis in human subjects. Accordingly, the present invention further provides a kit for use as an assay of sepsis, comprising at least one agent reactive with a sepsis biomarker. The agent can be any of those described above, and can be used in any of the above-described assays or methods for detecting sepsis biomarkers.

Oligonucleotides complementary to a sepsis CNA biomarker can be designed based on the nucleotide sequence of the particular CNA sepsis biomarker. A nucleotide sequence complementary to the selected partial sequence of the sepsis CNA biomarker can, e.g., be chemically synthesized using one of a variety of techniques known to those skilled in the art, including, without limitation, automated synthesis of oligonucleotides having sequences which correspond to a partial sequence of the sepsis CNA biomarker nucleotide sequence, or a variation sequence thereof, using commercially-available oligonucleotide synthesizers.

The present invention also provides the use of an oligonucleotide capable of identifying at least one sepsis CNA biomarker to determine the representation of same in a human. The oligonucleotide can be labelled with a detectable marker, such as a radioactive marker, fluorescent marker, the like, or a combination of any of the foregoing.

Serum from healthy individuals (controls) and diseased patients (i.e. sepsis patients) was harvested and initially stored at −80 degrees Celsius. Total DNA was extracted from the serum samples using the High Pure Viral Nucleic Acid Kit (Roche Applied Science; Cat. No. 11858874001). The DNA was amplified using the GenomePlex Single Cell Whole Genome Amplification Kit (Sigma; Cat. No. WGA4-500RXN) and purified using the GenElute™ PCR Clean-Up Kit (Sigma, Cat. No. NA1020-1KT). High-throughput paired-end DNA sequencing was performed by SEQ-IT Kaiserslautern Sequencing facility on NextSeq 500 sequencer and SEQ-IT machines. The resulting sequence reads were mapped to the human genome. Using an in-house Bioinformatics pipeline, which was established on the high-performance Bioinformatics infrastructure at the Institute of Computational Biotechnology at the Technical Univeristy of Graz, Austria, the present inventors have identified DNA motifs, which were present at different read count numbers in diseased humans, when compared to controls. The motifs identified are the result of the host response (i.e., the response of the human body to sepsis). The DNA motifs identified were used as targets for the development of a real-time Polymerase-Chain Reaction (RT-PCR) assay. In addition to the motifs, which are present at different levels in healthy controls and sepsis patients (markers; SEQ ID NOs: 1-57 or 94-148), motifs which were present at the same level in healthy and diseased humans were also identified to allow the normalization of the results (SEQ ID NOs: 58-93). The RT-PCR-evaluated motifs, which could be used to discriminate in a statistically significant manner between healthy controls and sepsis patients, stand-alone, or in combination with each other, are the subject basis for assays described herein.

In a particular embodiment, the Illumina sequences were analyzed using a genome assembly/mapping bioinformatics processing method. The cleaned sequence reads were mapped to the human genome using a fast mapper, genomic hotspots for sepsis were identified, the reads were comprehensively mapped to the identified hotspots, and a gene search was conducted in the hotspot region to correlate the reads with a gene. Reads that did not map to the genome were assembled to generate clusters and then analyzed using the same procedures used for the hotspots.

In an embodiment of an Illumina sequence analysis method, CNA libraries are obtained from a blood sample collection and these libraries are sequenced in an Illumina sequencing operation. After the sequencing operation, the method proceeds to an operation step, where the processing unit stores the output of the Illumina sequencing in a text-based file format, for example, a FASTQ format. It is understood that the output of the Illumina sequencing can also be stored in other file formats, such as, for example, SAM or BAM formats. The sequencing files are assembled with a reference genome to determine genome locations with significant counts of exclusively at risk or normal (not at risk) reads.

The results of the alignment are then processed. In some embodiments, the results of the alignment process are outputted in a text-based file format, such as a SAM format. A SAM formatted file is a tab-delimited text file that contains sequence alignment data. In such embodiments, the processing unit converts the SAM format to a BAM format, which is a binary version of the SAM formatted file. In other examples, the alignment process outputs a BAM formatted file, and thus, the conversion step is skipped. Preparation for and creation of an index file associated with the BAM formatted file is then created. The index file creation process may include categorizing by adding sample names as read groups, sorting, and/or merging.

The created index file and the BAM formatted file is further processed by a processing unit. In particular, processing includes reviewing the alignments and extracting the alignments, which have sufficient coverage for each contiguous sequence (=contig) of the reference genome. In an embodiment, the alignment parameters comprise a bucket size of 25 and a minimum coverage of 5, although it is understood that the bucket size and minimum coverage value may differ in alternate embodiments. Control regions and at risk regions having 50% or more proportion are extracted and compared to determine overlaps. In some embodiments, these regions are stored in a database associated with the processing unit for later retrieval and/or review. Next, the extracted control regions are subtracted from the at risk regions so that only the at risk regions remain, thereby providing sequence reads that are present in only at risk regions. In an embodiment, the control filtering parameters comprise a minimum subjects value of 3 and a minimum proportion value of 0.5, although it is understood that these values may differ in alternate embodiments.

In some embodiments, not all of the sequences are aligned. In such examples, the unaligned sequences are collected and may be stored in the database for later retrieval and/or review. In an embodiment, the unaligned sequences are aligned against other references, such as viral references, to determine if any alignments exist. If alignments exist, the sequences may be stored in the database for later retrieval and alignment with new viruses, as desired.

In an embodiment, analysis of Illumina sequencing reads can be achieved using a TimeLogic® Decypher® biocomputing platform (Active Motif, Carlsbad, Calif.) and multiple CPU servers at the sequencing center.

Sequence variability of the identified CNA motifs specific to sepsis risk was then analyzed in a sampling of different humans through PCR and Sanger sequencing of the PCR products to determine if the identified CNA motifs are capable of detecting sepsis risk generally. In healthy humans, it has been shown that approximately 97% of CNA sequences are of genomic origin [Beck et al., 2009, *Clin Chem.*, 55(4):730-8].

Arrays comprising one of more polynucleotides of the disclosure, PCR primers and/or probes for amplifying and/or detecting polynucleotides (CNAs) described herein, and methods for detecting risk for developing sepsis comprising an array or PCR primers and/or probes are encompassed herein.

One of more polynucleotide sequences of the disclosure can be incorporated onto a sequence array, such as a biochip, DNA chip, BiofireDX filmarray and other filmarrays, microarray, macroarray, and the like, for screening, e.g., serum separated from whole blood from humans for sepsis risk. Alternatively, CNAs can be extracted from the sample for screening on the array. Arrays are generally solid supports upon which a collection of polynucleotides and/or primers and/or probes are placed at defined locations on the array, either by spotting, printing, or direct synthesis. The array can include probes corresponding to one or more of the polynucleotides described herein (e.g., at least one of SEQ ID NOs: 1-57 or 94-148 and/or primers and/or probes for amplifying and/or detecting one or more polynucleotides of SEQ ID NOs: 1-57 or 94-148 and at least one of SEQ ID NOs: 59, 61, or 68 and/or primers and/or probes for amplifying and/or detecting one or more polynucleotides of SEQ ID NOs: 59, 61, or 68).

The underlying principle of arrays is base pairing or hybridization i.e., A-T and G-C for DNA, and A-U and G-C for RNA. A sample from a mammal (e.g., a human) is allowed to hybridize with the polynucleotides and/or primers and/or probes on the array providing an expression profile/pattern of CNA. The CNA expression pattern of sepsis-specific sequences can be used to determine if a human has early stage sepsis. The array can be prepared by any method known in the art. In some embodiments, a microarray is prepared generally as disclosed in U.S. Pat. No. 7,655,397, the entirety of which is hereby incorporated by reference.

In some embodiments, the array comprises at least 2 polynucleotides selected from polynucleotides comprising or consisting of SEQ ID NOs: 1-57 or 94-148 or primers or probes specific for at least 2 of SEQ ID NOs: 1-57 or 94-148. In some embodiments, the array comprises at least 4 polynucleotides selected from polynucleotides comprising or consisting of SEQ ID NOs: 1-57 or 94-148 or primers or probes specific for at least 4 of SEQ ID NOs: 1-57 or 94-148. In another embodiment, the array comprises at least 5 polynucleotides selected from the polynucleotides comprising or consisting of SEQ ID NOs: 1-57 or 94-148 or primers or probes specific for at least 5 of SEQ ID NOs: 1-57 or 94-148. In another embodiment, the array comprises at least 10 polynucleotides selected from the polynucleotides comprising or consisting of SEQ ID NOs: 1-57 or 94-148 or primers or probes specific for at least 10 of SEQ ID NOs: 1-57 or 94-148. In some embodiments, the array comprises the 24 polynucleotides listed in Table 4 and/or primers and/or probes specific for the 24 polynucleotides listed in Table 4. The array generally includes many copies of the selected polynucleotides to facilitate detection. In some embodiments, the array comprises a million or more copies of each of the selected polynucleotides.

In a particular embodiment, the array comprises or consists of SEQ ID NOs: listed in Table 4 or primers or probes specific for the SEQ ID NOs: listed in Table 4. Also encompassed herein is an array comprising or consisting of subsets of SEQ ID NOs: listed in Table 4 or primers or probes specific for these SEQ ID NOs: as set forth herein.

Probes for detecting polynucleotides described herein can be designed and prepared using conventional methods. Software for modeling and designing probes, including determining hybridization and annealing conditions, for detecting a specific polynucleotide sequence are publically available, and include for example LightCycler® Probe Design Software (Roche Applied Science), Primer3 (Simgene), and FastPCR (PrimerDigital). See also techniques described by Illumina (Illumina Inc., 5200 Illumina Way, San Diego, Calif. 92122, USA).

The array can include positive indicator for sepsis sequences and/or probes for detecting same and negative and/or positive control sequences and/or probes.

Polynucleotides described herein can be amplified and/or detected via PCR, including but not limited to real-time PCR, multiplex PCR, nested PCR, solid phase PCR, miniprimer PCR, and the like. Primers and probes for amplifying and/or detecting polynucleotides described herein can be designed and prepared using conventional methods. Software for modeling and designing primers and probes, including determining hybridization, melting, annealing, and/or extensions conditions, for amplifying and/or detecting a specific polynucleotide sequence are publicly available, and include for example LightCycler® Probe Design Software (Roche Applied Science), Primer3 (Simgene), and FastPCR (PrimerDigital). See also techniques described by Illumina (Illumina Inc., 5200 Illumina Way, San Diego, Calif. 92122, USA). PCR conditions generally include the presence of four different nucleotide bases (adenosine, cytidine, guanosine, thymidine/uridine) and at least one polymerization-inducing agent such as a reverse transcriptase or a DNA polymerase. The primers are generally present in a suitable buffer, which may include constituents, which are co-factors or affect conditions such as pH and the like at various suitable temperatures. The primers are preferably single-strand nucleotide sequences, such that amplification efficiency of the desired polynucleotide is optimized. Double-stranded nucleotide sequences can also be utilized. The primers are typically at least about 15 nucleotides. In some embodiments, the primers can have a length of from about 15 to about 30, about 15 to about 50, about 15 to about 75, about 15 to about 100, or about 15 to about 500 nucleotides.

In some embodiments, primer sets are designed to amplify one or more of the sepsis-specific polynucleotides comprising or consisting of SEQ ID NOs: 1-57 or 94-148 and then the PCR products of the primer sets are screened for sepsis-specific sequences on an array as described herein.

Diagnostic kits comprising one or more primer pairs, and optional probes, for amplifying and detecting one or more polynucleotides described herein are also provided. The kit can optionally include nucleotide bases (adenosine, cytidine, guanosine, thymidine/uridine) and at least one polymerization-inducing agent such as a reverse transcriptase or a DNA polymerase. The kit can optionally include a suitable primer buffer, which may include constituents which are co-factors or affect conditions such as pH and the like at various suitable temperatures. The kit can optionally include an array as described herein.

The primers provided in the diagnostic kit are generally provided in pairs (forward primer and reverse primer) for amplifying/detecting a specific polynucleotide sequence. These primers can be used to amplify and detect CNAs in blood serum from humans, or any other appropriate biological sample from humans that may contain CNAs. Alternatively, CNAs can be extracted from the sample and then amplified by PCR using a diagnostic kit of the disclosure. The CNA expression pattern of sepsis-specific sequences detected by the diagnostic kit can be used to determine if a human has early stage sepsis even at a stage wherein no clinical symptoms of sepsis are apparent In addition to polynucleotide sequence specific primer pairs, labeled probes specific for each of the CNAs may be included in kits described herein. Labeled probes and use thereof in the context of, for example, multiplex qPCR provides for enhanced specificity of detection.

In some embodiments, the kit comprises primers for amplifying at least 2 polynucleotides selected from the polynucleotides comprising or consisting of SEQ ID NOs: 1-57 or 94-148, and optionally one or more probes for detecting the amplified product. In some embodiments, the kit comprises primers for amplifying at least 4 polynucleotides selected from the polynucleotides comprising or consisting of SEQ ID NOs: 1-57 or 94-148, and optionally one or more probes for detecting the amplified product. In another embodiment, the kit comprises primers for amplifying at least 5 polynucleotides selected from the polynucleotides comprising or consisting of SEQ ID NOs: 1-57 or 94-148, and optionally one or more probes for detecting the amplified product. In another embodiment, the kit comprises primers for amplifying at least 10 polynucleotides selected from the polynucleotides comprising or consisting of SEQ ID NOs: 1-57 or 94-148, and optionally one or more probes for detecting the amplified product. In some embodiments, the kit comprises primers for amplifying the 24 polynucleotides listed in Table 4, and optionally one or more probes for detecting the amplified product.

In a particular embodiment, the kit comprises or consists of SEQ ID NOs: listed in Table 4 and/or primers and/or probes specific for the SEQ ID NOs: listed in Table 4. Also encompassed herein are kits comprising or consisting of subsets of SEQ ID NOs: listed in Table 4 and/or primers and/or probes specific for these SEQ ID NOs: as set forth herein.

The present invention is described in the following Examples, which are set forth to aid in an understanding of the invention, and should not be construed to limit in any way the scope of the invention as defined in the claims which follow thereafter.

EXAMPLES

Example 1—Identification of Sepsis-Associated Polynucleotides in CNAs

Serum from healthy individuals (controls) and diseased patients (e.g., sepsis patients who were symptomatic or sepsis patients with early stage disease, but were asymptomatic) was harvested and total DNA was extracted from the serum samples. DNA was amplified and purified from the serum samples as described herein above. High-throughput paired-end DNA sequencing was performed and the resulting sequence reads were mapped to the human genome. Bioinformatics was used as described herein to identify DNA motifs that were present at distinctively high or low read count numbers in diseased humans, when compared to controls, corresponding to motifs that are over- and under-represented in sepsis patients. See, for example, Tables 1 and 3, which present motifs (Sequences) that are under-represented in sepsis patients (Table 1) or over-represented in sepsis patients (Table 3). The motifs identified reflect the host response to sepsis (i.e., the response of the human body to sepsis). The DNA motifs thus identified were used as targets for the development of a real-time Polymerase-Chain Reaction (RT-PCR) assay. In addition to the motifs, which are present at distinctively different levels in healthy controls and sepsis patients, motifs that were present at a highly similar level in healthy and diseased humans were also identified to allow for the normalization of the results. See, for example, Sequences presented in Table 2. The RT-PCR-evaluated motifs, which are used to discriminate between healthy controls and sepsis patients in a statistically significant manner, when evaluated alone or in combination with other motifs, are the subject basis for assays described herein.

All publications mentioned herein are hereby incorporated by reference in their entireties. While the foregoing invention has been described in some detail for purposes of clarity and understanding, it will be appreciated by one skilled in the art from a reading of the disclosure that various changes in form and detail can be made without departing from the true scope of the invention in the appended claims.

Specific examples of methods and kits have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

The embodiments of the invention described above are intended to be exemplary only. Those skilled in this art will understand that various modifications of detail may be made to these embodiments, all of which come within the scope of the invention.

The invention claimed is:

1. A method for treating sepsis comprising administering to a human identified as having sepsis a therapeutically effective amount of at least one agent used to treat sepsis, wherein the human is identified as having sepsis by analyzing a serum sample comprising analyzing the level of circulating nucleic acid from the human serum sample for circulating nucleic acids of SEQ ID NO 10-30 and SEQ ID NOs: 59, 61 and 68 to detect under-representation of at least one nucleic acid sequence having at least 95% identity to SEQ ID NOs: 10-30 relative to a nucleic acid sequence having at least 95% identity to SEQ ID NOs: 59, 61 and 68 to identify the human as having sepsis.

2. A method for treating sepsis comprising administering to a human identified as having sepsis a therapeutically effective amount of at least one agent used to treat sepsis, wherein the human is identified as having sepsis by analyzing a serum sample comprising analyzing the level of circulating nucleic acid from the human serum sample for circulating nucleic acids of SEQ ID NO 10-30 and SEQ ID NOs: 59, 61 and 68 to detect under-representation of at least one nucleic acid sequence having at least 95% identity to SEQ ID NOs: 10-30 relative to a nucleic acid sequence having at least 95% identity to SEQ ID NOs: 59, 61 and 68 wherein the under-representation of the at least one SEQ ID NOs: 10-30 in the serum sample is a positive indicator that the human is in need of the administering.

3. The method of claim 1, wherein the at least one nucleic acid sequence having at least 95% identity to SEQ ID NOs: 10-30 is at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty.

4. The method of claim 1, wherein the detecting of the under-representation comprises at least one of a polymerase chain reaction (PCR)-based detection method, a hybridization-based method, enzyme-linked immunosorbent assay (ELISA), radioimmunoassay (MA), solid-phase enzyme immunoassay (EIA), mass spectrometry, or microarray analysis.

5. The method of claim 4, wherein the PCR-based detection method is performed using primer pairs, wherein each primer pair is specific for one of SEQ ID NOs: 10-30, 59, 61, and 68.

6. The method of claim 5, wherein the primer pairs specific for one of SEQ ID NOs: 10-30, 59, 61, and 68 are SEQ ID NO 192-212, 249-269, 298, 300, 307, 334, 336, 343.

7. The method of claim 6, further comprising sequencing amplification products generated by the PCR-based detection method.

8. The method of claim 1, wherein the at least one agent used to treat sepsis comprises at least one of an antibiotic, anti-fungal agent, anti-viral agent, anti-parasitic agent, or fluids suitable for intravenous administration.

* * * * *